United States Patent
Boeckman et al.

(10) Patent No.: US 10,660,884 B2
(45) Date of Patent: May 26, 2020

(54) PHOSPHONATE-CHLOROQUINE CONJUGATES AND METHODS USING SAME

(71) Applicant: University of Rochester, Rochester, NY (US)

(72) Inventors: Robert Boeckman, Honeye Falls, NY (US); Brendan Boyce, Woodbury, NY (US); Lifeng Xiao, Rochester, NY (US); Zhenqiang Yao, Pittsford, NY (US); Frank H. Ebetino, Venice, FL (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/772,893

(22) PCT Filed: Nov. 2, 2016

(86) PCT No.: PCT/US2016/060071
§ 371 (c)(1),
(2) Date: May 2, 2018

(87) PCT Pub. No.: WO2017/079260
PCT Pub. Date: May 11, 2017

(65) Prior Publication Data
US 2018/0318282 A1    Nov. 8, 2018

Related U.S. Application Data

(60) Provisional application No. 62/249,381, filed on Nov. 2, 2015.

(51) Int. Cl.
*C07F 9/60* (2006.01)
*A61K 31/4706* (2006.01)
*A61K 47/54* (2017.01)

(52) U.S. Cl.
CPC ........ *A61K 31/4706* (2013.01); *A61K 47/548* (2017.08); *C07F 9/60* (2013.01)

(58) Field of Classification Search
CPC ...... A61K 31/4706; A61K 47/548; C07F 9/60
See application file for complete search history.

(56) References Cited

U.S. PATENT DOCUMENTS

2014/0271483 A1    9/2014  Satchi-Fainaro et al.

FOREIGN PATENT DOCUMENTS

| JP | 11302177 A | * | 11/1999 |
| JP | 2004-67645 | * | 3/2004 |
| WO | 1998/000438 A1 | | 1/1998 |
| WO | 2016/172552 A1 | | 10/2016 |

OTHER PUBLICATIONS

Osorio, Am J Trop Med Hyg, vol. 61(6), 1999, 968-972. (Year: 1999).*
Xiu et al. "Chloroquine reduces osteoclastogenesis in murine osteoporosis by preventing TRAF3 degradation", J. Clinical Investigation, 2013, 124:297-310.
Russell et al."Mechanisms of action of bisphosphonates: similarities and differences and their potential influence on clinical efficacy" Osteoporos Int, 2008, 19:733-759.
Hyrich et al. "Predictors of response to anti-TNF-therapy among patients with rheumatoid arthritis: results from the British Society for Rheumatology Biologics Register" Rheumatology, 2006, 45:1558-1565.
Symmons et al. "The world of biologics" Lupus, 2006, 15:122-126.
Motten et al. "Photophysical studies on antimalarial drugs" Photochern Photobiol, 1999, 69:282-287.
Costedoat-Chalumeau et al. "A Critical Review of the Effects of Hydroxychloroquine and Chloroquine on the Eye" Clin Rev Allergy Immunol, 2015, 49(3):317-326.
Bagi et al "Targeting of therapeutic agents to bone to treat metastatic cancer," Adv Drug Deliv Rev., 2005 57(7):995-1010.
Morioka et al. "Design, synthesis, and biological evaluation of novel estradiol—bisphosphonate conjugates as bone-specific estrogens" Bioorg Med Chem, 2010, 18:1143-1148.
Tanaka et al. "Synthesis and in vitro evaluation of bisphosphonated glycopeptide prodrugs for the treatment of osteomyelitis" Bioorg Med Chern Lett, 2010, 20:1355-1359.
Arns et al. "'Design and synthesis of novel bone-targeting dual-action pro-drugs for the treatment and reversal of osteoporosis" Bioorg Med Chem, 2012, 20:2131-2140.
Wasnich et al "Antifracture Efficacy of Antiresorptive Agents Are Related to Changes in Bone Density" J Clin Endocrinol Metab, 2000, 85:231-236.
Cummings et al. "Improvement in spine bone density and reduction in risk of vertebral fractures during treatment with antiresorptive drugs" Am J Med, 2002, 112:281-289.
Rasmusson et al. "Bisphosphonate associated osteonecrosis of the jaw: an update on pathophysiology, risk factors, and treatment" Int J Dent 2014:471035.
Kennel et al "Adverse effects of bisphosphonates: implications for osteoporosis management" Mayo Clin Proc, 2009, 84:632-637.
Scott "Denosumab: A Review of its Use in Postmenopausal Women with Osteoporosis" Drugs Aging, 2014, 31:555-76.
Mandema et al. "Time Course of Bone Mineral Density Changes With Denosumab Compared With Other Drugs in Postmenopausal Osteoporosis: A Dose-Response—Based Meta-Analysis" J Clin Endocrinol Metab, 2014, 99:3746-3755.
Hoes et al. "Management of osteoporosis in rheumatoid arthritis patients" Expert Opin Pharmacother, 2015, 16:559-571.
Watt et al. "There is still a care gap in osteoporosis management for patients with rheumatoid arthritis. Joint Bone Spine" Joint Bone Spine, 2014, 81:347-351.

(Continued)

*Primary Examiner* — D Margaret M Seaman
(74) *Attorney, Agent, or Firm* — Weisun Rao; Venture Partner, LLC

(57) ABSTRACT

The present invention provides compositions and methods for providing controllable local delivery of a conjugate of chloroquine (CQ) and a bisphosphonate to treat diseases characterized by abnormal bone metabolism. In certain embodiments, the invention is used as a treatment for a subject with diseases and disorders characterized by bone loss.

15 Claims, 19 Drawing Sheets

(56) References Cited

OTHER PUBLICATIONS

Yao et al. "NF-κb p100 limits TNF-induced bone resorption in mice by a TRAF3-dependent mechanism" J Clin Invest, 2009, 119:3024-3034.
Coxon et al."Visualizing mineral binding and uptake of bisphosphonate by osteoclasts and non-resorbing cells" Bone, 2008, 42:848-860.
Hughes et al. "Bisphosphonates promote apoptosis in murine osteoclasts in vitro and in vivo" J Bone Miner Res, 1995, 10:1478-1487.
Yates et al. "Effects of a synthetic peptide of a parathyroid hormone-related protein on calcium homeostasis, renal tubular calcium reabsorption, and bone metabolism in vivo and in vitro in rodents," 1988, 81(3):932-8.
Ahmed et al. "Renal function in a rat model of analgesic nephropathy: effect of chloroquine," 2003, J Pharmacol Exp Ther 305:123-30.
Boyce, "Advances in osteoclast biology reveal potential new drug targets and new roles for osteoclasts," 2013, J Bone Miner res 28:711-22.
Engin et al., "Dimorphic effects of Notch signaling in bone homeostasis," 2008, Nat Med 14:299-305.
Franzoso et al., "Requirement for NF-κB in osteoclast and B-cell development," 1997, Gen Dev 11:3482-3496.
Hughes et al., "Estrogen promotes apoptosis of murine osteoclasts mediated by TGF-beta" 1996, Nat Med 2:1132-6.
Liu et al., "Novel EP4 Receptor Agonist-Bisphosphonate Conjugate Drug (C1) Promotes Bone Formation and Improves Vertebral Mechanical Properties in the Ovariectomized Rat Model of Postmenopausal Bone Loss," 2014, J Bone Min. Res. 30:670-80.
Morello et al., "CRTAP is required for prolyl 3- hydroxylation and mutations cause recessive osteogenesis imperfecta," 2006, Cell 127:297-304.
Mundy et al., "Stimulation of bone formation in vitro and in rodents by statins" 1999, 286:1946-49.
Todorovic et al., "Acute pretreatment with chloroquine attenuates renal I/R injury in rats," 2014, PLoS One 9:e92673.

\* cited by examiner

PHOSPHONATE-CHLOROQUINE CONJUGATES AND METHODS USING SAME

CROSS-REFERENCE TO RELATED APPLICATIONS

This application is a U.S. national phase application filed under 35 U.S.C. § 371 claiming benefit to International Patent Application No. PCT/US 16/60071, filed Nov. 2, 2016, which is entitled to priority under 35 U.S.C. § 119(e) to U.S. Provisional Patent Application No. 62/249,381, filed Nov. 2, 2015, each of which application is hereby incorporated herein by reference in its entirety.

BACKGROUND OF THE INVENTION

Osteoporosis (OP) is a major health problem affecting millions of Americans as they age because of its associated increased risk of bone fractures and death. It is associated with sex steroid deficiency and low-level chronic inflammation both of which increase with age and are accompanied by increased production of pro-inflammatory cytokines, including tumor necrosis factor (TNF). These cytokines stimulate the formation and bone destructive activity of osteoclasts (OCs), the cells that resorb (degrade) bone. Bisphosphonates (BPs) are currently the most widely prescribed drugs used to treat OP (Russell et al., 2008, Osteoporos Int 19:733-59). They inhibit the activity, but not the formation of OCs. Although they prevent bone loss and reduce fractures, poor patient compliance and more recent fears about side-effects have limited their use. In addition, many individuals are unaware that they have osteoporosis. Thus, many patients go untreated. Osteoporosis can also complicate inflammatory bone diseases, such as rheumatoid arthritis (RA) and psoriatic arthritis, in which pro-inflammatory cytokine production is also increased.

RA patients can have devastating joint destruction and generalized and localized osteoporosis. They are treated with a variety of drugs to reduce inflammation and joint destruction, including corticosteroids, non-steroidal anti-inflammatory drugs, methotrexate and hydroxychloroquine (HCQ), and ultimately TNF inhibitors, but only 50-60% of patients achieve successful control of symptoms and signs of joint inflammation, despite the success of these combination therapies (Hyrich et al., 2006, Rheumatology 45:1558-65; Symmons and Silman, 2006, Lupus 15:122-6). HCQ and methotrexate act as anti-inflammatory drugs and their administration to patients who move on to TNF inhibitors typically is continued. However, the mechanism of action of HCQ is poorly understood and it also has side-effects, including blindness in up to 0.5-1% of patients (Motten et al., 1999, Photochem Photobiol 69:282-7; Costedoat-Chalumeau et al., 2015, Clin Rev Allergy Immunol). HCQ replaced chloroquine (CQ) decades ago for treatment of RA in the US and Europe because HCQ has a lower toxicity profile, including less damage to the eye and other tissues. Recently it was reported that CQ prevents bone resorption and osteoporosis in mouse models of postmenopausal osteoporosis and hyperparathyroidism (Xiu Y et al., 2014, J Clin Invest 124:297-310). Unlike CQ, HCQ does not prevent bone resorption in mice, and there are no definitive data showing that either of these drugs has anti-resorptive effects in humans. CQ is still widely prescribed in many 3$^{rd}$ world countries because it is much cheaper than HCQ. Furthermore, only 50-60% of RA patients respond successfully to these treatments. Thus, there is an unmet need to improve efficacy of existing drugs and develop new approaches to therapy.

Recent attempts to target estrogen analogs (Morioka et al., 2010, Bioorg Med Chem 18:1143-8), antibiotic agents (Tanaka et al., 2010, Bioorg Med Chem Lett 20:1355-9), and prostaglandins (Arns et al., 2012, Bioorg Med Chem 20:2131-40) to bone with BPs through carbamate linker conjugation have been successful, specifically through chemical linkages that allow subsequent release of an active agent at the bone surface. This approach improved the efficacy of estradiol to inhibit bone resorption, while limiting side-effects, such as endometrial hyperplasia (Morioka et al., 2010, Bioorg Med Chem 18:1143-8). In a related effort, this BP-drug conjugation technology facilitated adequate delivery to bone and slow release of prostaglandin "warheads" in radiolabelled PK studies to estimate concentrations of delivered drug (Arns et al., 2012, Bioorg Med Chem 20:2131-40). Carbamate linkers are cleaved by enzymatic or by hydrolytic means in the acidic microenvironment under the osteoclast ruffled border in bone resorption sites, thus releasing the active drug ("warhead/payload") (Arns et al., 2012, Bioorg Med Chem 20:2131-40).

Bisphosphonates have been used for decades to treat osteoporosis and reduce fracture rates in the aging population (Wasnich and Miller, 2000, J Clin Endocrinol Metab 85:231-6; Cummings et al., 2002, Am J Med 112:281-9). However, poor patient compliance and more recent fears about side-effects with BPs, including osteonecrosis and atypical fractures, have limited their use, and thus many patients go untreated (Rasmusson and Abtahi, 2014, Int J Dent 2014:471035; Kennel and Drake, 2009, Mayo Clin Proc 84:632-7). More recently, Denosumab, an anti-RANKL antibody has been developed and has anti-resorptive efficacy similar to that of BPs (Scottt, 2014, Drugs Aging 31:555-76; Mandema et al., 2014, J Clin Endocrinol Metab 99:3746-55). However, prescription of Denosumab has lagged behind expectations and therefore has not filled this gap in therapy. Thus, there is a need to develop new therapies to treat this disease as the aging population increases. Patients with RA also develop systemic as well as localized osteoporosis around affected joints, in part as a result of the effects of the increased levels of pro-inflammatory/osteoclastogenic cytokines and also because of the adverse effects of corticosteroids on the skeleton (Hoes et al., 2015, Expert Opin Pharmacother 16:559-71; Watt et al., 2014, Joint Bone Spine 81:347-51). Patients on long-term steroid treatment also require effective anti-resorptive therapy, but few patients receive them during the early years of their disease when they can lose significant amounts of bone. Most RA patients are treated with HCQ, but if it does not have anti-resorptive activity in humans, similar to findings in mice, it will not help prevent this bone loss.

There is a need in the art for new compounds and methods that selectively target the delivery of compounds, such as CQ specifically to bone tissue in order to ameliorate and/or prevent the toxic side effects arising from systemic distribution and to make dose escalation possible in order to improve therapeutic outcomes. The present invention fulfills this need.

BRIEF SUMMARY OF THE INVENTION

The invention includes a compound where the compound is selected from:
i) a compound of formula (I):

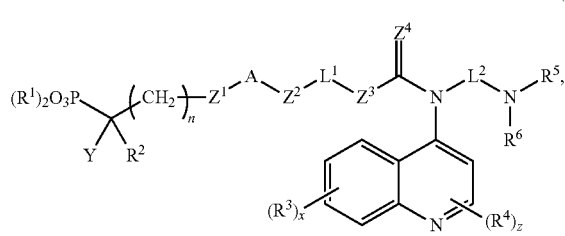

(I)

wherein in formula (I):
each occurrence of $R^1$ is independently selected from the group consisting of hydrogen and alkyl;
$R^2$ is selected from the group consisting of hydrogen, alkyl, —$OR^8$, —$N(R^8)(R^9)$, and halogen;
each occurrence of $R^3$ and $R^4$ is independently selected from the group consisting of alkyl, haloalkyl, heteroalkyl, halogen, —CN, —$NO_2$, —$OR^{16}$, —$SR^{16}$, —$S(=O)R^{16}$, —$S(=O)_2R^{16}$, —$NHS(=O)_2R^{16}$, —$C(=O)R^{16}$, —$OC(=O)R^{16}$, —$CO_2R^{16}$, —$OCO_2R^{16}$, —$CH(R^{16})_2$, —$N(R^{16})_2$, —$C(=O)N(R^{16})_2$, —$OC(=O)N(R^{16})_2$, —$NHC(=O)NH(R^{16})$, —$NHC(=O)R^{16}$, —$NHC(=O)OR^{16}$, —$C(OH)(R^{16})_2$, and —$C(NH_2)(R^{16})_2$, wherein the alkyl, haloalkyl, or heteroalkyl is optionally substituted;
$R^5$, $R^6$, $R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;
$L^1$ and $L^2$ are each independently selected from the group consisting of a bond, alkyl, aryl, cycloalkyl, alkylaryl, alkylcycloalkyl, alkylaryl, and arylalkyl wherein the alkyl, aryl, cycloalkyl, alkylaryl, alkylaryl, arylalkyl or alkylcycloalkyl is optionally substituted with one to four substituents selected from the group consisting of hydroxyl, alkoxy, alkenyl, cycloalkyl, aryl, heteroaryl, halo, cyano and amino;
Y is selected from the group consisting of —$PO(OR^{10})(OR^{11})$, —$PO(R^{10})(OR^{11})$, —$CO_2R^{10}$, and —$SO_3R^{10}$;
$R^{10}$ and $R^{11}$ are each independently selected from the group consisting of hydrogen and alkyl;
$Z^1$ is selected from the group consisting of a bond, $CH_2$ and $NR^{12}$;
A is selected from the group consisting of a bond, $CH_2$, $C(=O)$, $C(=NR^{13})$, and $C(=S)$;
$Z^2$ is selected from the group consisting of a bond, $CH_2$, $NR^{14}$, S, and O;
$Z^3$ is selected from the group consisting of a bond, $CH_2$, $NR^7$, S, and O
$Z^4$ is selected from the group consisting of O, $NR^{15}$, and S;
$R^7$, $R^{12}$, $R^{13}$, $R^{14}$, and $R^{15}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

each occurrence of $R^{16}$ is independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;
n is an integer from 0 to 10;
x is an integer from 0 to 4; and
z is an integer from 0 to 2; and
ii) a compound of formula (II):

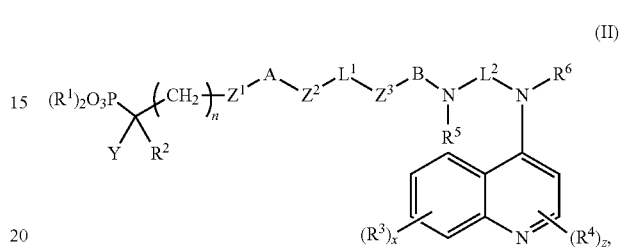

(II)

wherein in formula (II):
each occurrence of $R^1$ is independently selected from the group consisting of hydrogen and alkyl;
$R^2$ is selected from the group consisting of hydrogen, alkyl, —$OR^8$, —$N(R^8)(R^9)$, and halogen;
each occurrence of $R^3$ and $R^4$ is independently selected from the group consisting of alkyl, haloalkyl, heteroalkyl, halogen, —CN, —$NO_2$, —$OR^{16}$, —$SR^{16}$, —$S(=O)R^{16}$, —$S(=O)_2R^{16}$, —$NHS(=O)_2R^{16}$, —$C(=O)R^{16}$, —$OC(=O)R^{16}$, —$CO_2R^{16}$, —$OCO_2R^{16}$, —$CH(R^{16})_2$, —$N(R^{16})_2$, —$C(=O)N(R^{16})_2$, —$OC(=O)N(R^{16})_2$, —$NHC(=O)NH(R^{16})$, —$NHC(=O)R^{16}$, —$NHC(=O)OR^{16}$, —$C(OH)(R^{16})_2$, and —$C(NH_2)(R^{16})_2$, wherein the alkyl, haloalkyl, or heteroalkyl is optionally substituted;
$R^5$, $R^6$, $R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;
$L^1$ and $L^2$ are each independently selected from the group consisting of a bond, alkyl, aryl, cycloalkyl, alkylaryl, alkylcycloalkyl, alkylaryl, and arylalkyl wherein the alkyl, aryl, cycloalkyl, alkylaryl, alkylaryl, arylalkyl or alkylcycloalkyl is optionally substituted with one to four substituents selected from the group consisting of hydroxyl, alkoxy, alkenyl, cycloalkyl, aryl, heteroaryl, halo, cyano and amino;
Y is selected from the group consisting of —$PO(OR^{10})(OR^{11})$, —$PO(R^{10})(OR^{11})$, —$CO_2R^{10}$, and —$SO_3R^{10}$;
$R^{10}$ and $R^{11}$ are each independently selected from the group consisting of hydrogen and alkyl;
$Z^1$ is selected from the group consisting of a bond, $CH_2$ and $NR^{12}$;
A and B are each independently selected from the group consisting of a bond, $CH_2$, $C(=O)$, $C(=NR^{13})$, and $C(=S)$;
$Z^2$ is selected from the group consisting of a bond, $CH_2$, $NR^{14}$, S, and O;
$Z^3$ is selected from the group consisting of a bond, $CH_2$, $NR^7$, S, and O
$Z^4$ is selected from the group consisting of O, $NR^{15}$, and S;
$R^7$, $R^{12}$, $R^{14}$, and $R^{15}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

each occurrence of $R^{13}$ and $R^{16}$ is independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

n is an integer from 0 to 10;
x is an integer from 0 to 4; and
z is an integer from 0 to 2; or
a pharmaceutically acceptable salt thereof; or an isomer thereof; or a mixture of isomers thereof.

In one embodiment, the compound of formula (I) is a compound of formula (III):

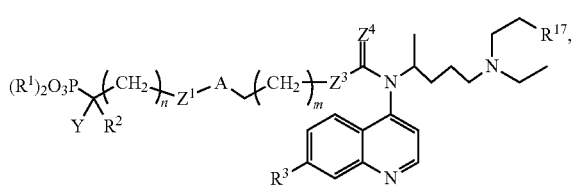

(III)

wherein in formula (III):
each occurrence of $R^1$ is independently selected from the group consisting of hydrogen and alkyl;
$R^2$ is selected from the group consisting of hydrogen, alkyl, —$OR^8$, —$N(R^8)(R^9)$, and halogen;
$R^3$ is selected from the group consisting of halogen, $NO_2$, —$CF_3$, —$OR^{16}$, and —$CH_3$;
Y is selected from the group consisting of —$PO(OR^{10})(OR^{11})$, —$PO(R^{10})(OR^{11})$, —$CO_2R^{10}$, and —$SO_3R^{10}$;
$Z^1$ is selected from the group consisting of $CH_2$ and $NR^{12}$;
A is selected from the group consisting of $CH_2$, C(=O), C(=NR^{13}), and C(=S);
$Z^3$ is selected from the group consisting of $CH_2$, $NR^7$, S, and O;
$Z^4$ is selected from the group consisting of O, $NR^{15}$, and S;
$R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;
$R^{10}$ and $R^{11}$ are each independently selected from the group consisting of hydrogen and alkyl;
$R^7$, $R^{12}$, $R^{13}$, $R^{14}$, $R^{15}$, and $R^{16}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^{17}$ is selected from the group consisting of hydrogen, —$OR^{18}$, —$CH_3$, and —$CF_3$;
$R^{18}$ is selected from the group consisting of hydrogen and alkyl, wherein alkyl is optionally substituted with one to four substituents selected from the group consisting of hydroxyl, alkoxy, alkenyl, cycloalkyl, aryl, heteroaryl, halo, cyano and amino;

n is an integer from 0 to 10; and
m is an integer from 0 to 10; or
a pharmaceutically acceptable salt thereof; or an isomer thereof; or a mixture of isomers thereof.

In one embodiment, Y is —$PO_3(R^1)_2$. In one embodiment, $R^3$ is Cl. In one embodiment, C is selected from the group consisting of alkyl, aryl, and alkylaryl. In one embodiment, $L^2$ is alkyl substituted with one to four substituents selected from the group consisting of hydroxyl, alkoxy, alkenyl, cycloalkyl, aryl, heteroaryl, halo, cyano and amino. In one embodiment, $Z^2$ and $Z^4$ are each O.

In one embodiment, the compound of formula (I) is a compound of formula (IV):

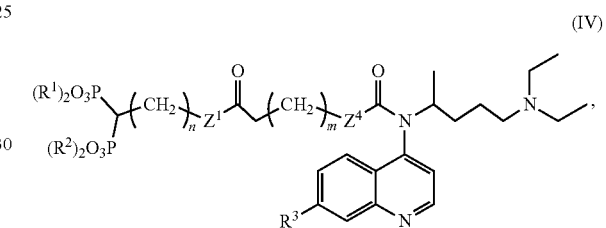

(IV)

wherein in formula (IV):
each occurrence of $R^1$ and $R^2$ is independently selected from the group consisting of hydrogen and alkyl;
$R^3$ is selected from the group consisting of halogen, —$CF_3$, —$OR^{16}$, and —$CH_3$;
$Z^1$ is selected from the group consisting of $CH_2$ and $NR^{12}$;
$Z^4$ is selected from the group consisting of O, $NR^{15}$, and S;
$R^{12}$, $R^{15}$, and $R^{16}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

n is an integer from 0 to 10; and
m is an integer from 0 to 10; or
a pharmaceutically acceptable salt thereof; or an isomer thereof; or a mixture of isomers thereof.

In one embodiment, $R^3$ is Cl.

In one embodiment, the compound of formula (I) is selected from the group consisting of:

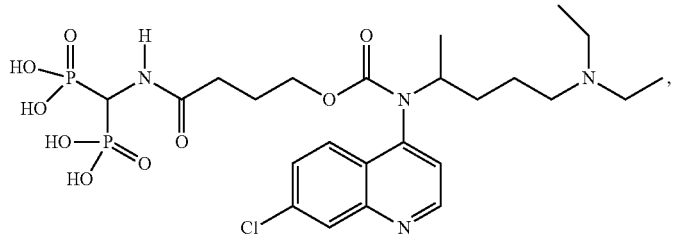

-continued
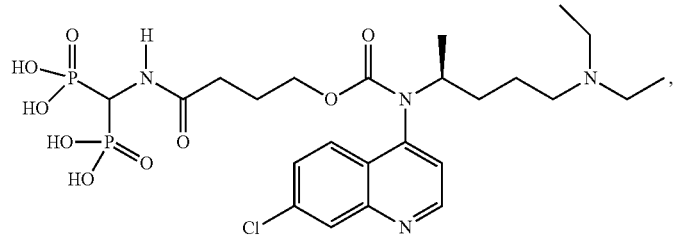
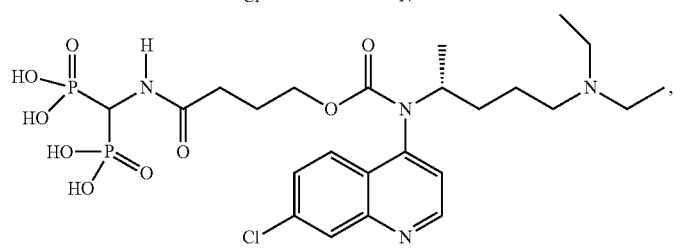
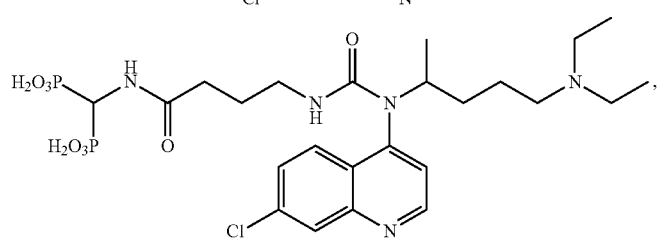
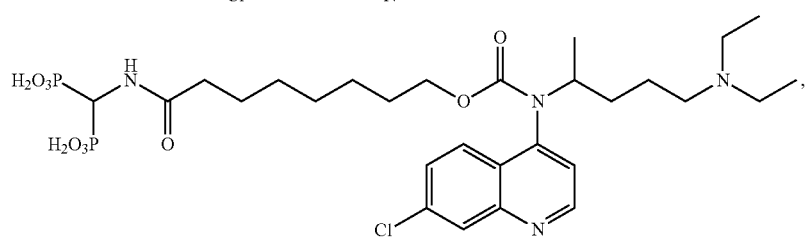
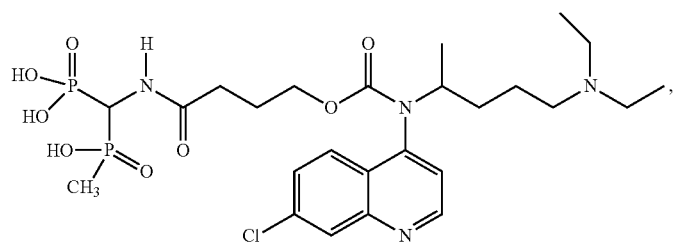
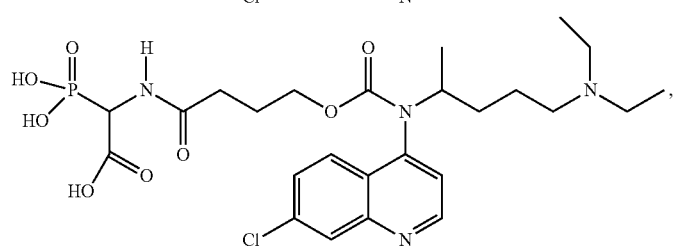
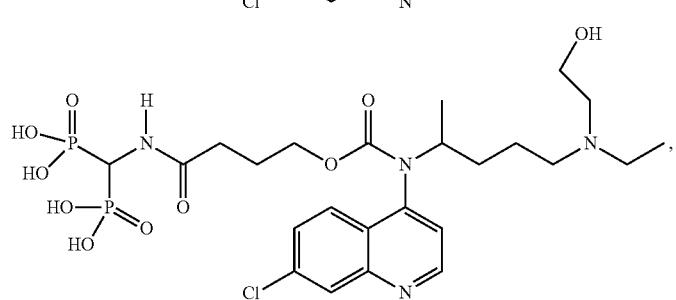

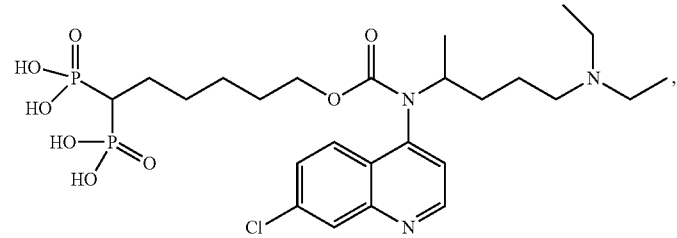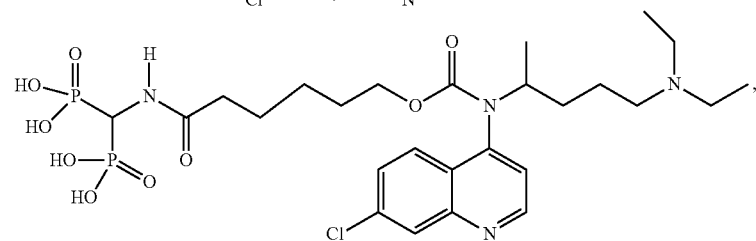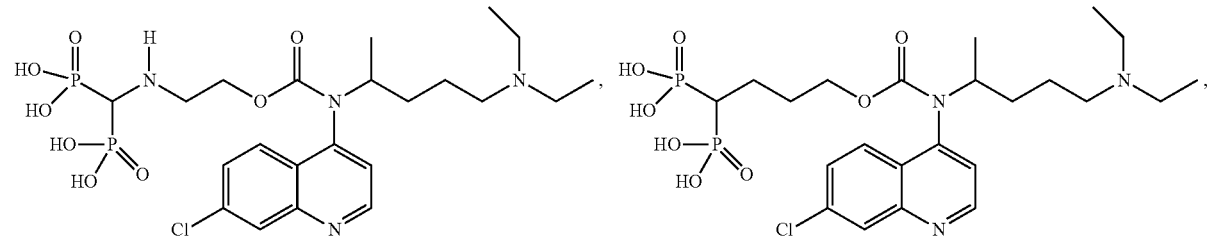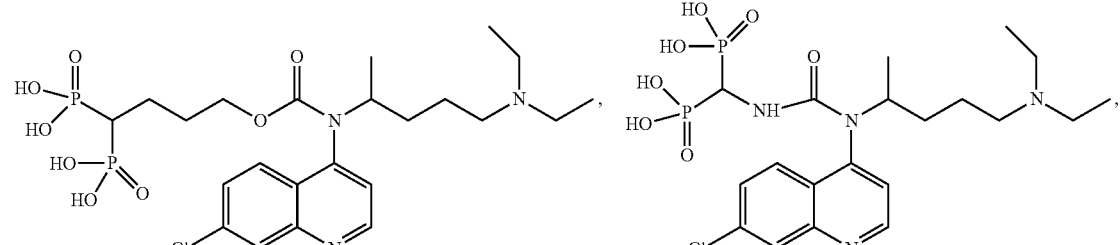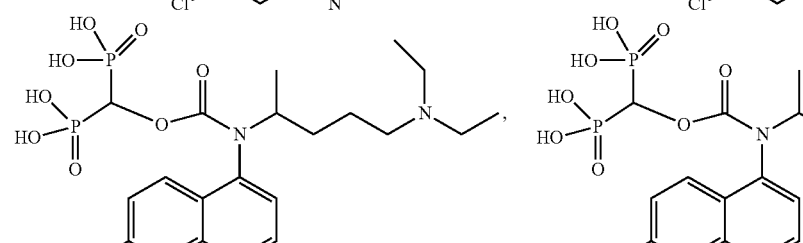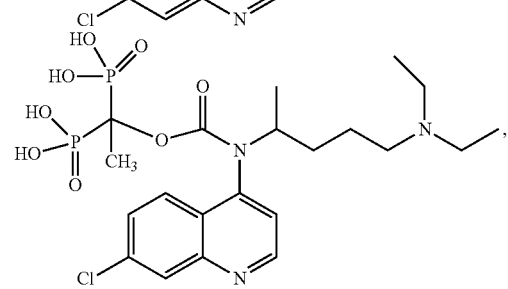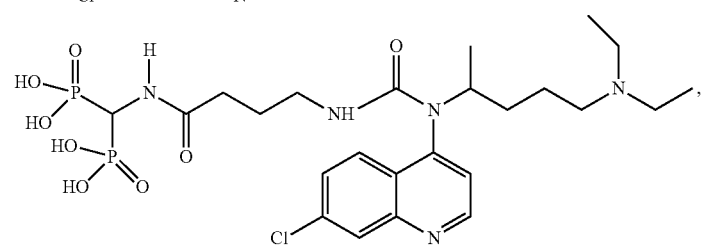

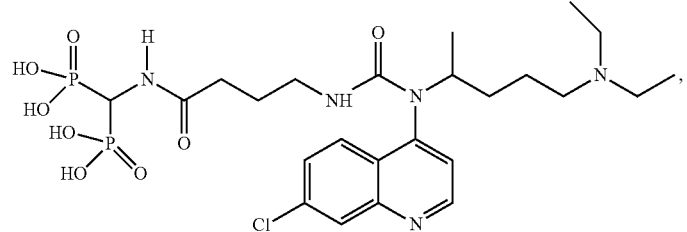
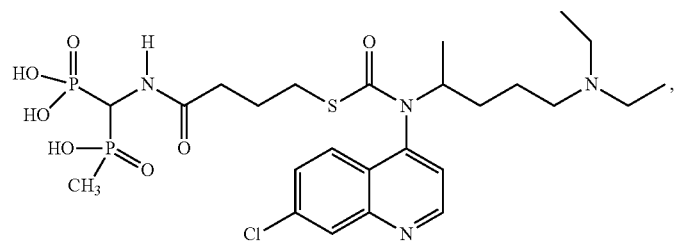
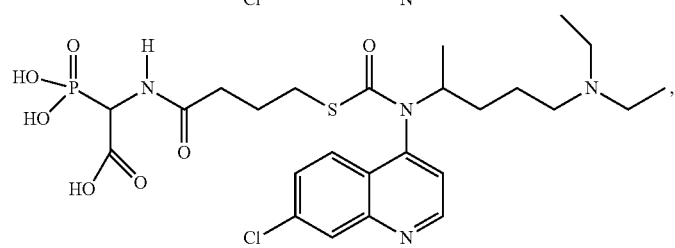
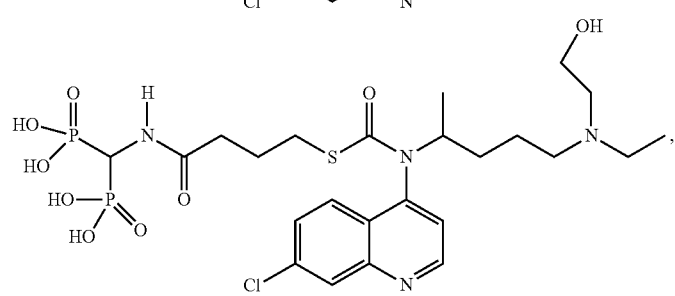
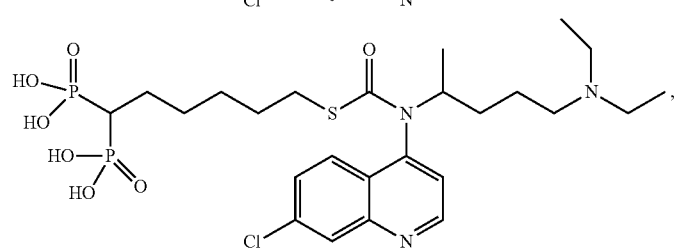
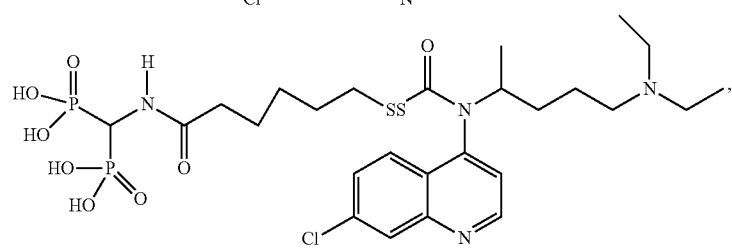
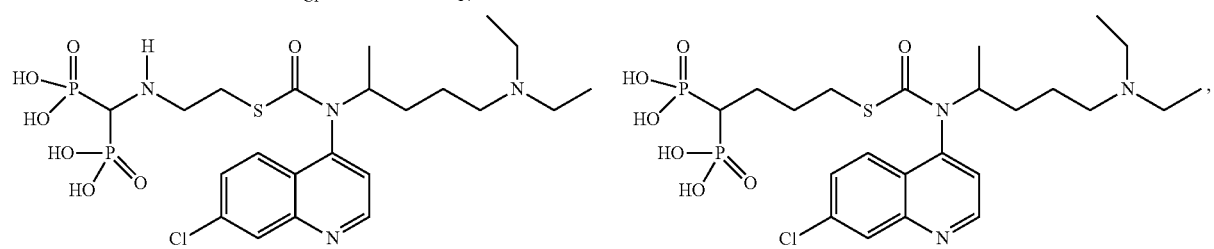

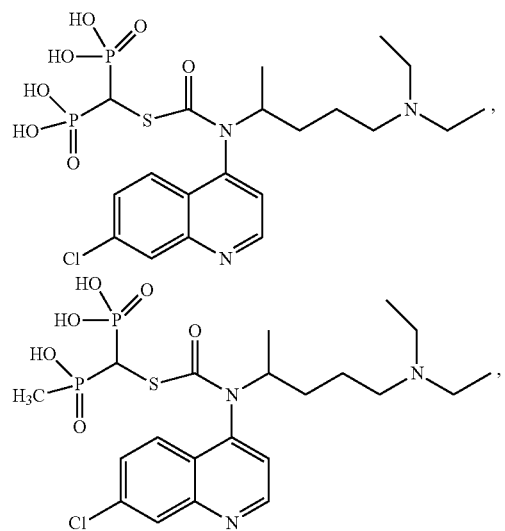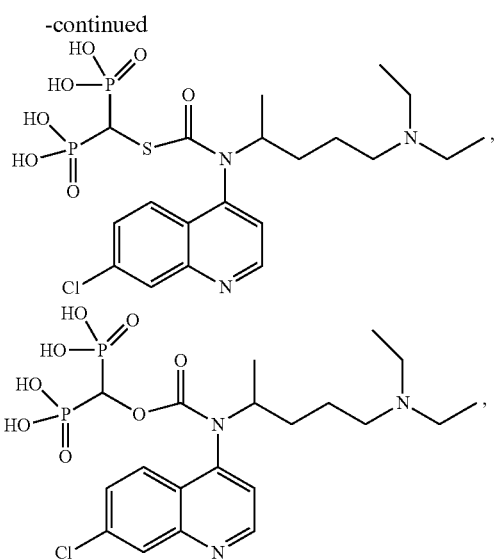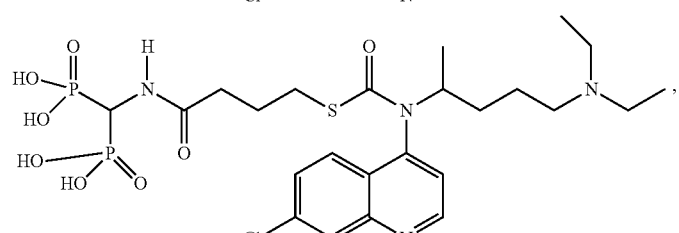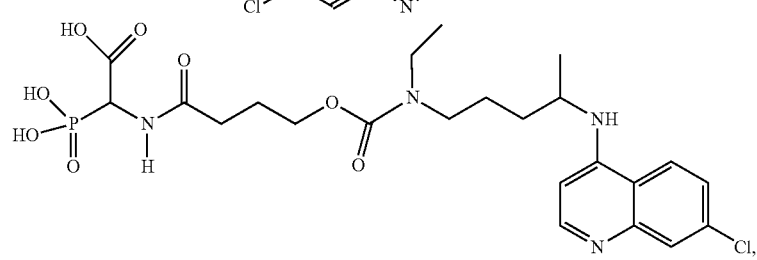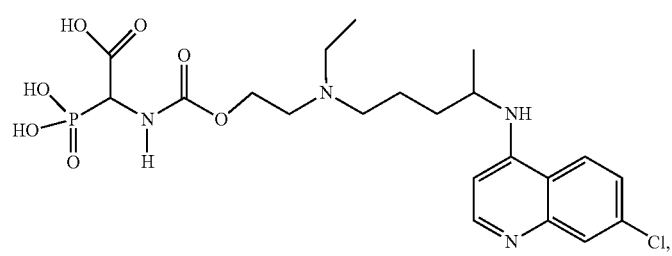

-continued
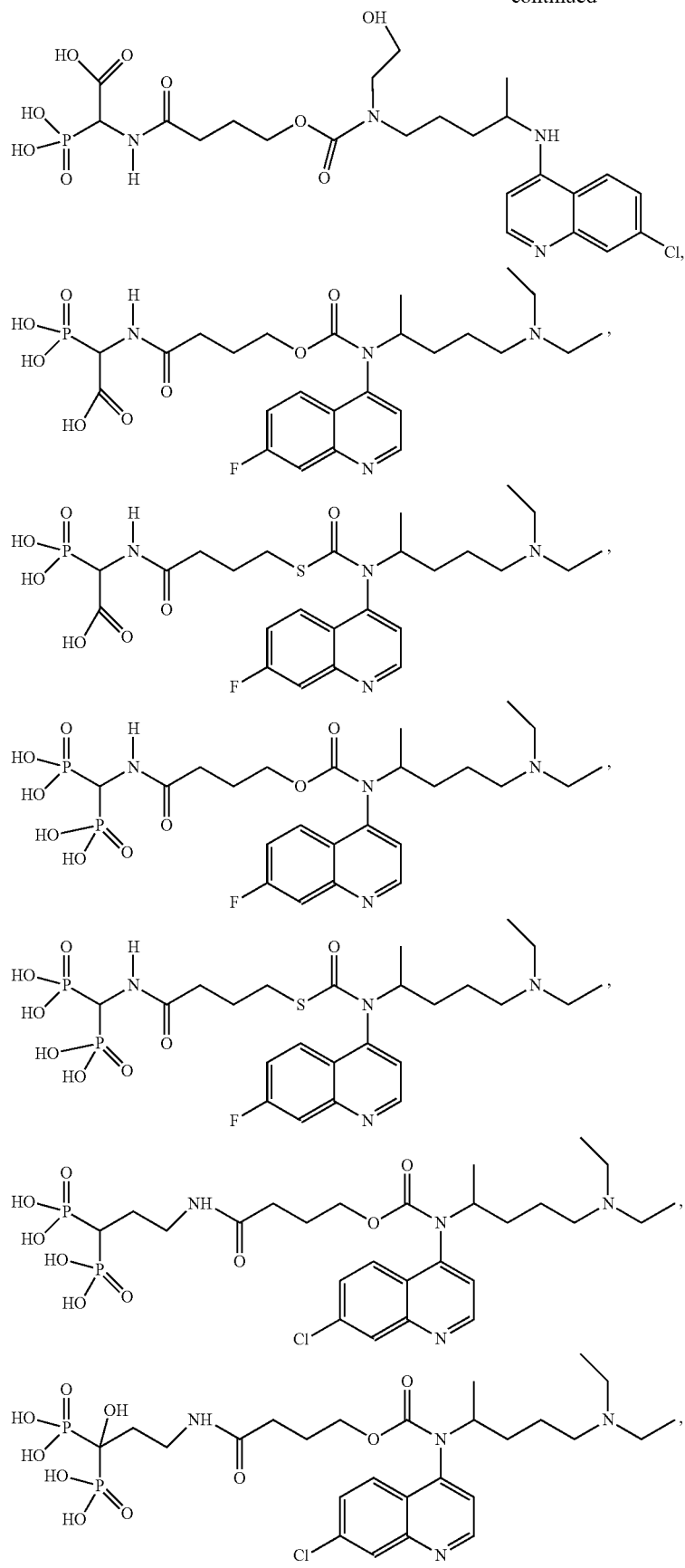

-continued
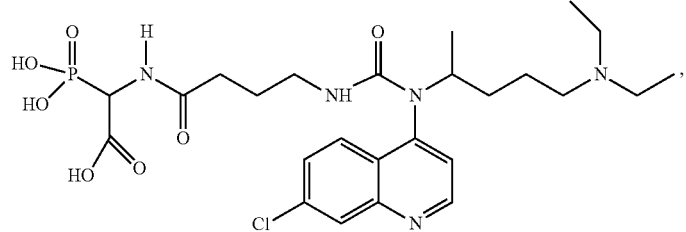
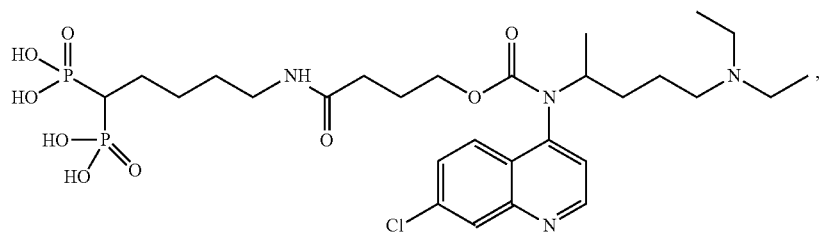
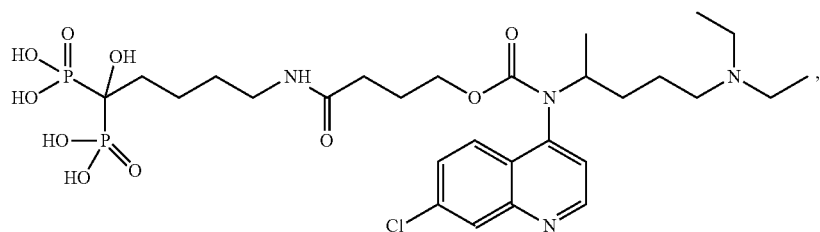
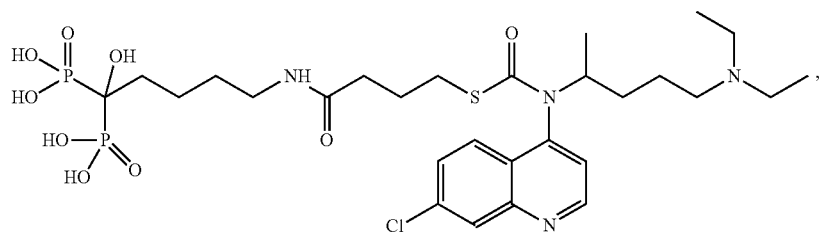
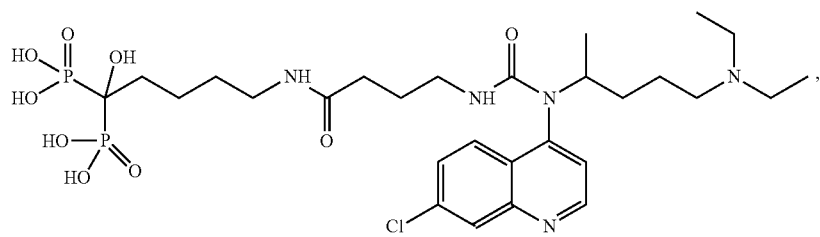
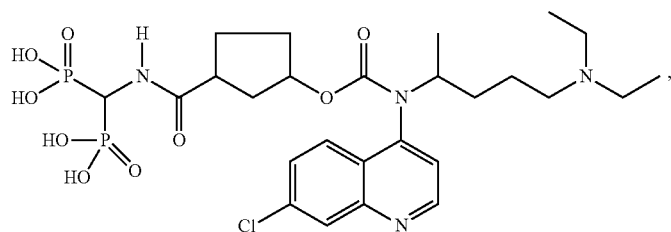
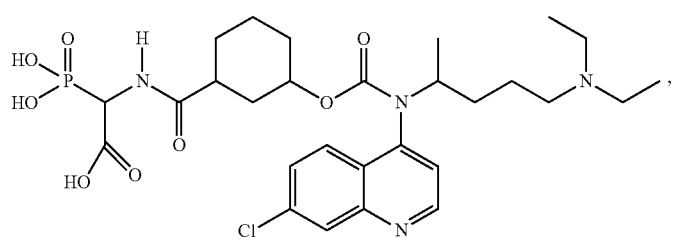

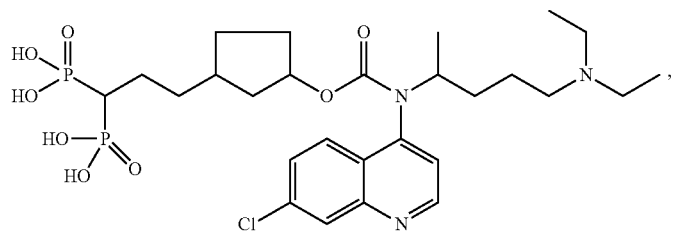,
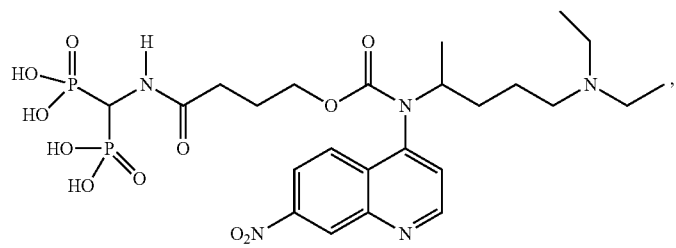,
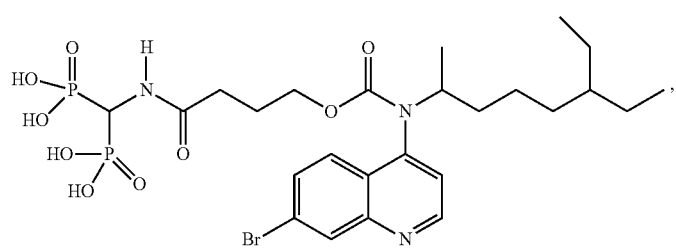,
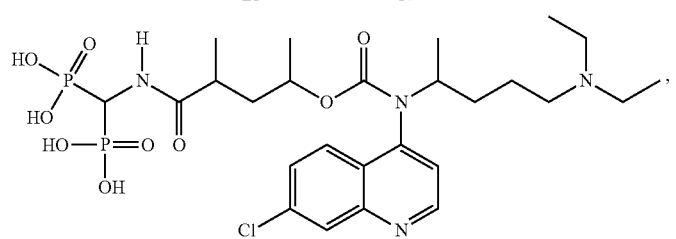,
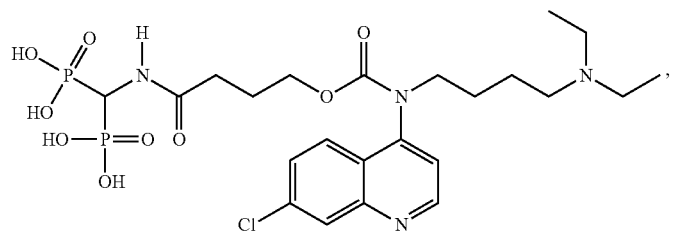,
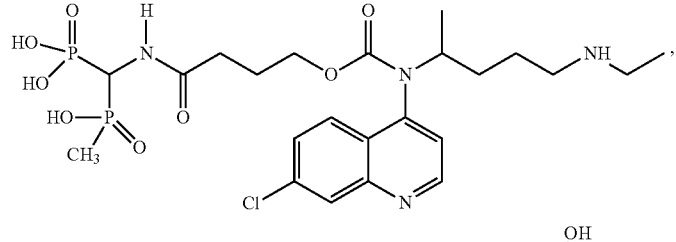,
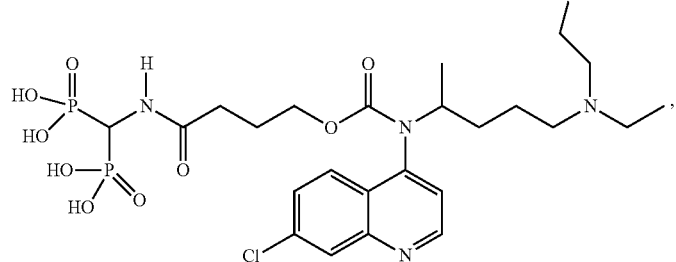,

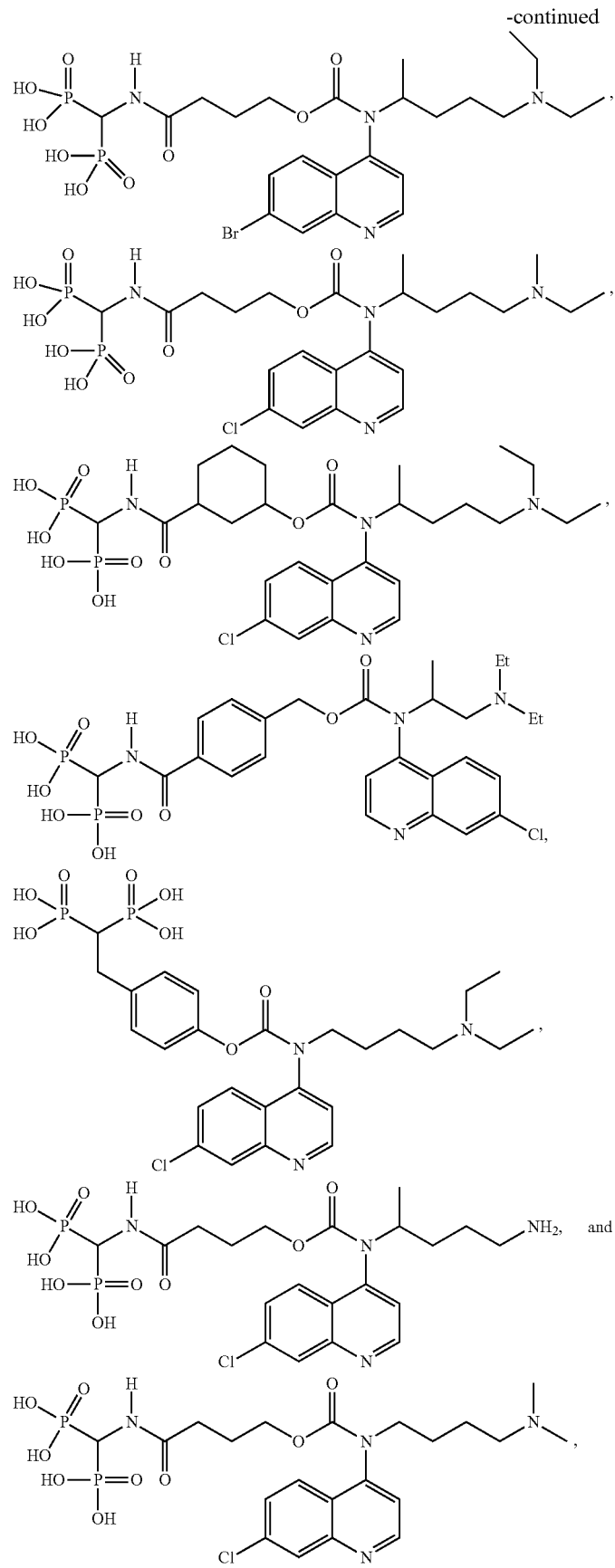

a pharmaceutically acceptable salt thereof, an isomer thereof, or a mixture of isomers thereof.

In one embodiment, the compound is

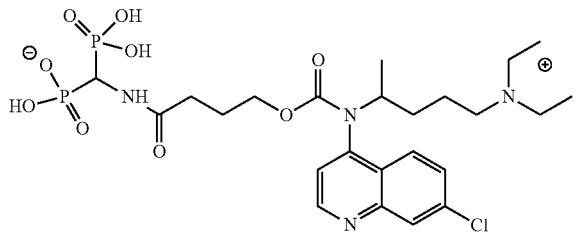

a pharmaceutically acceptable salt thereof, an isomer thereof, or a mixture of isomers thereof.

In one aspect, the invention provides a composition for controlled local delivery of a therapeutic agent to bone, the composition comprising at least one compound comprising a therapeutic agent tethered to a phosphonate moiety via a linker, wherein the therapeutic agent is chloroquine (CQ) or an analogue thereof.

In one embodiment, the compound is selected from the group consisting of: a compound of formula (I), a compound of formula (II), a pharmaceutically acceptable salt thereof; or an isomer thereof; or a mixture of isomers thereof.

In one embodiment, the composition further comprises at least one pharmaceutically acceptable carrier. In one embodiment, the therapeutic agent is controllably released from the compound at a site in need thereof.

In another aspect the invention provides a method of promoting bone formation at a site in need of bone formation in a subject or reducing bone resorption in a subject in need of less bone resorption, or both, the method comprising administering a therapeutically effective amount of a composition comprising at least one compound comprising a therapeutic agent conjugated to a phosphonate moiety via a linker, wherein the therapeutic agent is chloroquine (CQ) or an analogue thereof.

In one embodiment, the at least one compound is a compound selected from the group consisting of a compound of formula (I), a compound of formula (II), a pharmaceutically acceptable salt thereof; or an isomer thereof; or a mixture of isomers thereof.

In another aspect, the invention provides a method of inhibiting inflammation at a site in need thereof, the method comprising administering a therapeutically effective amount of a composition comprising at least one compound comprising a therapeutic agent conjugated to a phosphonate moiety via a linker, wherein the therapeutic agent is chloroquine (CQ) or an analogue thereof.

In one embodiment, the subject has a disease or disorder selected from the group consisting of multiple myeloma, osteoporosis, osteonecrosis, osteomyelitis, osteoarthritis, rheumatoid, psoriatic and other forms of inflammatory arthritis, Paget's disease, bone cancer, cancers metastasized to bone, multiple myeloma, prosthesis loosening, and bone fracture and repair.

In one embodiment, the subject has arthritis.

In one embodiment, the composition further comprises at least one pharmaceutically acceptable carrier.

In one embodiment, the therapeutic agent is controllably released from the compound at the site in need thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A-2B, depicts experimental data demonstrating that BTCQ 1 inhibits OC formation more effectively than CQ and conjugates with bone matrix to inhibit bone resorption. FIG. 2A is a panel of images depicting WT mouse bone marrow (BM) cells. The BM cells were cultured on plastic with M-CSF for 2 days to enrich for OC precursor (OCP) cell differentiation from the plated cells. Then M-CSF and RANKL plus the indicated doses of BTCQ 1 or CQ were added for 3 more days to stimulate the differentiation of the OCPs into OCs. TRAP staining was performed to evaluate OC numbers. FIG. 2B depicts images of bone slices that were incubated for 12 hrs with the indicated doses of CQ or BTCQ 1. The compounds were removed and the bone slices were washed twice. WT mouse BM cells were seeded in the wells with the bone slices and cultured with M-CSF and RANKL for 10 days to generate OCs and stimulate them to form resorption pits on the surfaces of the bone slices. Toludine blue staining was performed to help delineate resorption pits, the areas of which were evaluated. 4 wells/group. *$p<0.05$, **$p<0.01$.

DETAILED DESCRIPTION OF THE INVENTION

Figure 1:
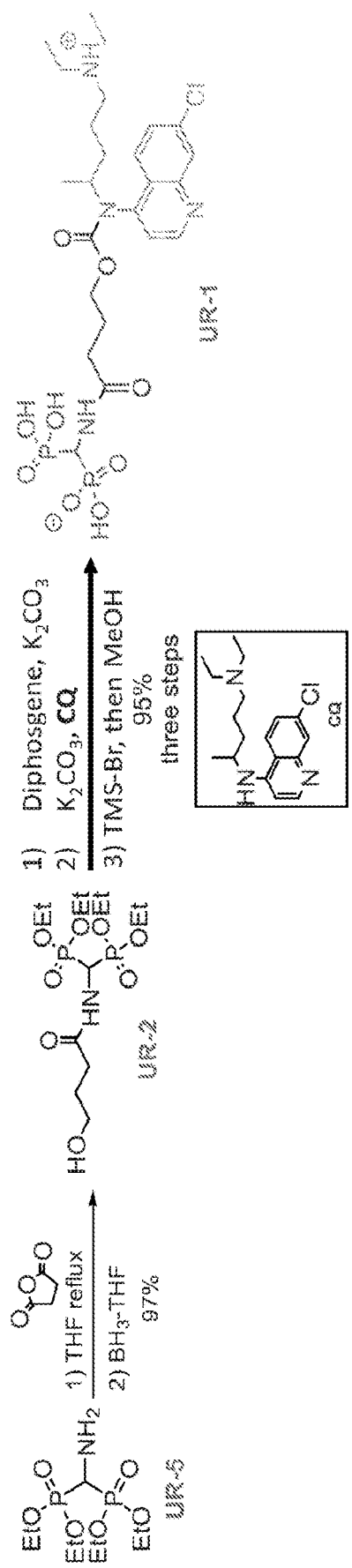
FIG. 1 depicts an exemplary synthetic route for BTCQ 1. Generally, an aminomethylenediphosphonate is converted into an amide, which is then treated with triphosgene to produce a chlorocarbonate. The chlorocarbonate is then reacted with the chloroquine moiety to produce a carbamate, which is then treated with trimethylsilyl bromide to produce BTCQ 1.

This invention includes the unexpected identification of novel Bone-Targeted Chloroquine (BTCQ) analogs that are useful for controlled local delivery of a chloroquine (CQ) to bone. These bone-targeted compounds include a new chemical linker technology designed to conjugate CQ to a non-bioactive bisphosphonate (BP). As demonstrated herein, the compounds of the present invention have been shown to be effective in inhibiting osteoclast (OC) formation. The compounds of the present invention are also effective in reducing inflammation in bone related sites of inflammation. In one embodiment, the compounds of the present invention are effective in reducing inflammation in arthritic joints. The compounds of the invention produce an anti-resorptive effect when used in vivo and inhibit parathyroid hormone (PTH)-induced OC formation at a much lower dose than CQ. Moreover, compounds of the invention have reduced systemic adverse effects than CQ (non-bone-targeted) when administered in vivo. The compounds of the invention are useful in treating patients with Rheumatoid arthritis (RA) and osteoporosis, as well as patients with other bone related disorders characterized by abnormal bone metabolism, such as cancer-bone metastasis, and osteoarthritis. Thus, the present invention also includes compositions and methods useful for the treatment of bone related disorders.

In part, the present invention provides a new chemical approach to link certain drugs to a bisphosphonate residue for a bone-targeting purpose, in which the drug is released from the conjugates on bone, allowing for a greater delivery of the drug to the bone compartment and a greater systemic safety of the conjugate than dosing the free drug component of the conjugate. Safety of the bisphosphonate component will generally be enhanced due to its inert bioactivity or short term circulation in the blood and the low dose that is administered. The present invention also provides in part a new mechanism of action of CQ analogs, an anti-resorptive effect in humans, which to date has not been studied.

The chemical attachment points and other chemical variants unique to the compounds of the invention may be modified in order to adjust the payload release rate, as would be understood by one of ordinary skill in the art. In some embodiments, the compound is comprised of a non-cleavable linker, and the compound has a bioactivity at least the same as the inherent pharmacological activity of the parent CQ.

The present invention also includes novel methods of promoting bone formation at a site in need of bone formation in a subject or reducing bone resorption in a subject in need of less bone resorption, or both. In one embodiment, the subject has osteoporosis, osteonecrosis, osteomyelitis, osteoarthritis, rheumatoid, psoriatic and other forms of inflammatory arthritis, Paget's disease, bone cancer, cancer metastatic to bone, multiple myeloma, prosthesis loosening, and bone fracture and repair.

The present invention also includes novel methods of reducing inflammation at a site in need of anti-inflammatory activity in a subject. In one embodiment, the invention provides a method of reducing inflammation in joints. In one embodiment, the invention provides a method of reducing inflammation in arthritic joints. In one embodiment, the invention provides a method for reducing inflammation in inflamed joints of patients with inflammatory arthitides.

The present invention also includes a composition for controlled local delivery of a therapeutic agent to bone, comprising at least one compound comprising a therapeutic agent conjugated to a phosphonate moiety via a linker. In one embodiment, the therapeutic agent is CQ or an analogue thereof. The present invention also includes a composition comprising at least one compound of the invention, wherein the composition optionally further comprises at least one additional therapeutic agent. In one embodiment, the therapeutic agent is controllably released from the compound at the site in need of bone formation.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

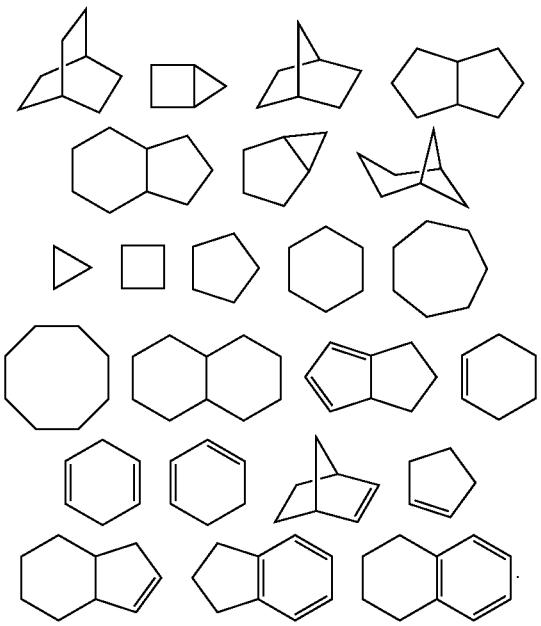

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

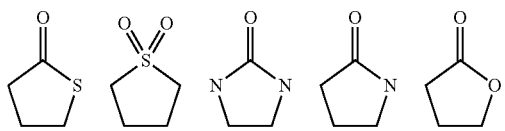

-continued

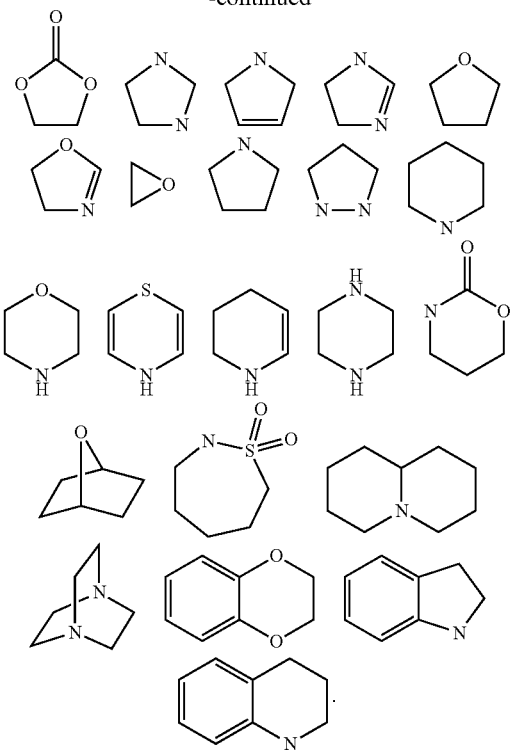

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

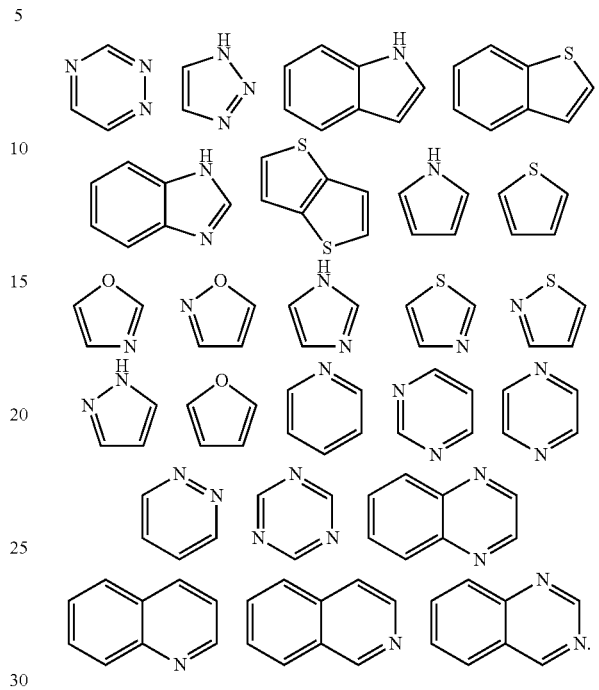

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(═O)$_2$alkyl, —C(═O)NH[substituted or unsubstituted alkyl, or substituted or unsubstituted phenyl], —C(═O)N[H or alkyl]$_2$, —OC(═O)N[substituted or unsubstituted alkyl]$_2$, —NHC(═O)NH [substituted or unsubstituted alkyl, or substituted or unsubstituted phenyl], —NHC(═O)alkyl, —N[substituted or unsubstituted alkyl]C(═O)[substituted or unsubstituted alkyl], —NHC(═O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, OCH$_2$CF$_3$, —S(═O)$_2$—CH$_3$, —C(═O)NH$_2$, —C(═O)—NHCH$_3$, —NHC(═O)NHCH$_3$, —C(═O)CH$_3$, —ON(O)$_2$, and —C(═O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, the term "analogue" refers to a molecule that is not identical, but has analogous functional or structural features.

As used herein, the terms "chloroquine" and "Aralen," which may be used interchangeably, refer to 7-chloro-4-[[4-(diethylamino)-1-methylbutyl]amino] quinoline phosphate (1:2).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is partly based on the discovery that CQ can be targeted to the bone by linking CQ to a high bone affinity, pharmacologically-inert bisphosphonate (IBP) using a degradable chemical linker.

In one embodiment, the invention provides novel Bone-Targeted Chloroquine (BTCQ) analogs that are useful for controlled local delivery of CQ to bone.

Compounds Useful within the Invention

In one aspect, the present invention includes a compound comprising a therapeutic agent conjugated to a phosphonate moiety via a linker, wherein the therapeutic agent is CQ or an analogue thereof. As used herein, the term "conjugate" refers to a compound comprising a therapeutic agent conjugated or attached to a phosphonate moiety via a linker.

Any suitable linker may be used in the invention, as would be understood by one ordinary skill in the art. The linkers may be comprised of any of a variety of functional groups including an amide, ester, ether, thioether, carbamate, urea, amine or other linkage. In some embodiments, the linker comprises a cleavable bond, e.g. a bond that is unstable and/or is cleaved upon changes in certain intracellular parameters (e.g., pH or redox potential). In one embodiment, the linker is cleaved due to acidic hydrolysis. In another embodiment, the linker is cleaved enzymatically, such as by a protease. In another embodiment, the linker is cleaved due to both acidic hydrolysis and enzymatically. In some embodiments, the linker is non-cleavable. For example, it may be desirable to prevent the release of CQ from the conjugate when the conjugate itself possesses desirable bioactivity. As would be understood by one of ordinary skill in the art, the stability of the bond between the linker and the bisphosphonate group and between the linker and the CQ molecule influences how slowly or rapidly each respective bond is cleaved in a particular environment, thereby influencing how slowly or rapidly CQ may be released from the conjugate. In one embodiment, CQ is released slowly from the conjugate. In another embodiment, CQ is released rapidly from the conjugate. In a non-limiting example, the linker is bonded to the CQ molecule and/or the bisphosphonate via a functional group on the linker that provides a more stable bond, and therefore reduces the rate at which CQ is released from the conjugate. In another non-limiting example, the linker may be bonded to the CQ molecule and/or the bisphosphonate via a functional group on the linker that provides a more labile or less stable bond, and therefore increases the rate at which CQ is released from the conjugate. Examples of functional groups that provide a more stable bond include an amide. Examples of functional groups that provide a more labile bond or a less stable or unstable bond include a carbonate group or a carbamate group. In one embodiment, the functional group is a carbamate.

In other embodiments, the electronics of the linker may contribute to the rate at which the CQ molecule is released from the conjugate. In one aspect, the reactivity of compounds of the invention is designed to be tunable to allow for the preparation of sufficiently stable conjugates which will still release CQ efficiently once targeted to bone due to the lower pH in the bone matrix. The high kinetic affinity of bisphosphonates for bone allows for transport to bone to be accomplished without significant degradation of the conjugate and release of the CQ systemically.

In one embodiment, the linker is aliphatic. In another embodiment, the linker comprises an aromatic ring. Non-limiting examples of aromatic rings include an aryl group or a heteroaryl group. In one embodiment, the aryl group is a phenyl group. In some embodiments, the aromatic ring is substituted. In one embodiment, the linker is a phenyl carbamate. As would be understood by one of ordinary skill in the art, the substituents on the aromatic ring may be selected in order to modify the electronic character of the substituted aromatic ring. For example, electron withdrawing groups may be added to the aromatic ring in order to decrease the electron density of the ring, while electron donating groups may be added in order to increase the electron density of the ring. In some embodiments, altering the electronic character of the ring may be used to modulate the reactivity of the linker, thereby influencing the rate of cleavage between the linker and CQ and thus delivery of the CQ warhead to the desired site.

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), a pharmaceutically acceptable salt thereof, an isomer thereof, or a mixture of isomers thereof:

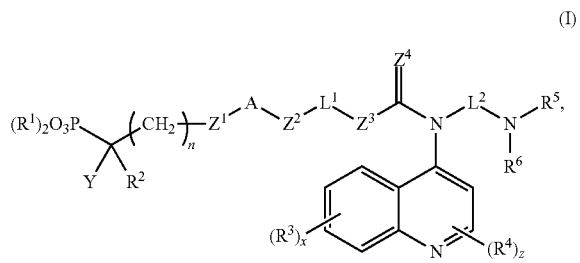

(I)

wherein in formula (I):

each occurrence of $R^1$ is independently selected from the group consisting of hydrogen and alkyl;

$R^2$ is selected from the group consisting of hydrogen, alkyl, —$OR^8$, —$N(R^8)(R^9)$, and halogen;

each occurrence of $R^3$ and $R^4$ is independently selected from the group consisting of alkyl, haloalkyl, heteroalkyl, halogen, —CN, —$NO_2$, —$OR^{16}$, —$SR^{16}$, —$S(=O)R^{16}$, —$S(=O)_2R^{16}$, —$NHS(=O)_2R^{16}$, —$C(=O)R^{16}$, —$OC(=O)R^{16}$, —$CO_2R^{16}$, —$OCO_2R^{16}$, —$CH(R^{16})_2$, —$N(R^{16})_2$, —$C(=O)N(R^{16})_2$, —$OC(=O)N(R^{16})_2$, —$NHC(=O)NH(R^{16})$, —$NHC(=O)R^{16}$, —$NHC(=O)OR^{16}$, —$C(OH)(R^{16})_2$, and —$C(NH_2)(R^{16})_2$, wherein the alkyl, haloalkyl, or heteroalkyl are optionally substituted;

$R^5$, $R^6$, $R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$L^1$ and $L^2$ are each independently selected from the group consisting of a bond, alkyl, aryl, cycloalkyl, alkylaryl, arylalkyl, and alkylcycloalkyl, wherein the alkyl, aryl, cycloalkyl, alkylaryl, arylalkyl or alkylcycloalkyl is optionally substituted with one to four substituents selected from the group consisting of hydroxyl, alkoxy, alkenyl, cycloalkyl, aryl, heteroaryl, halo, cyano and amino;

Y is selected from the group consisting of —$PO(OR^{10})(OR^{11})$, —$PO(R^{10})(OR^{11})$, —$CO_2R^{10}$, and —$SO_3R^{10}$;

$R^{10}$ and $R^{11}$ are each independently selected from the group consisting of hydrogen and alkyl;

$Z^1$ is selected from the group consisting of a bond, $CH_2$ and $NR^{12}$;

A is selected from the group consisting of a bond, $CH_2$, $C(=O)$, $C(=NR^{13})$, and $C(=S)$;

$Z^2$ is selected from the group consisting of a bond, $CH_2$, $NR^{14}$, S, and O;

$Z^3$ is selected from the group consisting of a bond, $CH_2$, $NR^7$, S, and O $Z^4$ is selected from the group consisting of O, $NR^{15}$, and S;

$R^7$, $R^{12}$, $R^{13}$, $R^{14}$, and $R^{15}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

each occurrence of $R^{16}$ is independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

n is an integer from 0 to 10;

x is an integer from 0 to 4; and z is an integer from 0 to 2.

In another aspect, the compound of the invention is a compound of formula (II), a pharmaceutically acceptable salt thereof, an isomer thereof, or a mixture of isomers thereof:

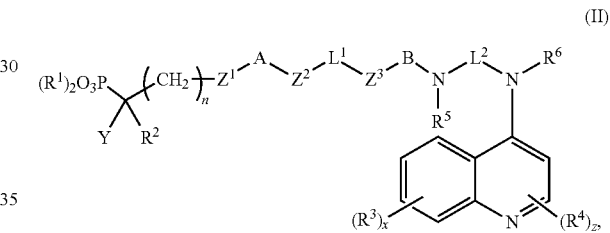

(II)

wherein in formula (II):

each occurrence of $R^1$ is independently selected from the group consisting of hydrogen and alkyl;

$R^2$ is selected from the group consisting of hydrogen, alkyl, —$OR^8$, —$N(R^8)(R^9)$, and halogen;

each occurrence of $R^3$ and $R^4$ is independently selected from the group consisting of alkyl, haloalkyl, heteroalkyl, halogen, —CN, —$NO_2$, —$OR^{16}$, —$SR^{16}$, —$S(=O)R^{16}$, —$S(=O)_2R^{16}$, —$NHS(=O)_2R^{16}$, —$C(=O)R^{16}$, —$OC(=O)R^{16}$, —$CO_2R^{16}$, —$OCO_2R^{16}$, —$CH(R^{16})_2$, —$N(R^{16})_2$, —$C(=O)N(R^{16})_2$, —$OC(=O)N(R^{16})_2$, —$NHC(=O)NH(R^{16})$, —$NHC(=O)R^{16}$, —$NHC(=O)OR^{16}$, —$C(OH)(R^{16})_2$, and —$C(NH_2)(R^{16})_2$, wherein the alkyl, haloalkyl, or heteroalkyl are optionally substituted;

$R^5$, $R^6$, $R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$L^1$ and $L^2$ are each independently selected from the group consisting of a bond, alkyl, aryl, cycloalkyl, alkylaryl, arylalkyl, and alkylcycloalkyl, wherein the alkyl, aryl, cycloalkyl, alkylaryl, alkylaryl, or alkylcycloalkyl is optionally substituted with one to four substituents selected from the group consisting of hydroxyl, alkoxy, alkenyl, cycloalkyl, aryl, heteroaryl, halo, cyano and amino;

Y is selected from the group consisting of —$PO(OR^{10})(OR^{11})$, —$PO(R^{10})(OR^{11})$, —$CO_2R^{10}$, and —$SO_3R^{10}$;

$R^{10}$ and $R^{11}$ are each independently selected from the group consisting of hydrogen and alkyl;

$Z^1$ is selected from the group consisting of a bond, $CH_2$ and $NR^{12}$;

A and B are each independently selected from the group consisting of a bond, $CH_2$, $C(=O)$, $C(=NR^{13})$, and $C(=S)$;

$Z^2$ is selected from the group consisting of a bond, $CH_2$, $NR^{14}$, S, and O;

$Z^3$ is selected from the group consisting of a bond, $CH_2$, $NR^7$, S, and O $Z^4$ is selected from the group consisting of O, $NR^{15}$, and S;

$R^7$, $R^{12}$, $R^{14}$, and $R^{15}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

each occurrence of $R^{13}$ and $R^{16}$ is independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

n is an integer from 0 to 10;

x is an integer from 0 to 4; and z is an integer from 0 to 2.

In another aspect, the compound of the invention is a compound of formula (III), a pharmaceutically acceptable salt thereof, an isomer thereof, or a mixture of isomers thereof:

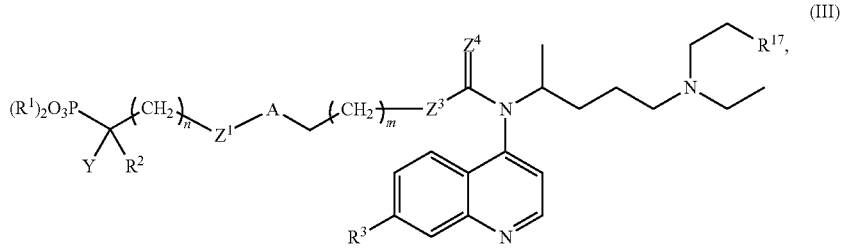

(III)

wherein in formula (III):

each occurrence of $R^1$ is independently selected from the group consisting of hydrogen and alkyl;

$R^2$ is selected from the group consisting of hydrogen, alkyl, $—OR^8$, $—N(R^8)(R^9)$, and halogen;

$R^3$ is selected from the group consisting of halogen, $NO_2$, $—CF_3$, $—OR^{16}$, and $—CH_3$;

Y is selected from the group consisting of $—PO(OR^{10})(OR^{11})$, $—PO(R^{10})(OR^{11})$, $—CO_2R^{10}$, and $—SO_3R^{10}$;

$Z^1$ is selected from the group consisting of $CH_2$ and $NR^{12}$;

A is selected from the group consisting of $CH_2$, $C(=O)$, $C(=NR^{13})$, and $C(=S)$;

$Z^3$ is selected from the group consisting of $CH_2$, $NR^7$, S, and O;

$Z^4$ is selected from the group consisting of O, $NR^{15}$, and S;

$R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^{10}$ and $R^{11}$ are each independently selected from the group consisting of hydrogen and alkyl;

$R^7$, $R^{12}$, $R^{13}$, $R^{14}$, $R^{15}$, and $R^{16}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^{17}$ is selected from the group consisting of hydrogen, $—OR^{18}$, $—CH_3$, and $—CF_3$;

$R^{18}$ is selected from the group consisting of hydrogen and alkyl, wherein alkyl is optionally substituted with one to four substituents selected from the group consisting of hydroxyl, alkoxy, alkenyl, cycloalkyl, aryl, heteroaryl, halo, cyano and amino;

n is an integer from 0 to 10; and m is an integer from 0 to 10.

In another aspect, the compound of the invention is a compound of formula (IV), a pharmaceutically acceptable salt thereof, an isomer thereof, or a mixture of isomers thereof:

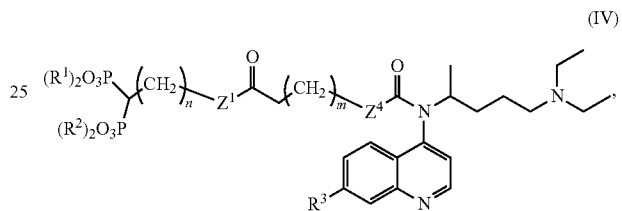

(IV)

wherein in formula (III):

each occurrence of $R^1$ and $R^2$ is independently selected from the group consisting of hydrogen and alkyl;

$R^3$ is selected from the group consisting of halogen, $—CF_3$, $—OR^{16}$, and $—CH_3$;

$Z^1$ is selected from the group consisting of $CH_2$ and $NR^{12}$;

$Z^4$ is selected from the group consisting of O, $NR^{15}$, and S;

$R^{12}$, $R^{15}$, and $R^{16}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

n is an integer from 0 to 10; and m is an integer from 0 to 10.

In one embodiment, each occurrence of $R^1$ is hydrogen. In another embodiment, each occurrence of $R^1$ is alkyl. In another embodiment, one $R^1$ is hydrogen and the other $R^1$ is alkyl.

In one embodiment, $R^2$ is hydrogen. In another embodiment, $R^2$ is $OR^{13}$.

In one embodiment, Y is —PO(OR$^8$)$_2$. In another embodiment, Y is —PO(R$^9$)(OR$^8$). In another embodiment, Y is —CO$_2$R$^8$. In another embodiment, Y is —SO$_3$R$^8$.

In one embodiment, R$^3$ is Cl. In another embodiment, R$^3$ is Br. In another embodiment, R$^3$ is F. In another embodiment, R$^3$ is NO$_2$. In another embodiment, R$^3$ is selected from the group consisting of halogen, —CF$_3$, —OR$^{16}$, and —CH$_3$.

In one embodiment, Z$^1$ is CH$_2$. In another embodiment, Z$^1$ is NR$^{12}$. In another embodiment, Z$^1$ is O. In another embodiment, Z$^1$ is a bond.

In one embodiment, Z$^2$ is CH$_2$. In another embodiment, Z$^2$ is NR$^{14}$. In another embodiment, Z$^2$ is S. In another embodiment, Z$^2$ is O.

In one embodiment, Z$^3$ is CH$_2$. In another embodiment, Z$^3$ is NR$^7$. In another embodiment, Z$^3$ is S. In another embodiment, Z$^3$ is O.

In one embodiment, Z$^4$ is NR$^{15}$. In another embodiment, Z$^4$ is O. In another embodiment, Z$^4$ is S.

In one embodiment, A is C(=O). In another embodiment, A is C(=NR$^{13}$). In another embodiment, A is C(=S). In another embodiment, A is CH$_2$. In another embodiment, A is a bond.

In one embodiment, B is C(=O). In another embodiment, B is CH$_2$. In another embodiment, B is a bond.

In one embodiment, L$^1$ is selected from the group consisting of alkyl, aryl, and alkylaryl. In another embodiment, L$^1$ is a bond. In another embodiment, L$^1$ is C$_1$-C$_5$ alkyl. In one embodiment, L$^1$ is cycloalkyl. In another embodiment, L$^1$ is C$_5$-C$_6$ cycloalkyl. In one embodiment, L$^1$ is aryl. In another embodiment, L$^1$ is phenyl. In one embodiment, L$^1$ is alkylaryl.

In one embodiment, L$^2$ is alkyl substituted with one to four substituents selected from the group consisting of hydroxyl, alkoxy, alkenyl, cycloalkyl, aryl, heteroaryl, halo, cyano and amino. In another embodiment, the alkyl group is a branched alkyl group. In another embodiment, L$^1$ is C$_5$ alkyl.

In one embodiment, R$^5$ is hydrogen. In another embodiment, R$^5$ is alkyl. In another embodiment, R$^5$ is C$_1$-C$_5$ alkyl. In another embodiment, R$^5$ is —CH$_3$. In another embodiment, R$^5$ is C$_2$ alkyl. In another embodiment, R$^5$ is C$_1$-C$_5$ alkyl, wherein the alkyl group is substituted by at least one hydroxyl group.

In one embodiment, R$^6$ is hydrogen. In another embodiment, R$^6$ is alkyl. In another embodiment, R$^6$ is C$_1$-C$_5$ alkyl. In another embodiment, R$^5$ is —CH$_3$. In another embodiment, R$^6$ is C$_2$ alkyl. In another embodiment, R$^6$ is C$_1$-C$_5$ alkyl, wherein the alkyl group is substituted by at least one hydroxyl group.

In one embodiment, R$^7$ is hydrogen.
In one embodiment, R$^8$ is hydrogen.
In one embodiment, R$^9$ is hydrogen.
In one embodiment, R$^{10}$ is hydrogen.
In one embodiment, R$^{11}$ is hydrogen.
In one embodiment, R$^{12}$ is hydrogen.
In one embodiment, R$^{13}$ is hydrogen.
In one embodiment, R$^{14}$ is hydrogen.
In one embodiment, R$^{15}$ is hydrogen.
In one embodiment, R$^{16}$ is hydrogen.

In one embodiment, R$^{17}$ is selected from the group consisting of hydrogen, —OR$^{18}$, —CH$_3$, and —CF$_3$. In another embodiment, R$^{17}$ is hydrogen. In another embodiment, R'$^7$ is —OR$^{18}$.

In one embodiment, R$^{18}$ is hydrogen.

In one embodiment, Z$^2$ and Z$^4$ are each O.

In one embodiment, the compound of the invention is selected from the group consisting of:

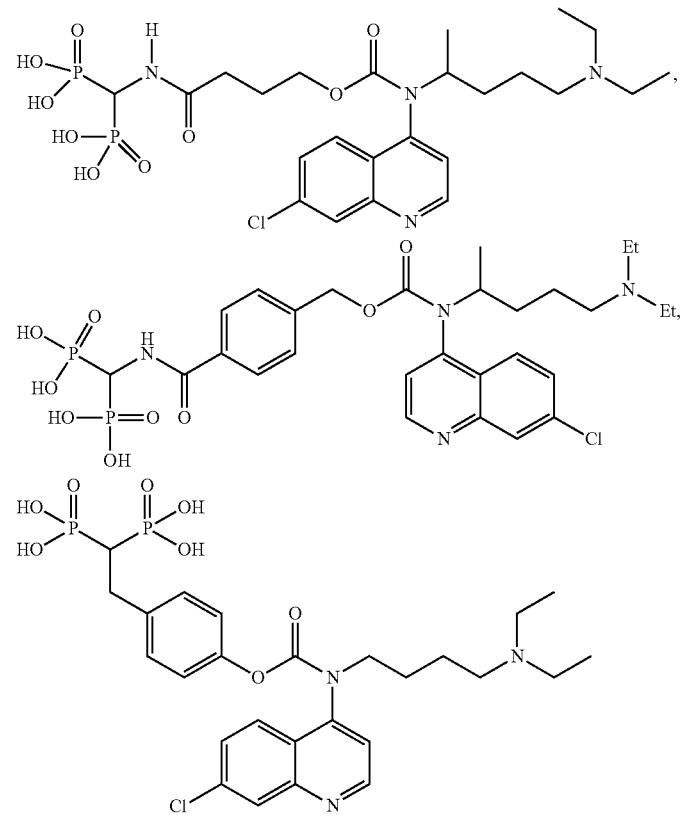

-continued
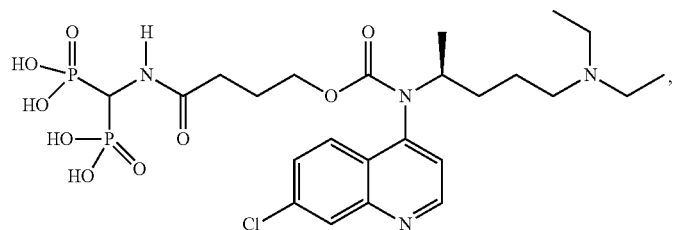
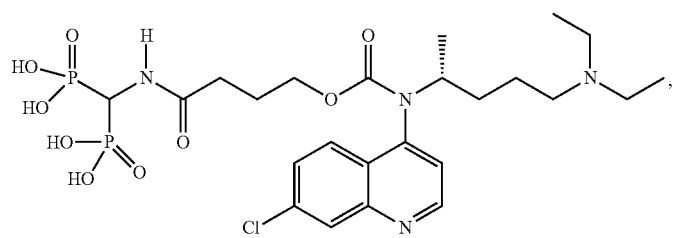
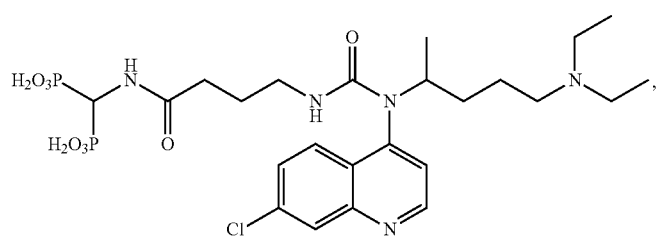
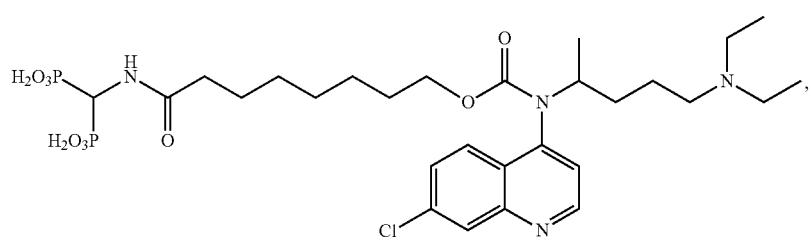
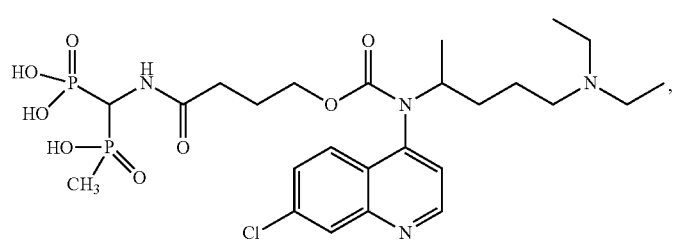
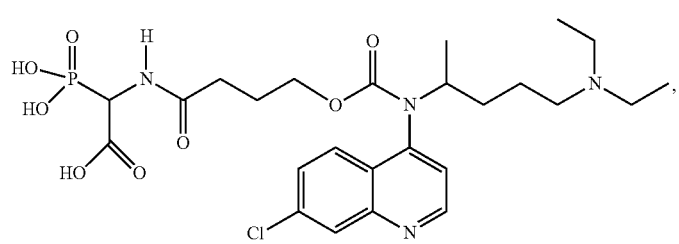
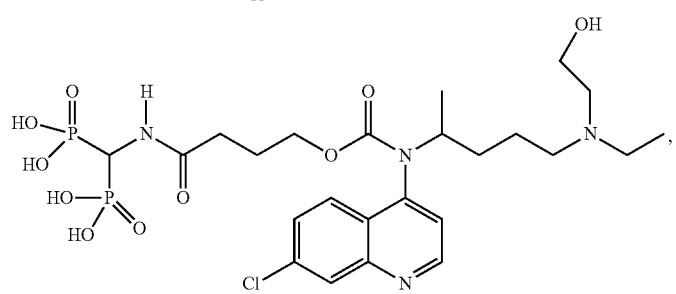

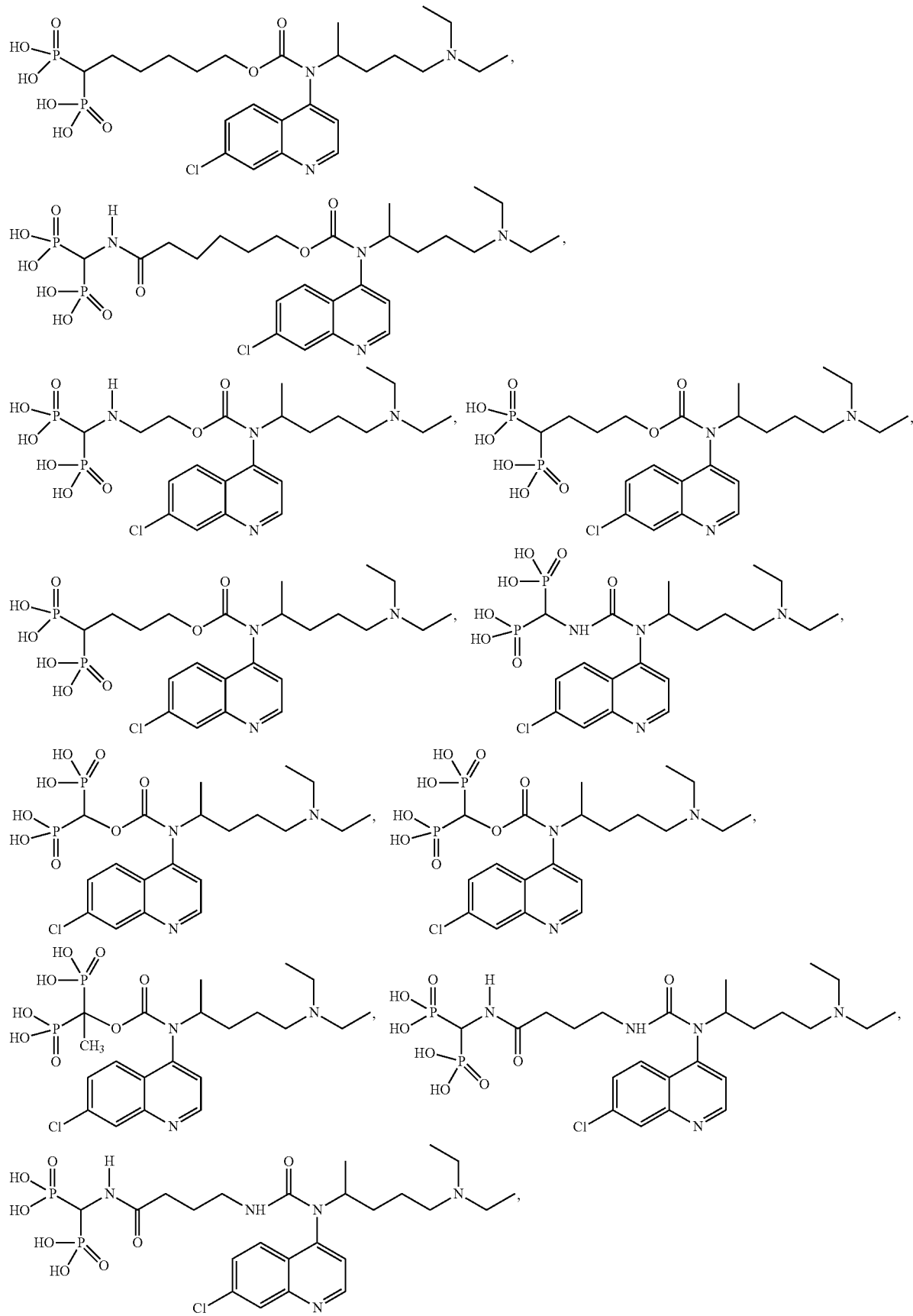

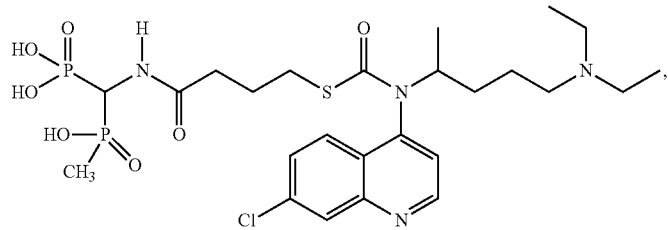
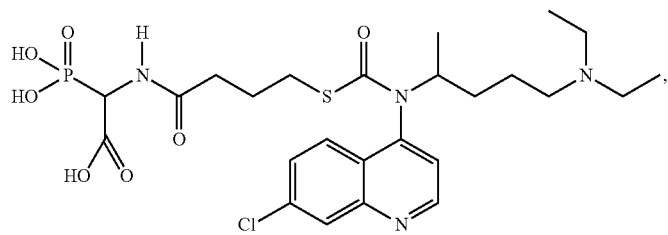
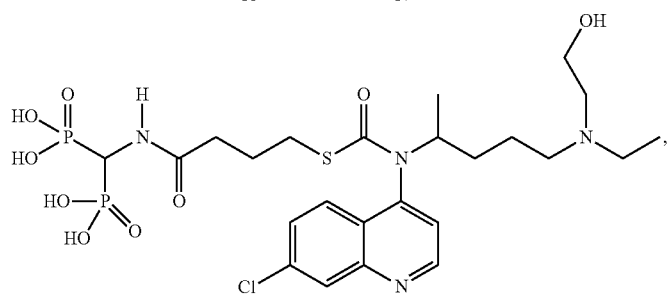
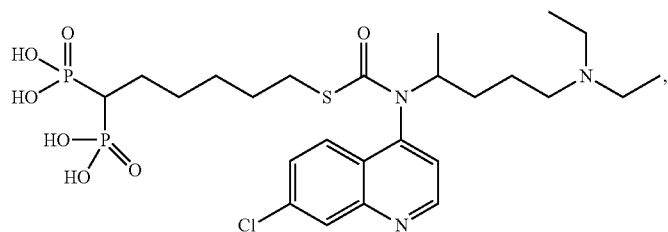
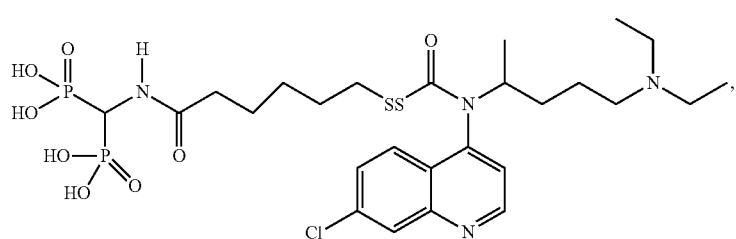
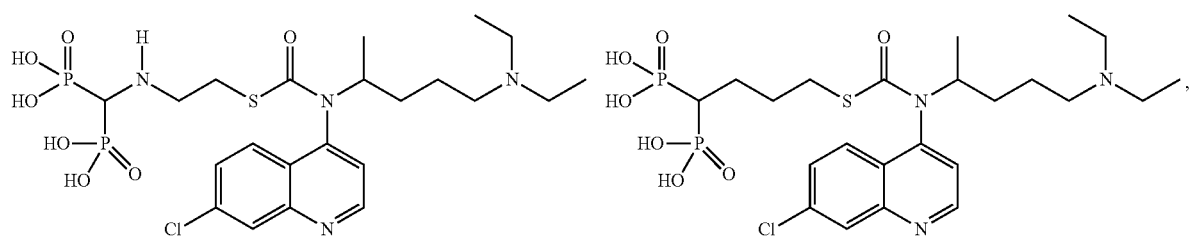
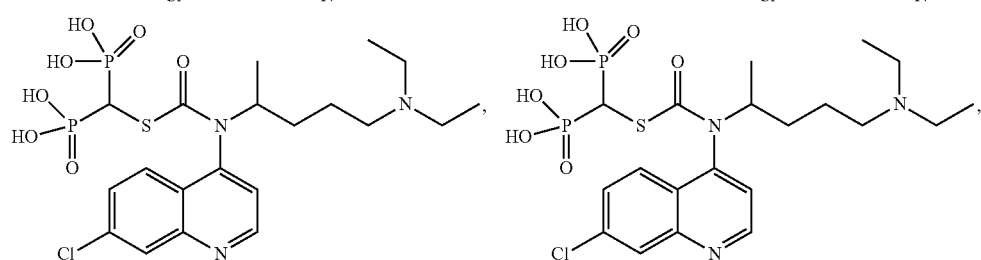

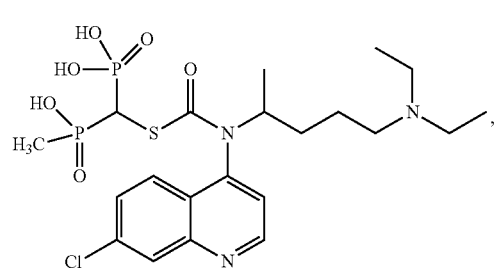
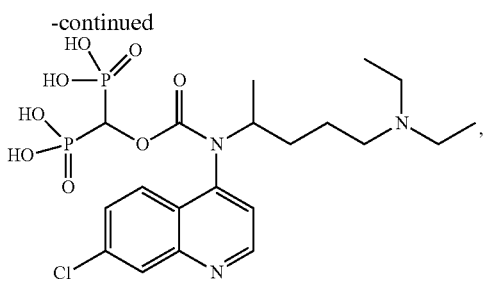
-continued
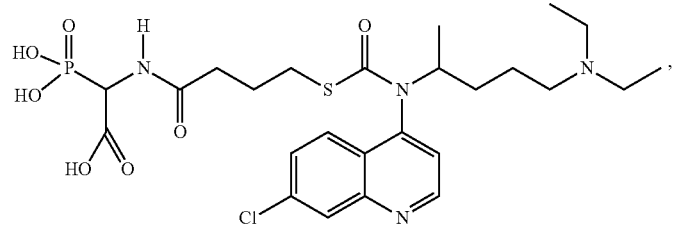
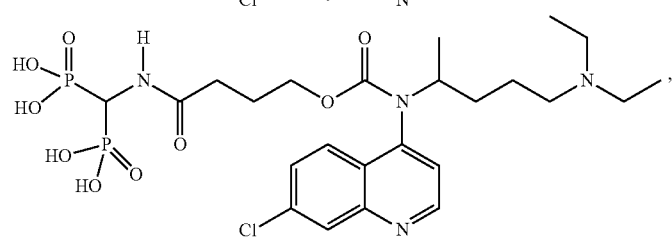
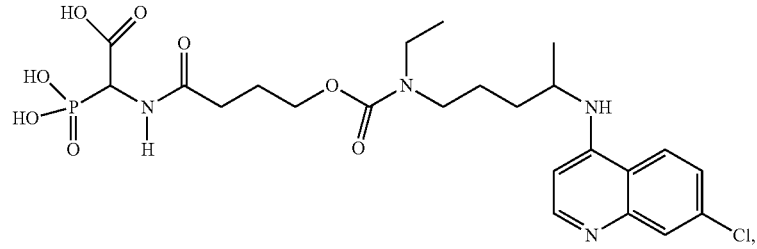
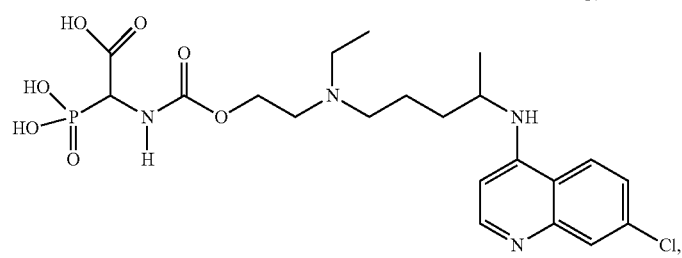
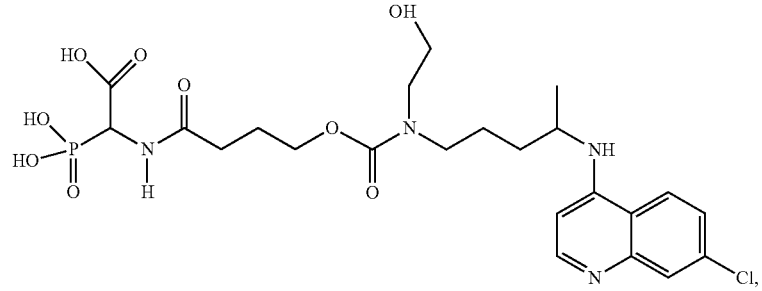
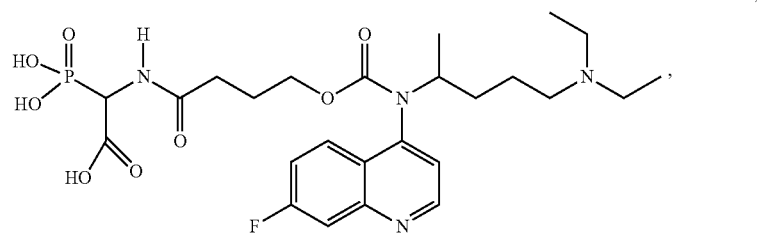

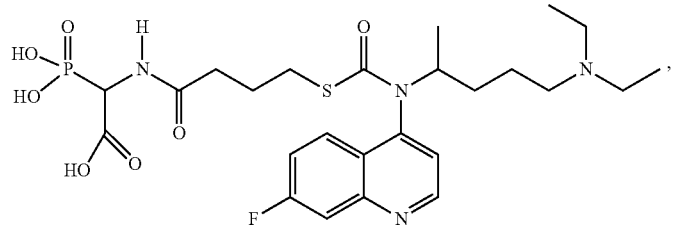
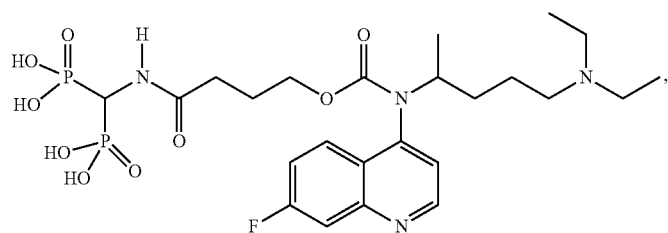
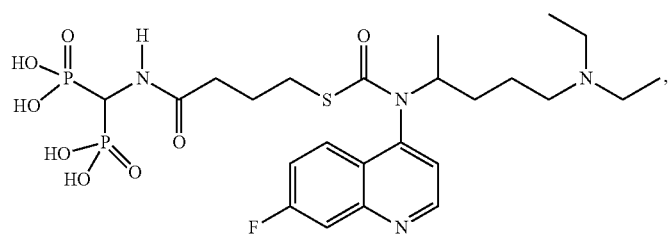
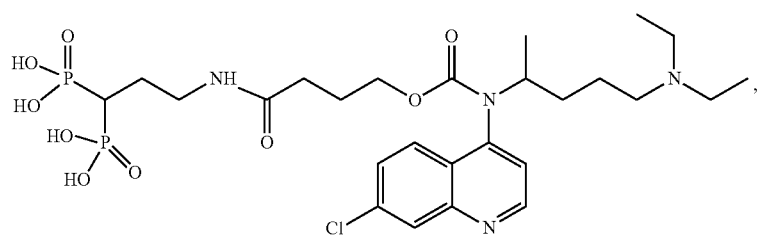
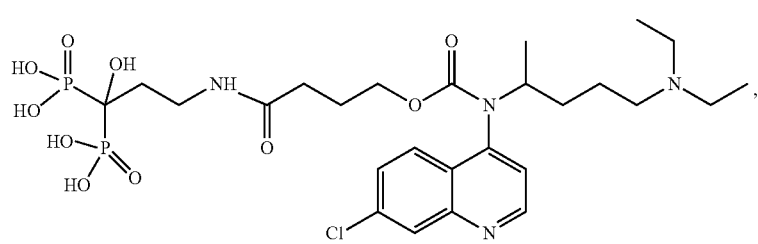 [SMILES: CCN(CC)CCCC(C)N(C(=O)OCCCC(=O)NCCC(O)(P(=O)(O)O)P(=O)(O)O)c1ccnc2cc(Cl)ccc12]
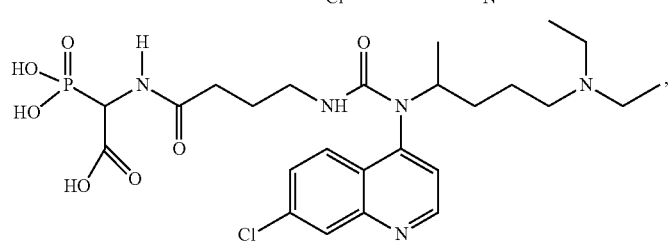
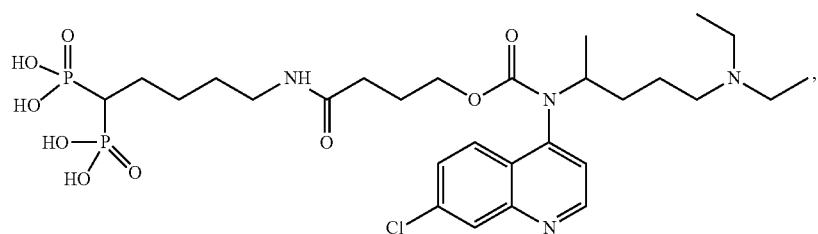

-continued
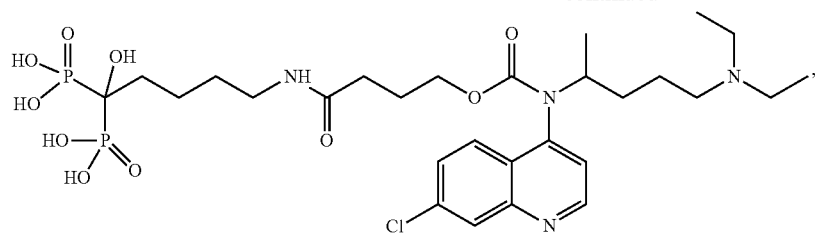
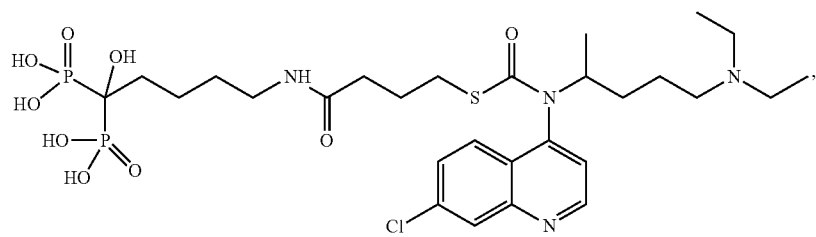
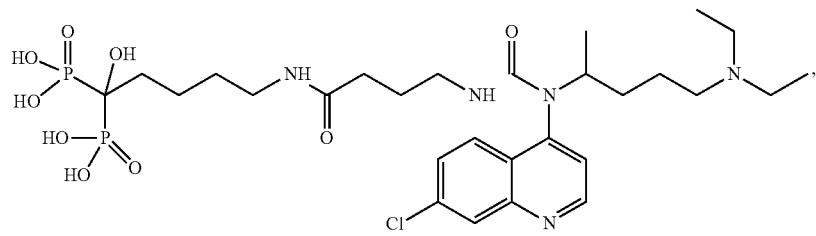
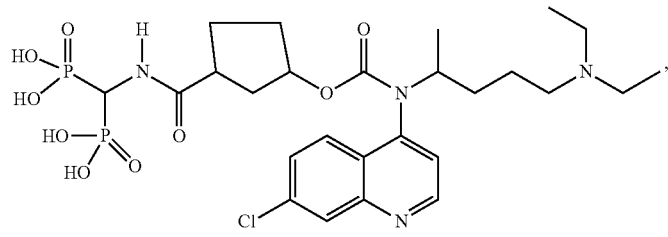
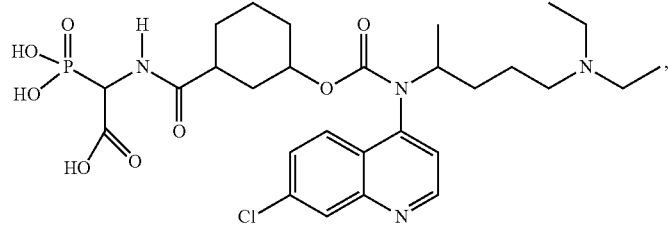
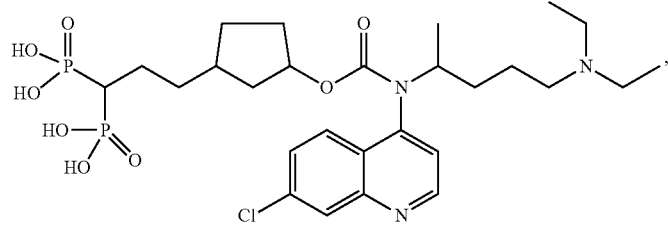
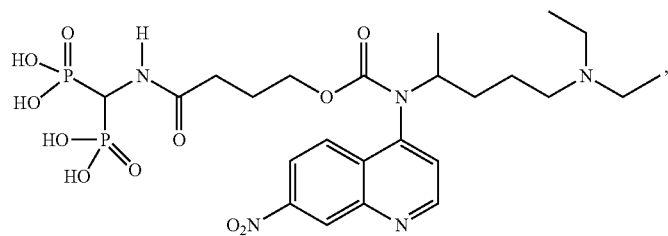

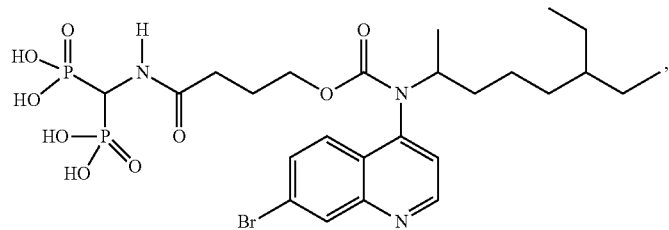
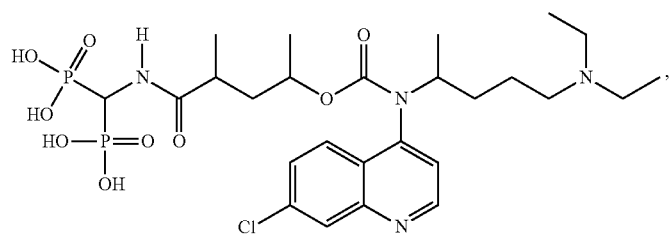
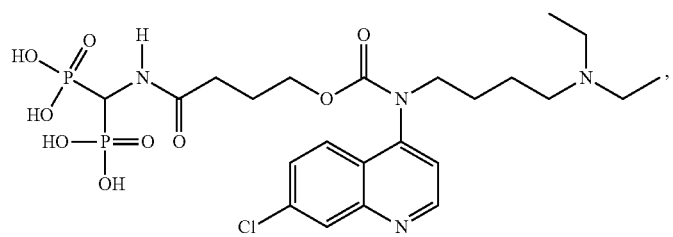
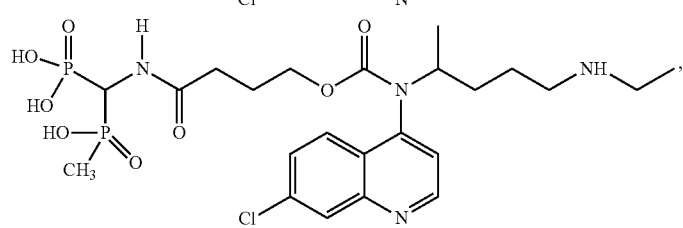
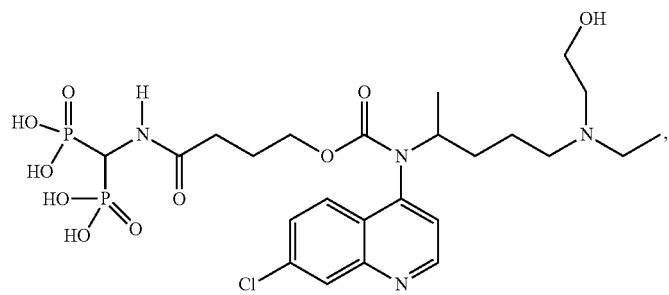
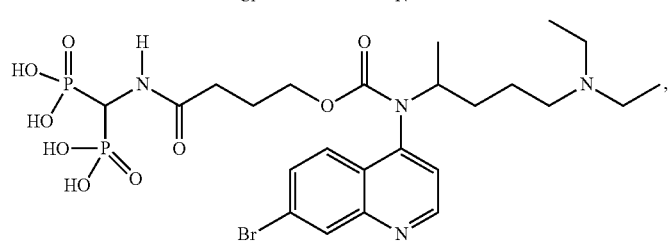
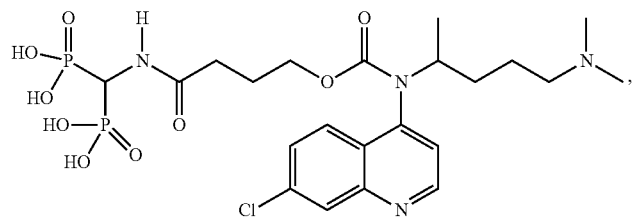

-continued

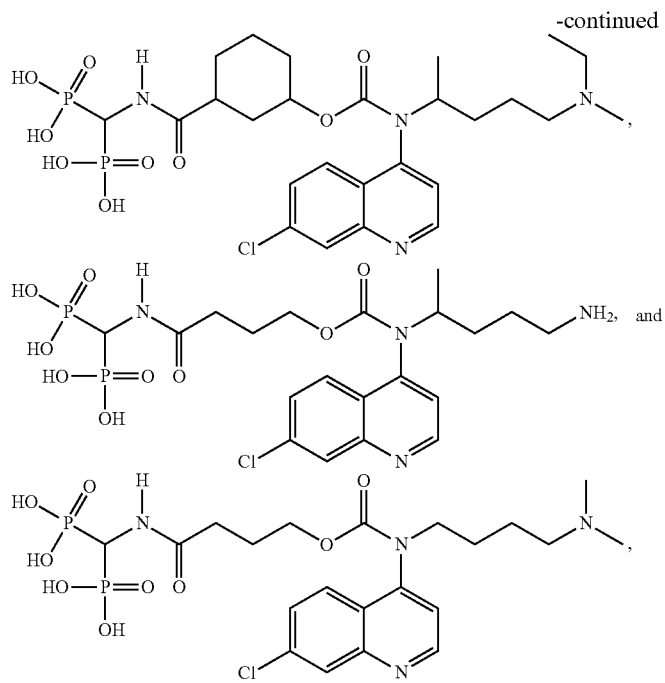

a pharmaceutically acceptable salt thereof, an isomer thereof, or a mixture of isomers thereof.

Preparation of the Compounds of the Invention

Compounds of formulae (I)-(IV) may be prepared by the general schemes described herein, using the synthetic method known by those skilled in the art. The following examples illustrate non-limiting embodiments of the invention.

In a non-limiting embodiment, compounds of the invention may be synthesized by conjugating a phosphonate to the linker region, followed by joining the chloroquine moiety to the linker using any methods known in the art.

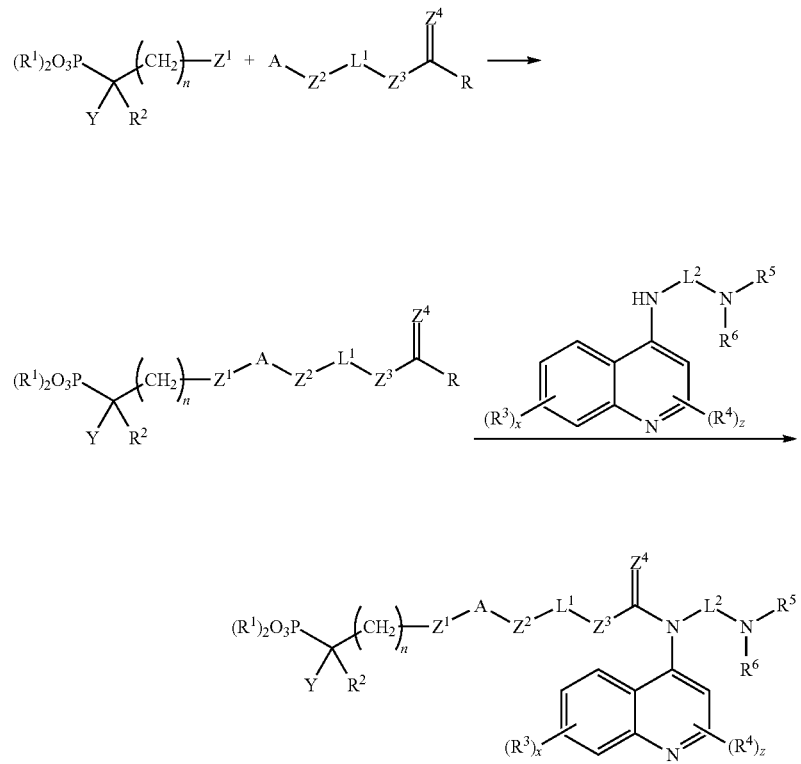

For example, compounds of the invention may be synthesized by conjugating an aminophosphonate to an esterified linker region in order to form an amide using any methods known in the art. The aminophosphonate and the ester can then be conjugated to produce an amide.

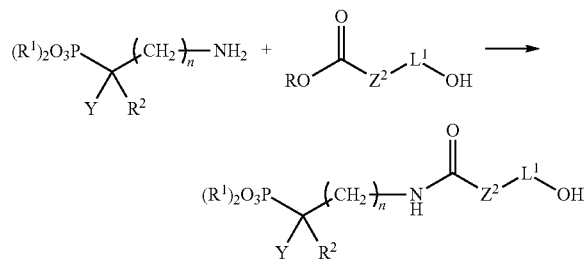

The free alcohol of the amide can be acylated to form a chlorocarbonate, after which the compound can be treated with base and then reacted with a chloroquine moiety to form compounds of the invention.

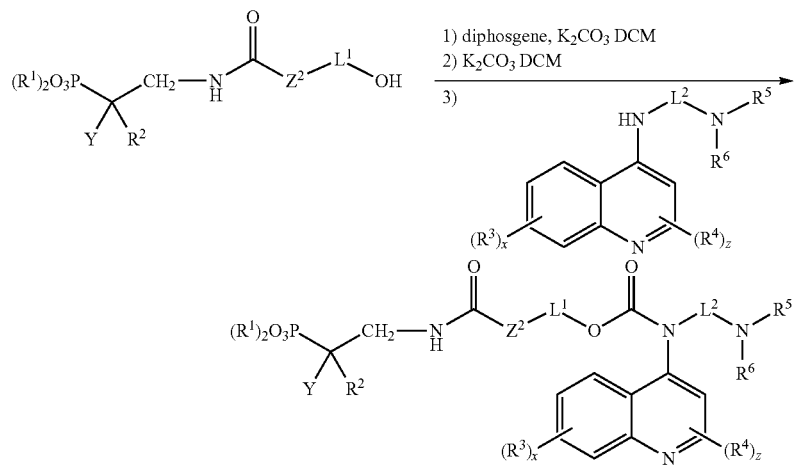

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. In one embodiment, the compounds of the invention include stereoisomers and mixtures of stereoisomers. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$ is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

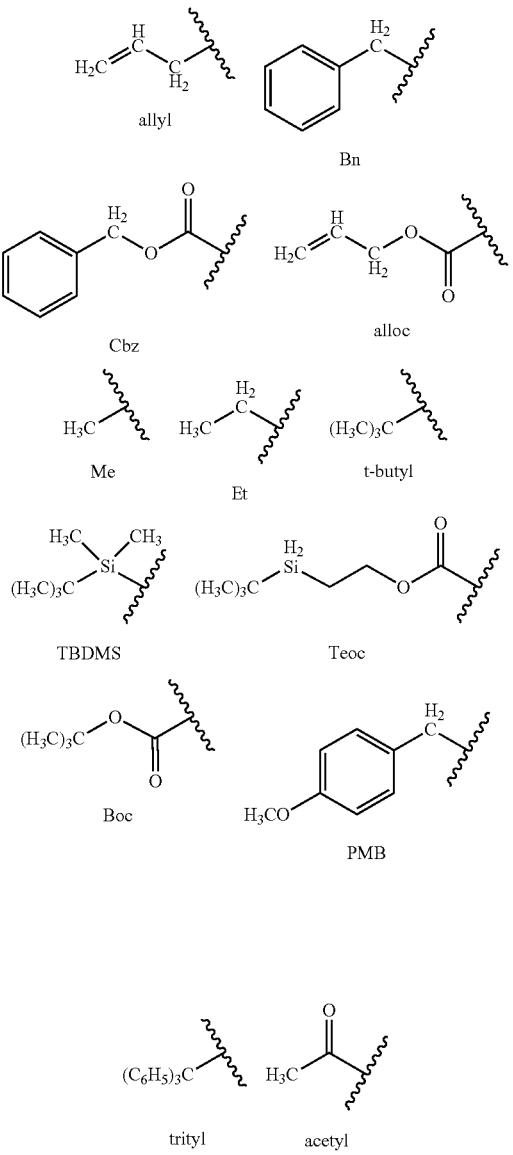

-continued

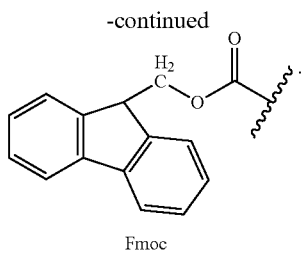

Fmoc

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Therapeutic Methods

The present invention provides a method for promoting or inducing bone formation. In another embodiment, the present invention provides a method for inhibiting osteoclast formation or activation and bone resorption or for promoting or inducing bone formation. In one embodiment, the present invention provides a method for reducing inflammation. In one embodiment, the present invention provides a method for inhibiting bone resorption. In one embodiment, the present invention provides a method for promoting bone formation. The method may be used, for example, as a therapy in treating diseases and disorders characterized by bone loss. In one embodiment, the method is used to treat a subject having arthritis or any related disease. Non-limiting examples of arthritis and related diseases include Adult-onset Still's disease, Ankylosing Spondylitis, Back Pain, Behçet's Disease, Bursitis, Calcium Pyrophosphate Deposition Disease (CPPD), Carpal Tunnel Syndrome, Chondromalacia Patella, Chronic Fatigue Syndrome, Complex Regional Pain Syndrome, Cryopyrin-Associated Periodic Syndromes (CAPS), Degenerative Disc Disease, Developmental-Dysplasia of Hip, Ehlers-Danlos, Familial Mediterranean Fever, Fibromyalgia, Fifth Disease, Giant Cell Arteritis, Gout, Hemochromatosis, Infectious Arthritis, Inflammatory Arthritis, Inflammatory Bowel Disease, Juvenile Arthritis, Juvenile Dermatomyositis (JD), Juvenile Idiopathic Arthritis (JIA), Juvenile Scleroderma, Kawasaki Disease, Lupus, Lyme Disease, Mixed Connective Tissue Disease, Myositis (inc. Polymyositis, Dermatomyositis), Osteoarthritis, Osteoporosis, Pagets, Palindromic Rheumatism, Patellofemoral Pain Syndrome, Pediatric Rheumatic Diseases, Pediatric SLE, Polymyalgia Rheumatica, Pseudogout, Psoriatic Arthritis, Raynaud's Phenomenon, Reactive Arthritis, Reflex Sympathetic Dystrophy, Reiter's Sydrome, Rheumatic Fever, Rheumatism, Rheumatoid Arthritis, Scleroderma, Sjögren's Disease, Spinal Stenosis, Spondyloarthritis, Systemic Juvenile Idiopathic Arthritis, Systemic Lupus Erythematosus, Systemic Lupus Erythematosus in Children & Teens, Systemic Sclerosis, Temporal Arteritis, Tendinitis, Vasculitis, and Wegener's Granulomatosis. In one embodiment, the method is used to treat a subject having osteoporosis. In another embodiment, the method is used to treat a subject at risk for having osteoporosis. In another embodiment, the method is used to treat a subject with bone cancer. In yet another embodiment, the method is used to treat a subject with a fractured bone. The method of the invention provides local delivery of a compound of the invention to a site in need of bone formation or less bone resorption. Thus, the method of the invention should not be construed to be limited solely to treat osteoporosis, but rather should be construed to include any disease or disorder where inhibition of bone resorption or stimulation of bone formation is desired and beneficial for the subject, including for example, osteoporosis, osteonecrosis, osteomyelitis, osteoarthritis, rheumatoid arthritis, psoriatic and other forms of inflammatory arthritis, Paget's disease, bone cancer metastatic to bone, multiple myeloma, prosthesis loosening, and bone fracture and repair.

In one aspect, the present invention includes a method of promoting bone formation at a site in need of bone formation in a subject or reducing bone resorption in a subject in need of less bone resorption, or both. In one embodiment, the method includes administering a therapeutically effective amount of a composition comprising at least one compound comprising a therapeutic agent conjugated to a phosphonate moiety via a linker, wherein the therapeutic agent is chloroquine (CQ) or an analogue thereof.

In one embodiment, the composition further comprises at least one pharmaceutically acceptable carrier. In one embodiment, the therapeutic agent is controllably released from the compound at the site in need thereof.

In certain embodiments, the method comprises administering a pharmaceutical composition comprising a compound of the invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical Compositions and Administration

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents include growth factors, hormones, anti-inflammatories, including corticosteroids, and immunosuppressants, proteins (eg. BMPs), and the like.

Controlled- or sustained-release formulations of a pharmaceutical composition of the invention may be made using conventional technology.

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients;

surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

It will be appreciated that a composition of the invention may be administered to a subject either alone, or in conjunction with another therapeutic agent.

The therapeutic and prophylactic methods of the invention thus encompass the use of pharmaceutical compositions comprising a therapeutic agent that induces or promotes bone formation to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 1 µM and 10 µM in a mammal.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Synthesis of BTCQ 1

Synthesis of Amide Alcohol 3

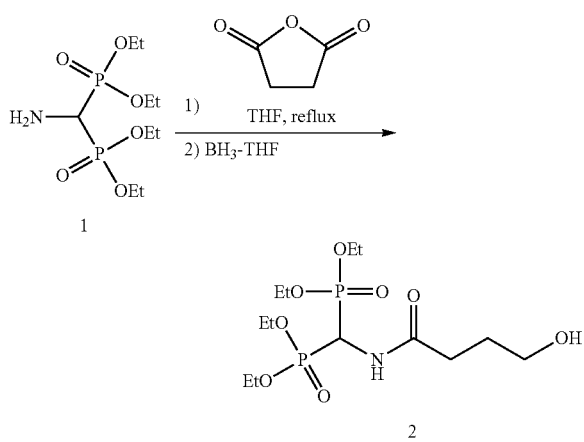

A dry 25 mL round bottom flask under Ar was charged with tetraethyl aminomethylenediphosphonate 1 (400 mg, 1.32 mmol), and succinic anhydride (159 mg, 1.58 mmol) in dry THF (2 mL). The reaction mixture was allowed to reflux for 2.5 hr. The reaction was then cooled down to 0° C. followed by the addition of 1M BH$_3$·THF (2.63 mL, 2.63 mmol) dropwise. After addition, the reaction mixture was warmed to rt for 1.5 hr, and was then cooled back to 0° C. and quenched with CH$_3$OH (10 mL). The volatiles were evaporated in vacuo. The residue dissolved in 10 mL CH$_3$OH and again concentrated in vacuo. This procedure was repeated 3 additional times. Column chromatography of the residue using a CH$_3$OH—CH$_2$Cl$_2$ gradient (5:95 to 10:90) afforded 469 mg (97%) of the amide alcohol 2 as a colorless oil (R$_f$=0.52 (CH$_3$OH—CH$_2$Cl$_2$, 1:9), visualized with KMnO$_4$) having $^1$H NMR (500 MHz, CDCl$_3$) δ 6.21 (d, J=10 Hz, 1H), 5.08-5.00 (m, 1H), 4.20 (m, 8H), 3.71 (q, 2H), 2.46 (t, J=10 Hz, 2H), 2.39 (s, 1H), 1.91 (m, 2H), 1.32-1.35 (m, 12H); $^{13}$C NMR (400 MHz, CDCl$_3$) δ 172.89, 63.44, 61.07, 43.15 (t), 32.44, 28.33, 16.13; $^{31}$P NMR (400 MHz, CDCl$_3$) δ 13.17; MS (ESI) m/z (M+Na$^+$) 412.4.

Synthesis of BTCQ 1

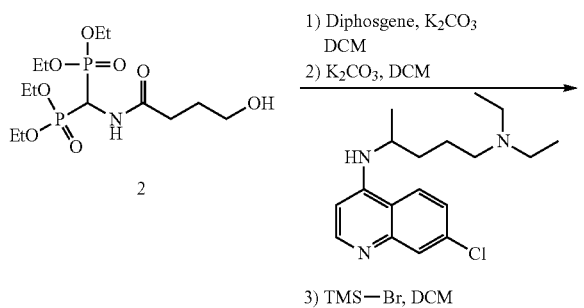

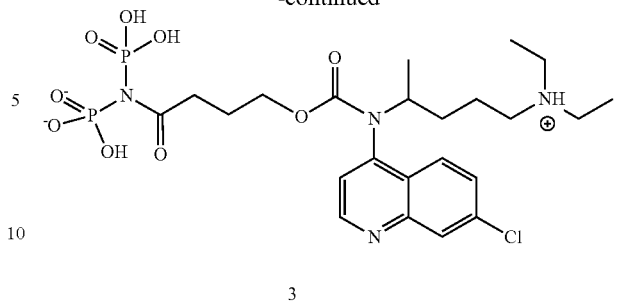

A dry 10 mL round bottom flask under Ar at 0° C. was charged with K$_2$CO$_3$ (138.2 mg, 1 mmol) and diphosgene (79.2 mg, 0.4 mmol) in dry THF (1.5 mL). Alcohol 2 (78 mg, 0.2 mmol) was added dropwise into the reaction mixture. After stirring at 0° C. for 2 hr, the reaction mixture was filtered and the filtrate was extracted with 1M HCl solution (5 mL). The aqueous extract was washed with CH$_2$Cl$_2$ (3×5 mL). The combined organic phases were washed with brine, dried over Na$_2$SO$_4$ and concentrated in vacuo. The resulting residue was placed under high vacuum for an additional 30 min to obtain the resulting chloroformate as light yellow oil (92 mg).

The light yellow oily chloroformate (92 mg, ~0.2 mmol) was dissolved in 0.3 mL CH$_2$Cl$_2$ and added to a mixture of K$_2$CO$_3$ (138.2 mg, 1 mmol) and chloroquine (CQ) (63.8 mg, 0.2 mmol) in dry CH$_2$Cl$_2$ (0.8 mL) at 0° C. under Ar. After being stirred for 1.5 hr at 0° C., the reaction mixture was filtered and the solids washed with 3 mL dry CH$_2$Cl$_2$. The filtrate was transferred to a dry 25 mL round bottom flask under Ar at 0° C. followed by dropwise addition of TMS-Br (122.5 mg, 0.8 mmol). After 20 min, the reaction was allowed to warm to rt for 24 hr. The volatiles were evaporated in vacuo. The residue was dissolved in CH$_3$OH (8 mL) and then concentrated in vacuo. This procedure was repeated 4 additional times to obtain dark brown oil. The resulting oil was dissolved in EtOH (1 mL) followed by addition to 10 mL of Et$_2$O resulting in formation of a brownish-white precipitate. The solid was isolated by filtration and dried under high vacuum overnight affording 148 mg (90-100%) of 3 (BTCQ 1) (CH$_3$OH—H$_2$O solvate) a white solid having $^1$H NMR (500 MHz, D$_2$O) δ 8.25 (s, 1H), 8.18 (d, J=5 Hz, 1H), 7.79 (1H), 7.59 (d, J=10 Hz, 1H), 6.80 (s, 1H), 4.44-4.40 (m, 1H), 4.09 (m, 1H), 3.72 (t, J=5 Hz, 2H), 3.15 (m, 6H), 2.40 (m, 2H), 2.01 (t, J=5 Hz, 2H), 1.81 (m, 4H), 1.36 (d, J=5 Hz, 3H), 1.20 (m, 6H); $^{13}$C NMR (400 MHz, D$_2$O) δ 177.67, 174.86, 155.36, 142.07, 139.17, 138.11, 127.18, 124.01, 119.02, 115.18, 98.39, 60.74, 51.06, 47.23, 32.27, 31.81, 30.26, 27.53, 20.15, 18.68, 17.38, 8.09; $^{31}$P NMR (400 MHz, D$_2$O) δ −1.85; MS (ESI) m/z (M+H$^+$) 623.0, 625.0.

Synthesis of BTCQ 1 Triethylamine Salt

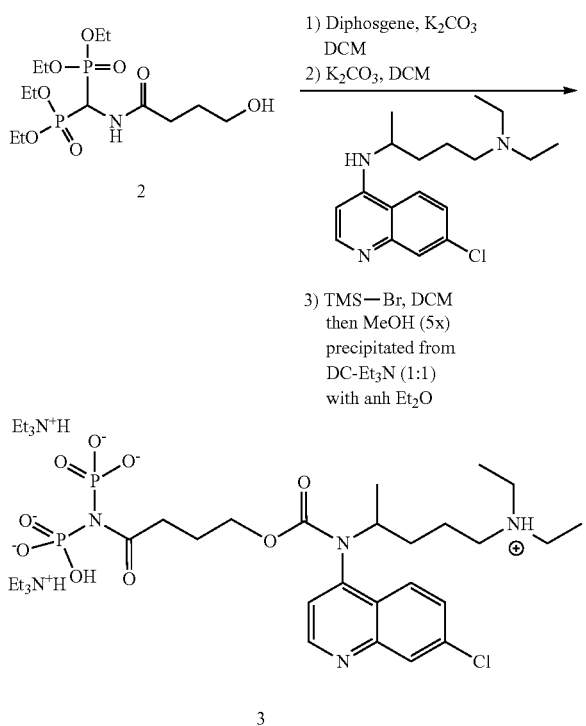

A dry 250 mL round bottom flask under Ar at 0° C. was charged with $K_2CO_3$ (7.36 g, 53.3 mmol) and diphosgene (5.2 g, 26.6 mmol) in dry $CH_2Cl_2$ (80 mL). Alcohol 2 (6.91 g, 17.76 mmol) was added dropwise into the reaction mixture. After stirring at 0° C. for 2 hr, the reaction mixture was filtered and the filtrate was extracted with 1M HCl solution (50 mL). The aqueous phase was extracted with $CH_2Cl_2$ (3×50 mL). The combined organic phases were washed with brine, dried over $Na_2SO_4$ and concentrated in vacuo. The resulting residue was placed under high vacuum for an additional 1 hr to obtain 8.16 g (~100%) of the derived chloroformate as light yellow oil.

The light yellow oily chloroformate (8.16 g~17.76 mmol) was dissolved in 10 mL $CH_2Cl_2$, and added into a mixture of $K_2CO_3$ (7.6 g, 53.3 mmol) and chloroquine (CQ) (5.66 g, 17.76 mmol) in dry $CH_2Cl_2$ (60 mL) at 0° C. under Ar. After stirring 1.5 hr at 0° C., the reaction mixture was filtered and the solids were washed with 15 mL of dry $CH_2Cl_2$. The filtrate was transferred to a dry 250 mL round bottom flask under Ar at 0° C. followed by dropwise addition of TMS-Br (16.31 g, 160.56 mmol). After 20 min, the reaction was allowed to warm to rt and stir for 24 hr. The volatiles were evaporated in vacuo. The residue was dissolved in $CH_3OH$ (100 mL) and then concentrated in vacuo. This procedure was repeated 4 additional times to obtain dark brown oil. The resulting oil was dissolved in $CH_2Cl_2$ (250 mL) and $Et_3N$ (250 mL) followed by addition to 1 L of $Et_2O$ resulting in formation of a brownish-white precipitate. The solid was isolated by filtration and dried under high vacuum overnight affording 14.2 g of 4 (BTCQ 1 triethylamine salt) (86%) as a white solid having $^1H$ NMR (500 MHz, $D_2O$) δ 8.25 (s, 1H), 8.18 (d, J=5 Hz, 1H), 7.79 (s, 1H), 7.59 (d, J=10 Hz, 1H), 6.80 (s, 1H), 4.44-4.40 (m, 1H), 4.09 (m, 1H), 3.72 (t, J=5 Hz, 2H), 3.15 (m, 6H), 2.40 (m, 2H), 2.01 (t, J=5 Hz, 2H), 1.81 (m, 4H), 1.36 (d, J=5 Hz, 3H), 1.20 (m, 6H); $^{13}C$ NMR (400 MHz, $D_2O$) δ 177.67, 174.86, 155.36, 142.07, 139.17, 138.11, 127.18, 124.01, 119.02, 115.18, 98.39, 60.74, 51.06, 47.23, 32.27, 31.81, 30.26, 27.53, 20.15, 18.68, 17.38, 8.09; $^{31}P$ NMR (400 MHz, $D_2O$) δ −1.85; MS (ESI) m/z (M+H$^+$) 623.0, 625.0.

Figure 2:
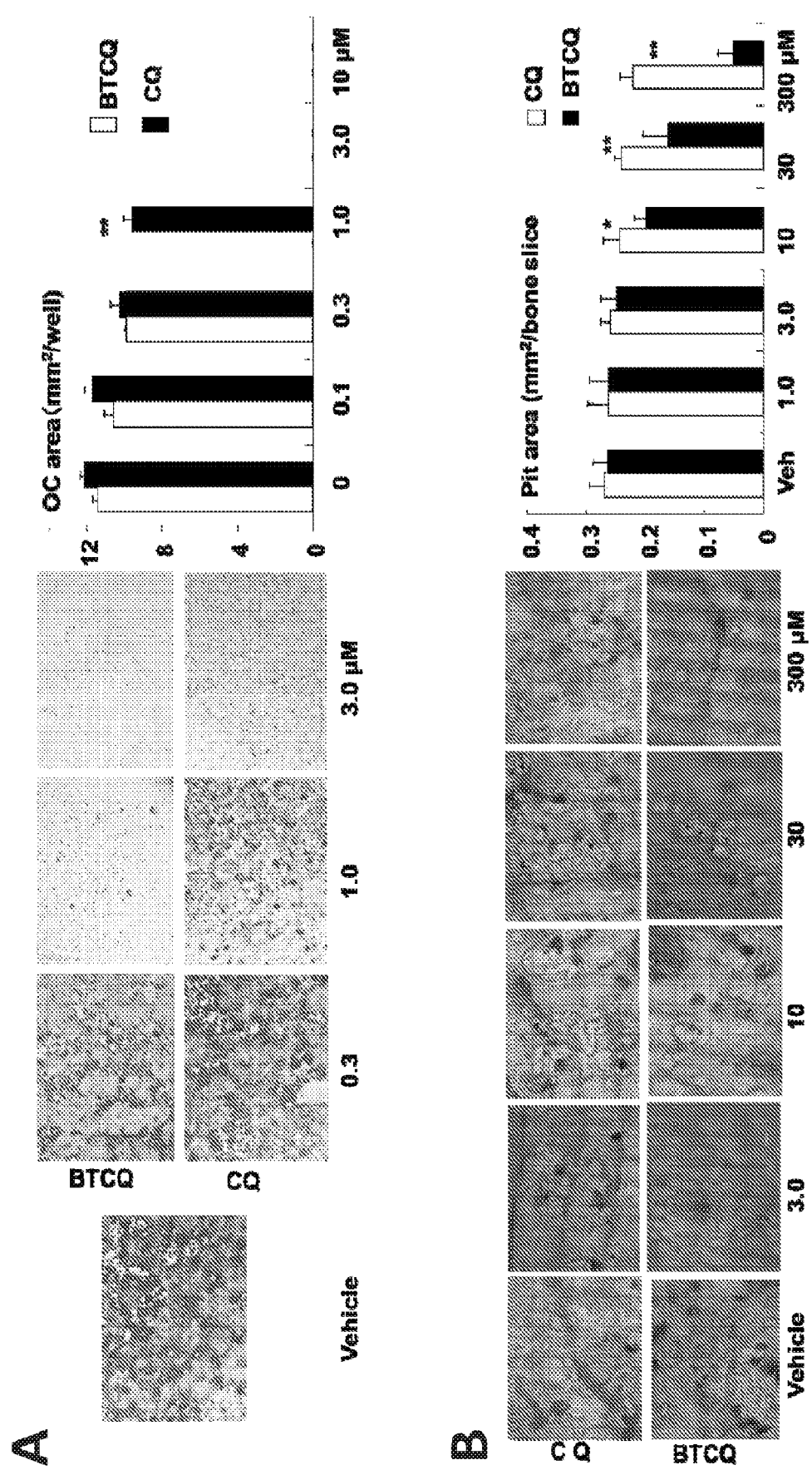
FIG. 2, comprising

Example 2: Development of Bone-Targeted Chloroquine Using Novel Bisphosphonate Prodrug Technology to Inhibit Bone Resorption & Inflammation in Rheumatoid Arthritis It was hypothesized that if CQ could be targeted to bone using compounds, such as bisphosphonates (BPs), which have high affinity for bone (Bagi et al., 2005, Adv Drug Deliv Rev), it could be administered at lower but still effective concentrations and thus side-effects could be reduced or prevented Bone-Targeted Chloroquine (BTCQ) analogs have been generated by linking CQ to a non-bioactive BP using degradable amide linker chemistry (moieties) to determine if the CQ released in bone would have anti-osteoclast efficacy at least equivalent to CQ in standard in vitro OC formation assays. As controls, the effects of the non-bioactive BP that would be released in the bone compartment as well as a non-releasable/non-degradable amide linked conjugate that also comprises a BTCQ and resembled the degradable conjugate were also studied (FIG. 1). In in vitro studies the BTCQ conjugate BTCQ 1 bearing a degradable linker had anti-osteoclast activity equivalent to or better than CQ itself. In a pivotal in vitro study, this BTCQ conjugate and CQ were independently incubated with bone slices for 12 hours after which the bone slices were removed and placed in culture wells with fresh media along with OC precursors. Formation and activity of osteoclasts (OCs) derived from these precursors were significantly reduced on the bone slices pre-incubated with the conjugate, but not on those slices pre-incubated with CQs, consistent with the BT component binding to the bone slices during the 12 hour exposure and the CQ being released and taken up subsequently by OC precursors to inhibit their differentiation into OCs (FIG. 2). In all experiments with the inert BP or non-degradable conjugate control compound, no effects on osteoclast formation or activity were observed.

Both BTCQ 1 and CQ inhibited OC formation on plastic (FIG. 2A). Interestingly, BTCQ was more effective than CQ (at 1 μM vs 3 μM), suggesting that the BP moiety either enables increased uptake of the attached CQ or that it attaches to the plastic on the bottom of the plates making the CQ more accessible to the OC precursors. Importantly, bone slices previously incubated for 12 hours with BTCQ 1 had significantly less resorption pit formation than those incubated with CQ (FIG. 2B), suggesting that the BTCQ 1 remained attached to the bone matrix, despite washing, and CQ did not. It was also found that the non-degradable form of BTCQ 1 had little or no effect for OC and resorption pit formation. Although not wishing to be bound by any particular theory, these results suggest that the enhanced inhibitory effects of BTCQ 1 on OC formation and bone resorption are due to released CQ.

Figure 3:
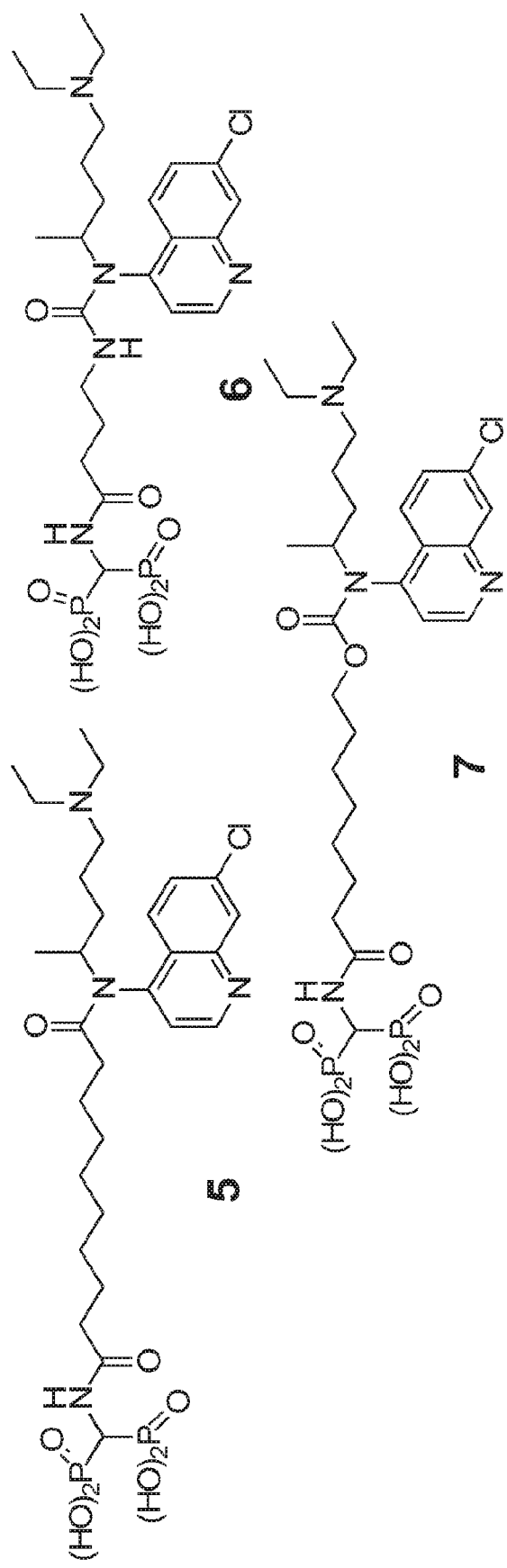
FIG. 3 depicts exemplary bisphosphonate-chloroquine conjugates of the invention with modified linker degradation potential, reflected by differences in linker length.

Non-bioactive BPs were used to avoid confounding effects associated with direct action of active BPs on OCs and bone destruction. A tethered 1-aminomethane-1,1-bisphosphonic acid was chosen as the targeting BP module since it was expected to have limited anti-resorptive activity, thus permitting determination of the activity delivered by the warhead, CQ. Next, a potentially cleavable carbamate conjugate of chloroquine (BTCQ 1) was prepared according to the route shown in FIG. 1 by linking chloroquine (2, blue) to BP hydroxy acid 3 (red). In vitro, BTCQ 1 was shown to release CQ in bone, along with BP hydroxy acid (4). Secondly, for control purposes, the bisphosphonic free acid analog 4 that is released with chloroquine 2 after metabolism in the bone compartment and a non-cleavable amide linked conjugate (5, FIG. 3) were prepared for the initial in vitro testing. Neither of these analogs had any anti-osteoclastic activity in vitro, further confirming the necessity for conjugate release to enable a pharmacological effect on bone cells.

Sufficient quantities of the degradable BTCQ analog BTCQ 1 are generated to determine in dose-response experiments if it will inhibit bone resorption in vivo at doses lower than effective doses of CQ and also to extend the range of analogs for in vitro testing.

Preparation of Sufficient Quantities of BTCQ Prodrug and Analogs

Additional BTCQ analogs are produced in order to attenuate the rate of release of CQ in bone and assist the efforts to understand how to modulate the effects of the compounds to inhibit bone resorption. The ability of these compounds in this series to inhibit OC formation and resorption compared to BTCQ 1 is tested using standard in vitro assays on plastic culture plates and bone slices.

First a large-scale synthesis of suitably pure BTCQ 1 (FIG. 1) is generated for in vivo testing. These are purified using standard techniques such as precipitation from an anti-solvent to >98% purity prior to use in biological studies. The reactions are scaled up from milligram to multigram quantities and the reaction conditions are modulated on that larger scale to obtain high chemical yields in all steps. Purification of the final conjugate is performed by successive precipitation of a solution of BTCQ in dichoromethane by addition of the antisolvent diethyl ether, removing triethylamine hydrobromide, the principle impurity, which remains in solution.

Next, this method is applied to prepare a small group of additional BP conjugates to facilitate in vitro/in vivo optimization of CQ release in this series. Representative structures include a corresponding urea (6) and a longer chain length analog (7, FIG. 3) that are hypothesized to offer slower release characteristics and improve the in vivo pharmacokinetics necessary with this approach. These analogs will be prepared by routes analogous to those employed for BTCQ 1 (FIG. 1). In addition, the bisphosphonate control compound (5) is provided in larger amounts for in vivo comparison. Modifications of the CQ warhead results in customized analogues with novel structures. These analogues provide further information as to how the release rate of chloroquine conjugate analogs on bone can be modulate. For example, other potential attachment points and chemical variants within this structure are explored that may further adjust the warhead release rate.

Determination of the Optimal Effective Dose of BTCQ 1 to Inhibit PTH-Induced Bone Resorption and Bone Marrow Fibrosis In Vivo.

Well-established protocols of 4× daily injection of parathyroid hormone (PTH) for 3 days are used to induce increased osteoclastic bone resorption and marrow fibrosis and administer CQ, BTCQ 1 or vehicle in dose-response experiments before and during PTH administration. The experiments examine whether BTCQ inhibits bone resorption and marrow fibrosis at lower doses than CQ in paraffin-embedded sections of tibial metaphyses using bone histomorphometry.

The effective dose of BTCQ 1 to inhibit PTH-induced OC formation and bone marrow fibrosis is determined in vivo. The efficacy of the BTCQ 1 as prepared as described above is examined in the in vivo hyperparathyroidism bone resorption model (Xiu Y et al., 2014, J Clin Invest 124:297-310), which was first used to demonstrate that recombinant PTH-related peptide induced OC formation and bone resorption as efficaciously as PTH (Yates et al., 1988, J Clin Invest 81:932-8).

2-month-old female C57/BL6 mice are used. 50, 10, and 2, mg/kg of BTCQ 1 or CQ or vehicle is injected i.p. once daily to mice for 10 days, 8 mice/group. 50 mg/kg CQ is the dose that effectively block PTH-induced marrow fibrosis (Xiu Y et al., 2014, J Clin Invest 124:297-310). From day-7, vehicle or PTH (10 µg/injection) are injected 4×/d for 3, as previously reported (Xiu Y et al., 2014, J Clin Invest 124:297-310). Mice re sacrificed at day 10. Long bones and vertebrae re fixed in formalin, decalcified in EDTA and processed through paraffin. Marrow fibrosis and OC parameters are evaluated in H&E and tartrate-resistant acid phosphatase-stained sections, using previously reported methods (Xiu Y et al., 2014, J Clin Invest 124:297-310; Yao et al., 2009, J Clin Invest 119:3024-34).

The OC formation and bone resorption inhibitor effects of the new BTCQ compounds are evaluated in vitro. Bone marrow (BM) cells ($4 \times 10^4$) from C57/BL6 mice are cultured in 96-well plates in α-MEM with 10% fetal bovine serum and M-CSF (10 ng/mL) for 2 days to enrich for OC precursors, which then are treated with CQ or BTCQ (0.3, 1, 3 and 10 µg) and RANKL (10 ng/mL) for an 2-3 additional days in dose-response and time-course studies. M-CSF and RANKL are cytokines essential for OC formation, which are assessed by counting tartrate-resistant acid phosphatase (TRAP)-positive multinucleated OCs. BM cells are also be cultured with M-CSF for 2 d on bone slices to generate OC precursors (OCPs), and then CQ or BTCQ (0.3, 1, 3 and 10 µM) and RANKL (10 ng/mL) are added for 5-9 days in dose-response and time-course studies. Cells are fixed and stained for TRAP activity to allow counting of OCs, which then is removed and bone slices are stained with 0.5% toluidine blue to visualize resorption pits, as described (Xiu Y et al., 2014, J Clin Invest 124:297-310; Yao et al., 2009, J Clin Invest 119:3024-34).

The new BP conjugates produce an anti-resorptive effect when used in vivo because the BP moiety should take most of the attached CQ to bone with the remainder being excreted in the urine (Coxon et al., 2008, Bone 42:848-60; Hughes et al., 1995, J Bone Miner Res 10:1478-87). BTCQ 1 is hypothesized to inhibit PTH-induced marrow fibrosis and OC formation at a much lower dose than CQ. These dose-response experiments then inform for the determination of the lowest effective dose. The enhanced anti-resorptive activity of the BTCQ 1 compared with CQ on bone slices in vitro indicate that OC precursors are able to take up the BTCQ 1 and thereafter degrade the linker carbamate to free the CQ or, less likely, degrade the linkage extracellularly and take up the CQ.

All in vitro experiments are repeated 3 times. An unpaired t-test is used for comparisons between 2 groups. ANOVA followed by Bonferroni/Dunnet test is used for comparisons among more than 2 groups. Mean values and SDs re calculated for each variable. A value of $p < 0.05$ is designated as statistically significant. The sample size of in vivo experiments is based on an un-paired t-test power analysis carried out using SigmaStat Statistical Software: 8 mice are needed in each group where new bone volume is being assessed to detect significant differences from WT controls with an alpha error of 5%. The power is 0.98, i.e. there is 98% chance of detecting a specific effect with a 95% confidence when alpha=0.05.

Example 3: Bone-Targeted Chloroquine Inhibits Osteoclastogenesis and Bone Resorption More Effectively than Chloroquine Described herein is the development of a novel bone-targeted chloroquine (CQ) conjugate (BTCQ) by linking CQ to a bisphosphonate (BP) with high affinity for bone, but no anti-OC activity. This conjugate will employ a linker that is stable in the bloodstream, but will be cleaved in the environment of the bone compartment. Lower, yet effective concentrations of CQ will thus be preferentially delivered to bone and directed away from other tissues to reduce adverse effects.

The materials and methods employed in these experiments are now described.

Figure 5:
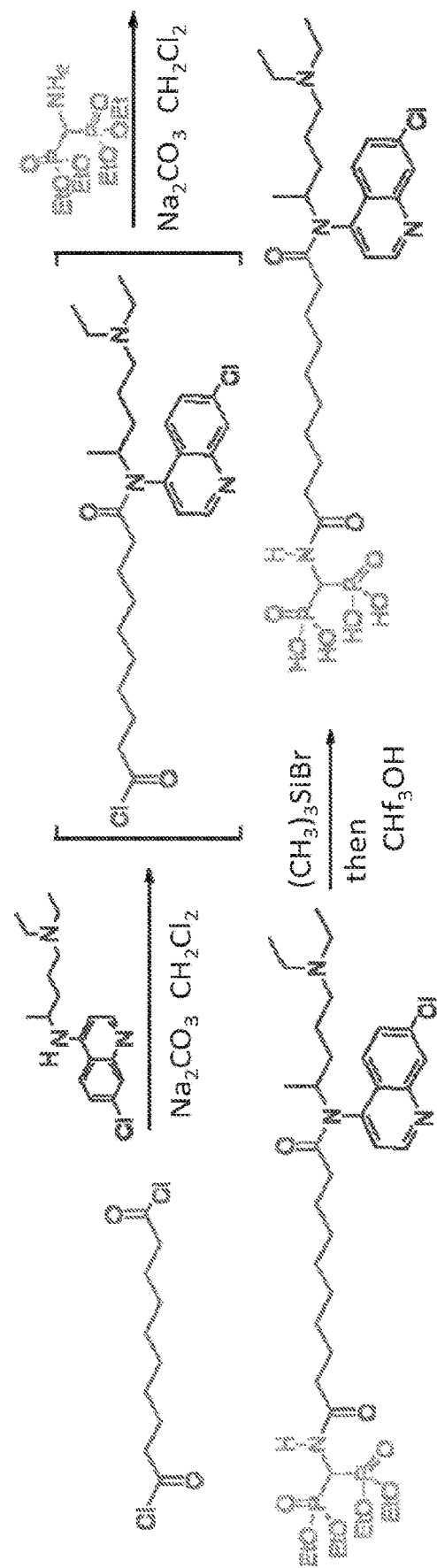
FIG. 5 depicts the synthesis of a Non-Cleavable BTCQ (NC-BTCQ). NC-BTCQ compounds provide a control to test whether cleavage of the BTCQ linkage is required for its key pharmacological effects.

Chemical Synthesis of BTCQ:

The chemical synthesis of BTCQ and NC-BTCQ is described in FIGS. 1 and 5, respectively.

Osteoclastogenesis Assay:

Bone marrow cells from C57Bl6 mice were treated with M-CSF for 2 d to generate OC precursors (OCPs), which were then treated with RANKL plus CQ or BTCQ for 2-3 days to generate OCs. OC numbers and area were evaluated after TRAP staining.

Western Blot Analysis (WB):

Cultured cells were lysed with M-Per mammalian protein extraction reagent. 10-20 μg protein were loaded onto 10% SDS-PAGE gels, transferred onto polyvinylidene difluoride membranes, incubated with primary and secondary Abs, followed by exposure to ECL substrate. Signals were analyzed using a Bio-Rad imaging system.

PTH-Induced Bone Resorption Model:

Mice were given daily injections of CQ or BTCQ for 10 days and 10 μg hPTH were injected SC over calvariae 4×/day for 3 d (day 7 to 10). The mice were euthanized on day 11 (last PTH injection was given 2 hr before death). Tibiae were decalcified and paraffin sections were stained for TRAP activity to evaluate OC formation.

The results of the experiments are now described.

As shown in FIG. 2A, BTCQ inhibits OC formation more effectively than CQ. Further, BTCQ binds to bone matrix more effectively than CQ to inhibit bone resorption (FIG. 2B).

Figure 4:
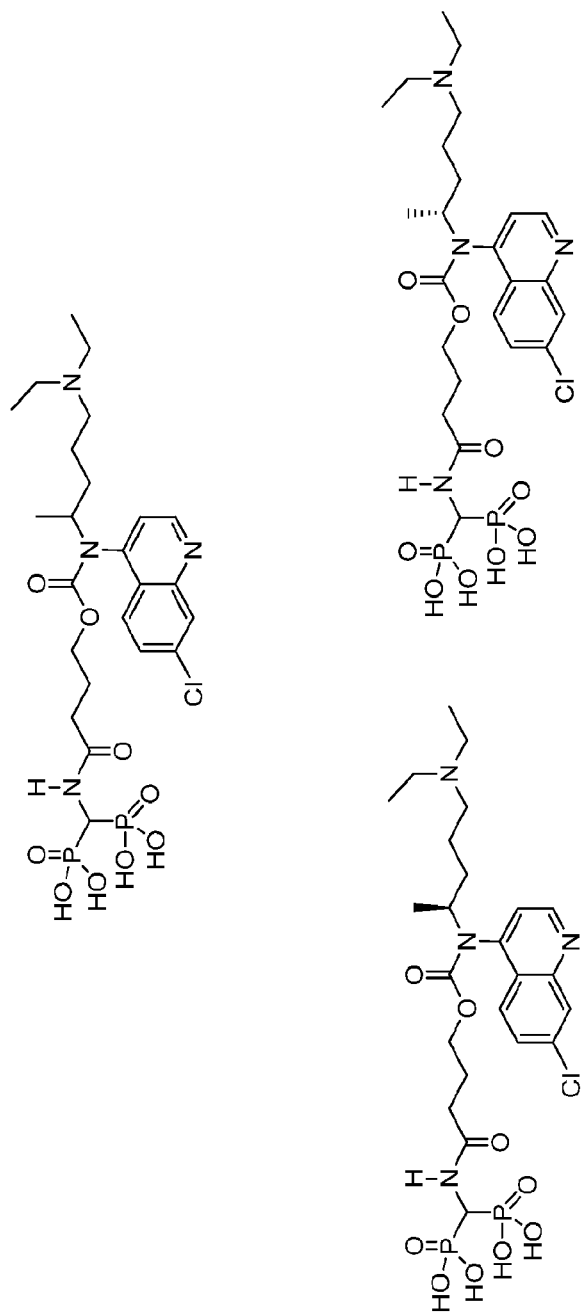
FIG. 4 depicts the structures of racemic BTCQ 1 and the S- and R-enantiomers of BTCQ 1.
Figure 6:
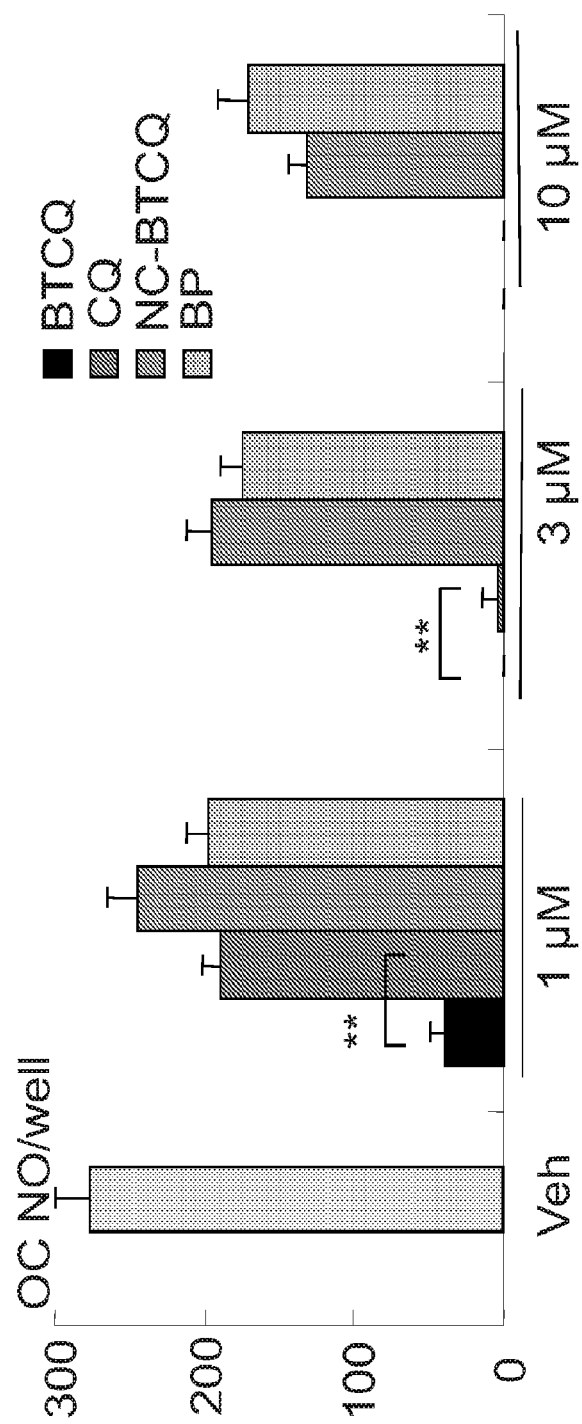
FIG. 6 depicts the minimal inhibitory effect of NC-BTCQ 5 on osteoclast formation. WT mouse bone marrow (BM) cells were cultured on 96-well plastic plates with M-CSF for 2 days, and RANKL+the indicated doses of BTCQ 1, CQ 2, NC-BTCQ 5 or BP carrier were added for 3 more days. Osteoclast numbers were counted after TRAP staining. 4 wells/group. *$p<0.05$, **$p<0.01$.
Figure 7:
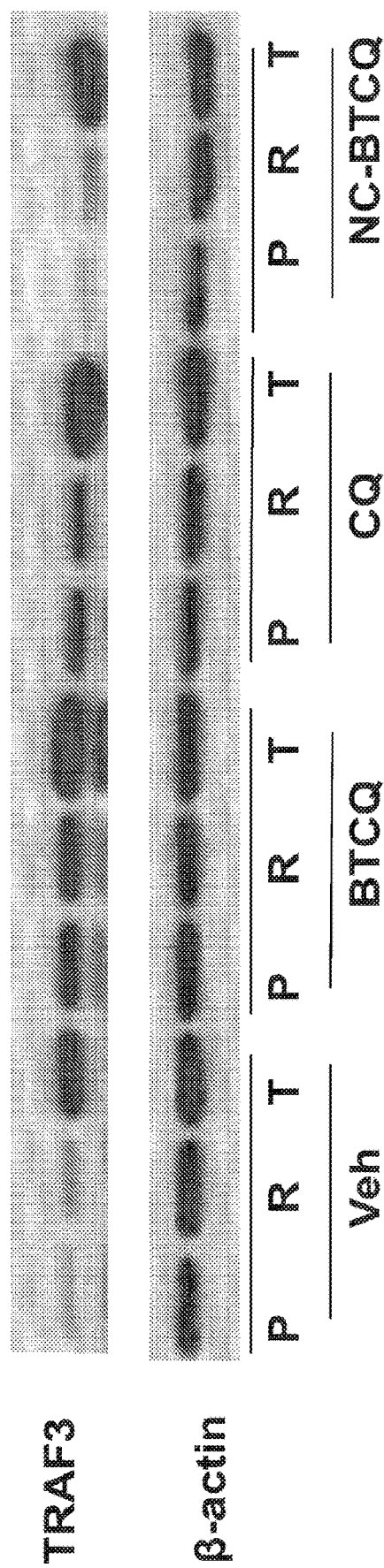
FIG. 7 depicts experimental results demonstrating that unlike CQ and BTCQ, NC-BTCQ does not prevent RANKL-induced degradation of TRAF3, a negative regulator of RANKL-induced OC formation. WT mouse BM cells, cultured with M-CSF as in FIG. 6, were treated with vehicle, BTCQ, CQ or NC-BTCQ (3 µM) for 8 hrs. Cell lysates were used to test TRAF3 and actin protein levels by Western blotting.

To test whether the cleavage of the BTCQ linkage is required for its key pharmacological effects, a non-cleavable amide-linked bisphosphonate conjugate of chloroquine (NC-BTCQ) was synthesized (FIG. 4) and the minimal inhibitory effect of NC-BTCQ on OC formation was tested (FIG. 6). Unlike CQ and BTCQ, NC-BTCQ does not prevent RANKL-induced degradation of TRAF3, a negative regulator of RANKL-induced OC formation (FIGS. 6 and 7).

Figure 8:
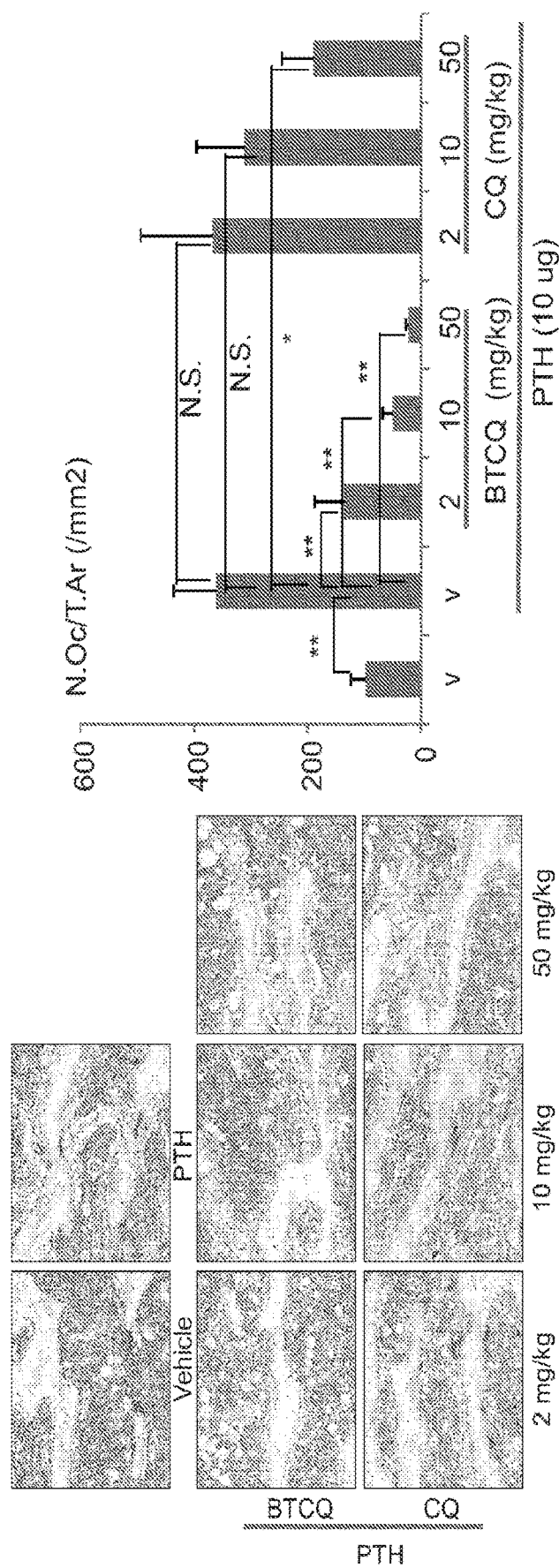
FIG. 8 depicts experimental results demonstrating that BTCQ 1 reduces PTH-induced osteoclast formation in vivo more effectively than CQ 2. Two month-old C57Bl6 female mice were given daily injections (day 1-10) of CQ 2 or BTCQ 1. hPTH (10 µg) was injected SC over calvariae 4x/day in the last 3 days (day 7 to 10). The mice were euthanized on day 11 (last PTH injection was given 2 hours before death). The tibiae were decalcified and paraffin sections were stained for TRAP activity to evaluate OC formation. The numbers of osteoclasts (N.Oc) on the trabecular surfaces of proximal tibiae were expressed per mm2 trabecular area (T.Ar,). *$p<0.05$, **$p<0.01$. 5 mice per group.
Figure 9:
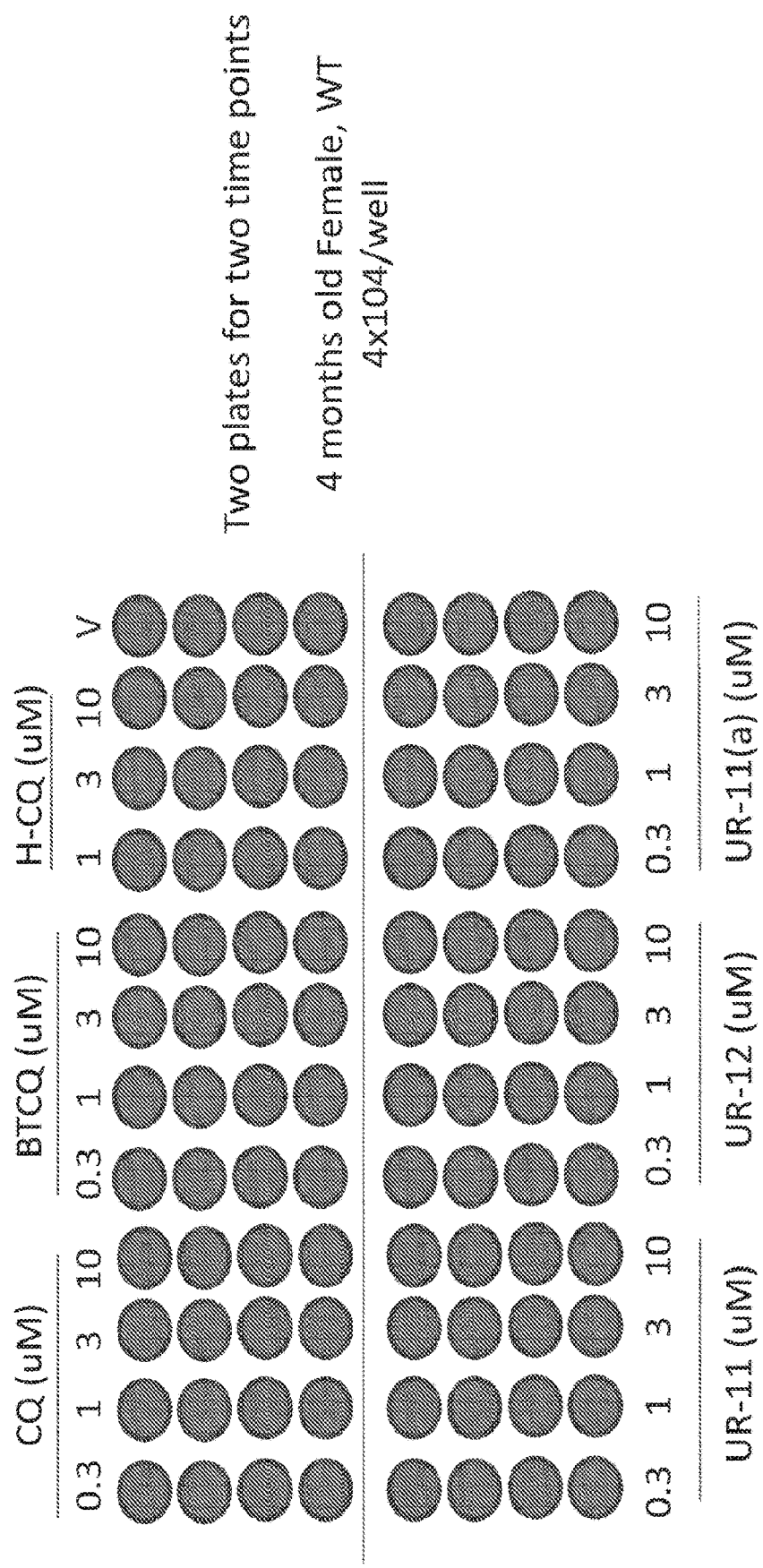
FIG. 9 depicts the experimental set up to study the effect of BTCQ analogs on OC formation.
Figure 10:
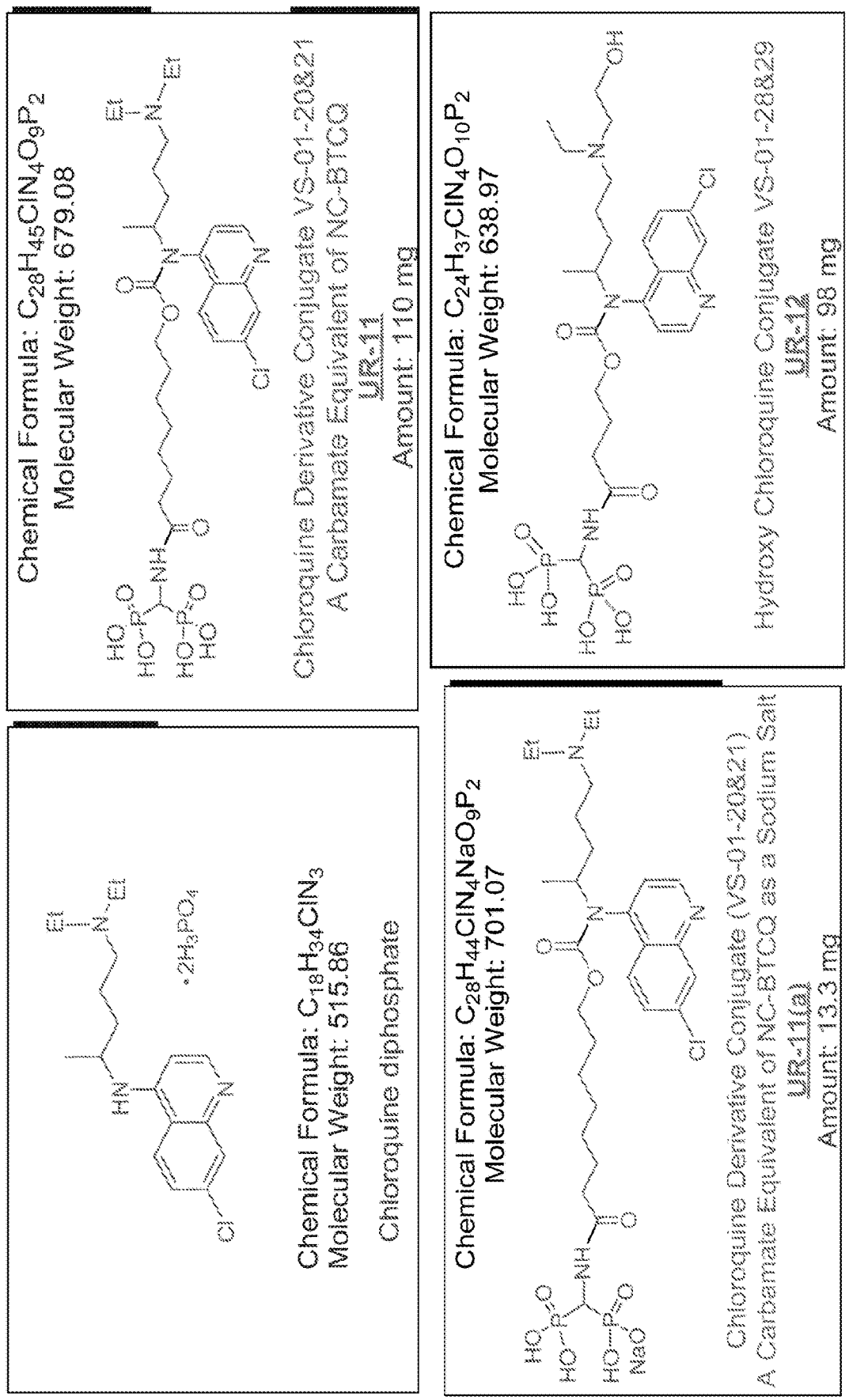
FIG. 10 depicts the structures of BTCQ analogs UR-11, UR-11(a), and UR-12.
Figure 11:
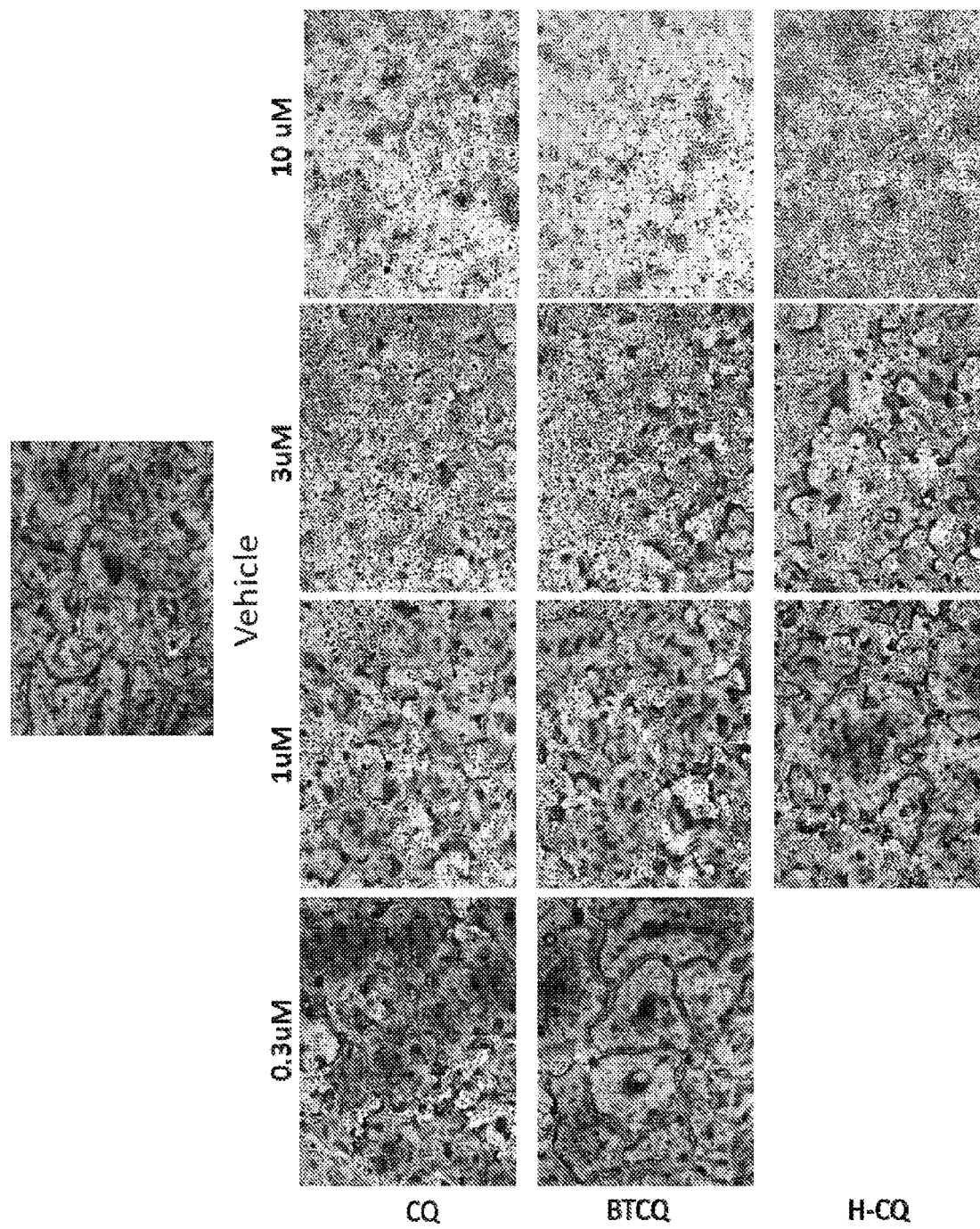
FIG. 11 depicts a panel of images depicting WT mouse bone marrow (BM) cells (osteoclast precursors) treated with CQ, BTCQ, or H-CQ. As evidenced by common osteoclast staining, CQ and BTCQ are more effective at inhibiting osteoclast activity than HCQ.
Figure 12:
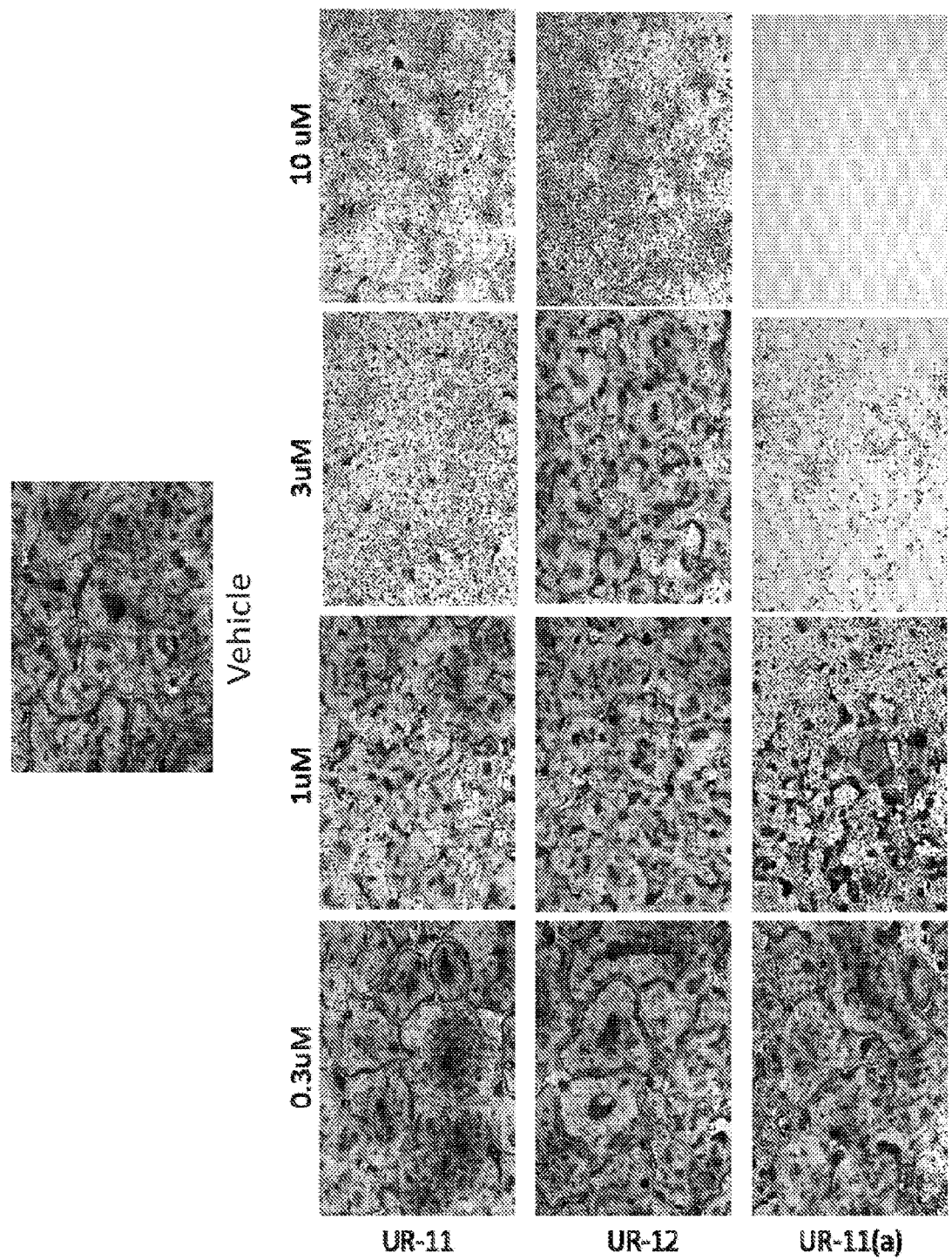
FIG. 12 depicts a panel of images depicting WT mouse bone marrow (BM) cells treated with BTCQ analogs, UR-11, UR-11(a), or UR-12. As evidenced by common osteoclast staining, the carbamates UR-11 and 11(a), which also more effectively release CQ in the presence of osteoclasts are more effective at inhibiting osteoclast activity than the non cleavable amide UR-12.
Figure 18:
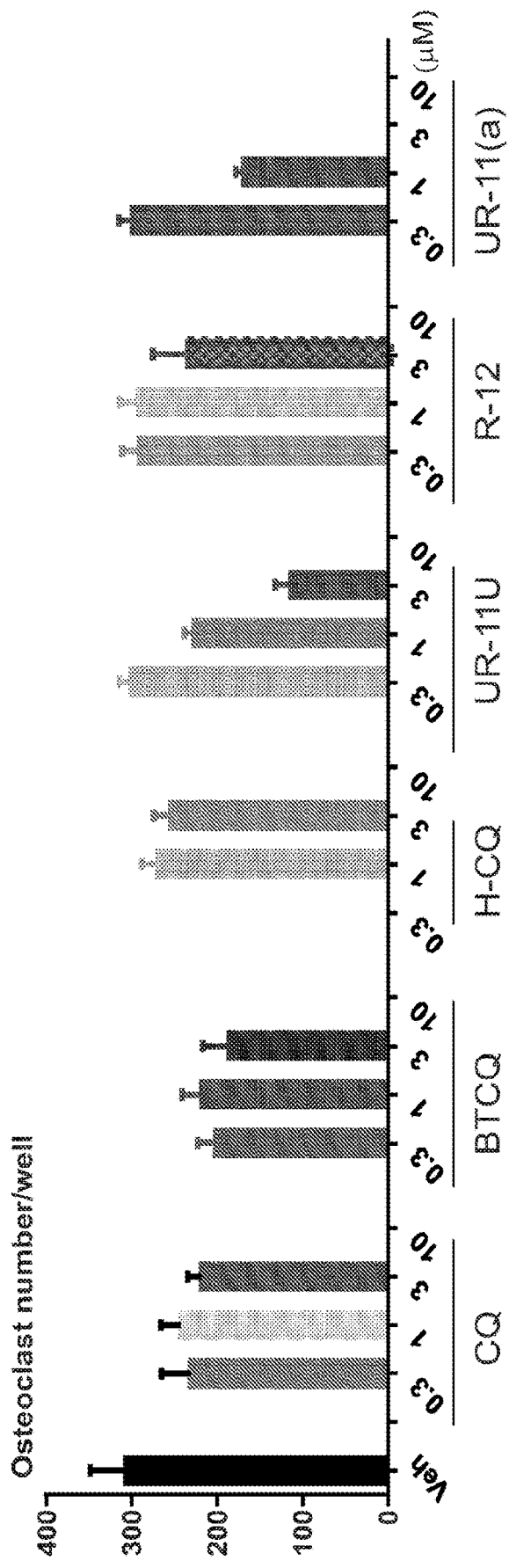
FIG. 18 depicts the effects of chloroquine and chloroquine analogs on osteoclast formation in vitro, as demonstrated by the number of osteoclasts per well.
Figure 19:
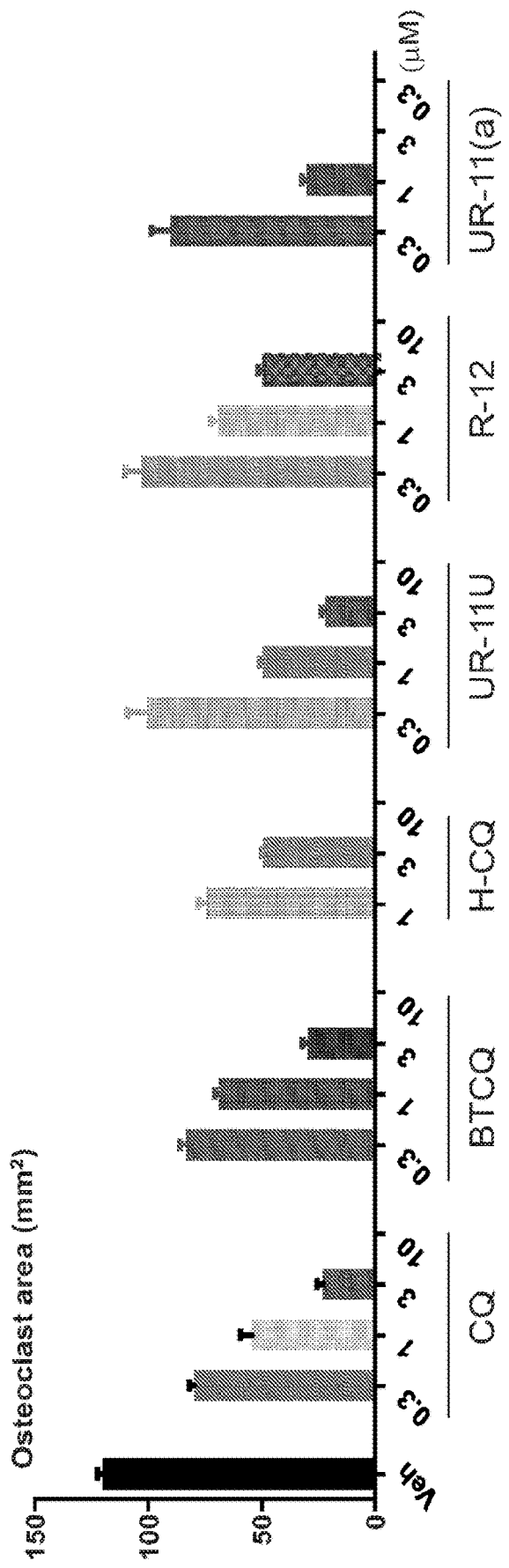
FIG. 19 depicts the effects of chloroquine and chloroquine analogs on osteoclast formation in vitro, as demonstrated by the Osteoclast area ($mm^2$).

To further understand the mechanism of BTCQ inhibition of OC formation, the ability of BTCQ to inhibit PTH-induced OC formation was studied. BTCQ reduces PTH-induced OC formation in vivo more effectively than CQ (FIG. 8). Further, the effects of chloroquine and chloroquine analogs on osteoclast formation were studied in vitro (FIGS. 18-19).

These data demonstrate that BTCQ can bind to bone matrix and releases CQ to inhibit RANKL- and PTH-induced OC formation and bone resorption by preventing TRAF3 degradation at lower concentrations than CQ. Cleavage of CQ from the bisphosphonate is necessary for BTCQ's anti-osteoclastic activity.

Accordingly, BTCQ is a novel and potentially safer analog of CQ that can be targeted to bone as an anti-resorptive and anti-inflammatory agent for the prevention of bone loss in diseases characterized by increased OC formation. It should be possible to give significantly lower, yet still effective concentrations of CQ with fewer adverse effects by administering it in this bone-targeted formulation.

Example 4: Synthesis and Activity of BTCQ Analogs

Figure 13:
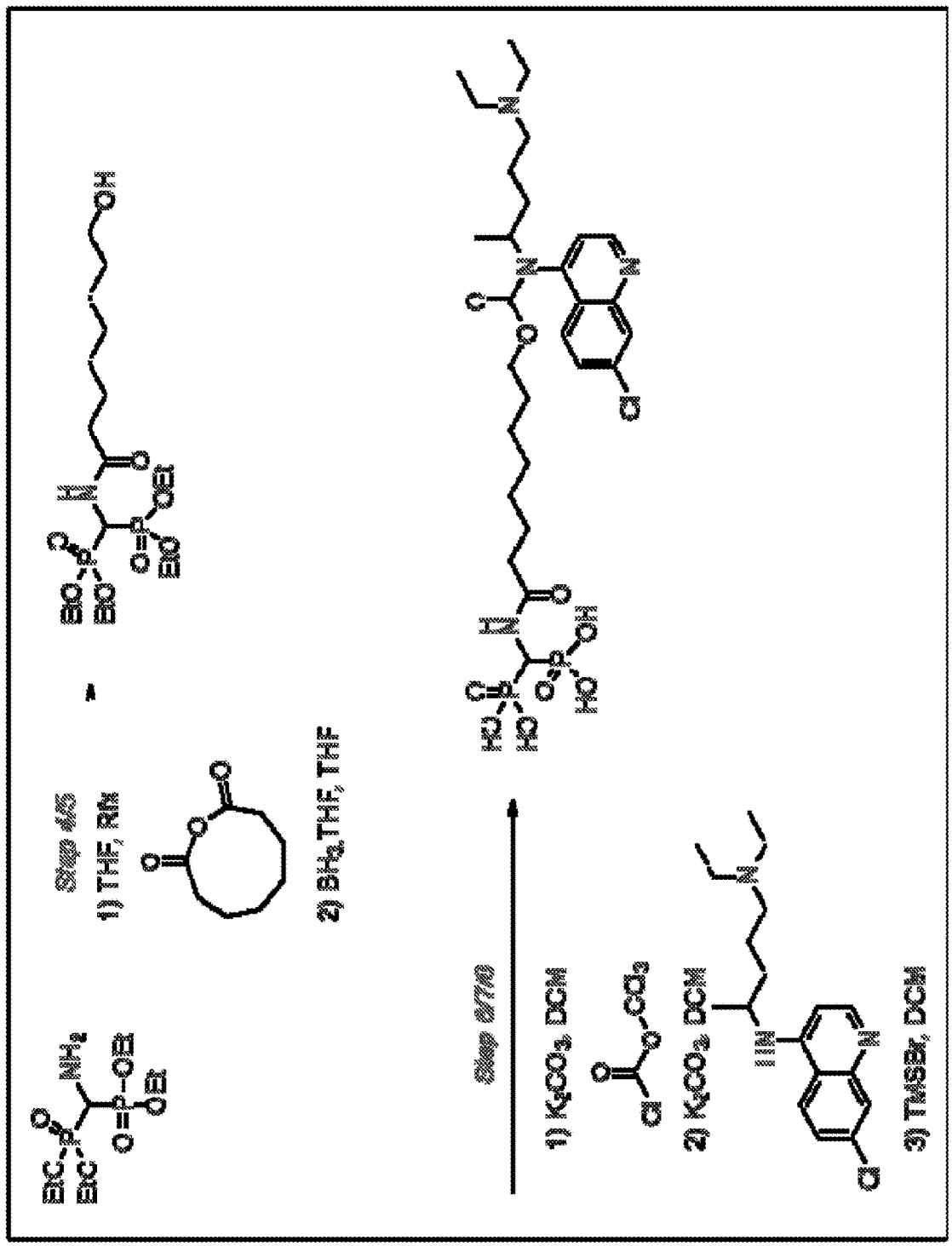
FIG. 13 depicts an exemplary synthesis of UR-11 (rac-(13-(7-chloroquinolin-4-yl)-18-ethyl-14-methyl-3,12-dioxo-11-oxa-2,13,18-triazaicosane-1,1-diyl)diphosphonic acid).

Described herein is the synthetic route of BTCQ analogs UR-11, UR-11a, and UR-12 and their ability to inhibit OC formation Synthesis of UR-11; rac-(13-(7-chloroquinolin-4-yl)-18-ethyl-14-methyl-3,12-dioxo-11-oxa-2,13,18-triazaicosane-1,1-diyl)diphosphonic acid An exemplary synthesis of UR-11 (rac-(13-(7-chloroquinolin-4-yl)-18-ethyl-14-methyl-3,12-dioxo-11-oxa-2,13,18-triazaicosane-1,1-diyl)diphosphonic acid) is shown in FIG. 13.

Step 4/5: Synthesis of tetraethyl ((8-hydroxyoctanamido)methylene)-bis(phosphonate)

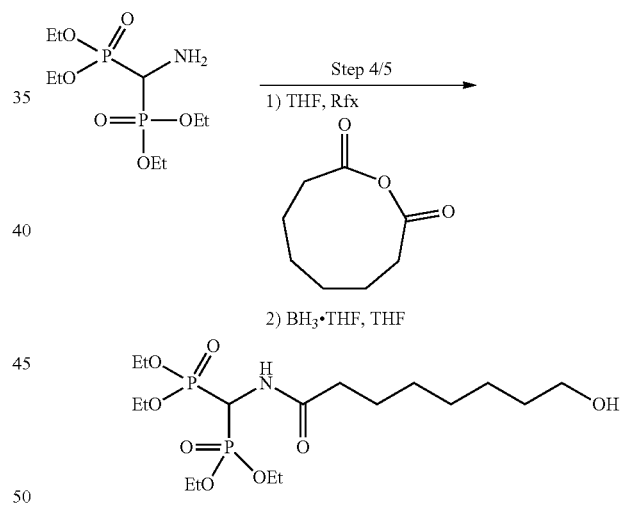

An oven dried round bottom flask was charged with a solution of tetraethyl (aminomethylene)bis(phosphonate) in anhydrous tetrahydrofuran (0.868 g, 2.86 mmol in 6 mL). Suberic anhydride (0.535 g, 3.43 mmol) was added in one portion and the contents were refluxed for 5 h. After cooling to 0° C., the reaction mixture was treated with a solution of borane in tetrahydrofuran (6.4 mL, 6.4 mmol, 1 M) and the contents were gradually warmed to room temperature and stirred for 4 h. After cooling to 0° C., the reaction mixture was carefully quenched with methanol (5 mL) and the contents were gradually warmed to room temperature and stirred for 1 h. The reaction mixture was concentrated under reduced pressure and the crude mixture was purified by column chromatography on silica (0-8% methanol in dichloromethane) to yield (1.02 g, 80%) tetraethyl ((8-hydroxyoctanamido)methylene)-bis(phosphonate) as colorless oil.

$R_f$ 0.25 (5% of methanol in dichloromethane, KMnO$_4$ active)

Thermo-MS (ESI) m/z (M+H) Calcd for $C_{17}H_{37}NO_8P_{22}$: 446.4 found: 446.4

$^1$H-NMR (400 MHz, CDCl$_3$) δ 6.13 (d, J=8 Hz, 1H), 5.11-4.93 (m, 1H), 4.29-4.05 (m, 10H), 3.61-3.51 (m, 1H), 2.21 (t, J=8 Hz, 2H), 1.67-1.41 (m, 4H), 1.39-1.21 (m, 18H).

$^{13}$C-NMR (100 MHz, CDCl$_3$) δ 172.24, 63.4 (d, J=64 Hz), 62.34, 43.11 (t, J=588 Hz), 35.95, 35.75, 32.46, 28.89, 25.53, 25.20, 16.2.

Step 6/7/8: Synthesis of rac-(13-(7-chloroquinolin-4-yl)-18-ethyl-14-methyl-3,12-dioxo-11-oxa-2,13,18-triazaicosane-1,1-diyl)diphosphonic acid

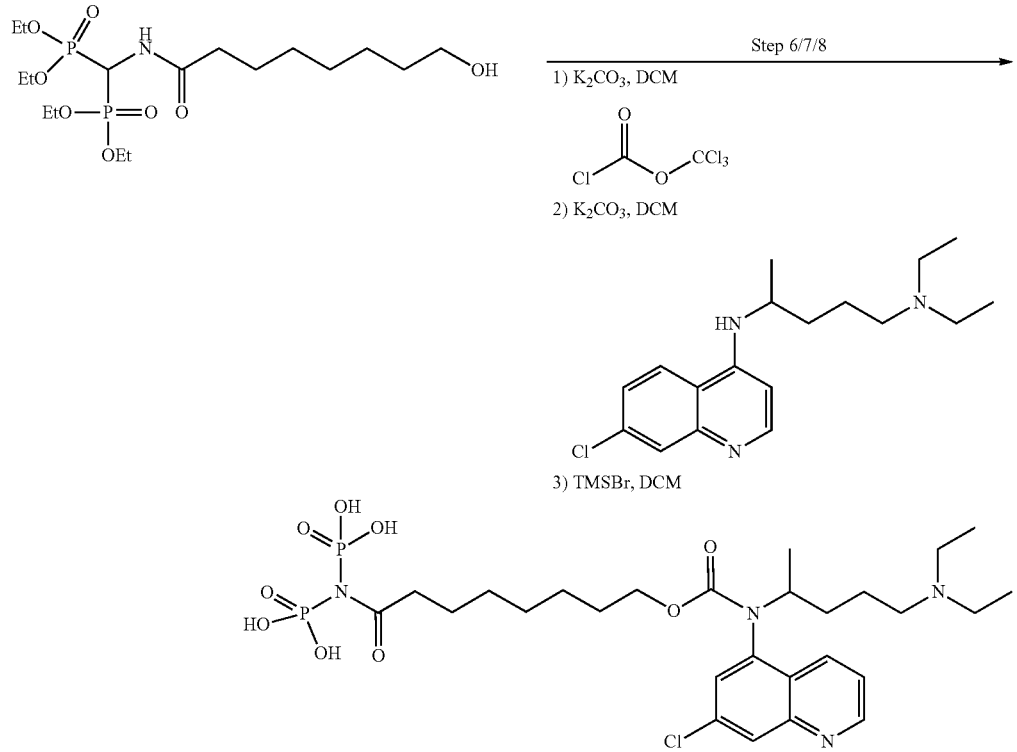

An oven dried round bottom flask was charged with a solution of tetraethyl ((8-hydroxyoctanamido)methylene)-bis(phosphonate) in anhydrous dichloromethane (0.2 g, 0.449 mmol in 3 mL) and pre-activated potassium carbonate (0.31 g, 2.24 mmol). After cooling to 0° C., neat diphosgene (0.1 mL, 0.898 mmol) was added drop wise and the contents were stirred at 0° C. for 2 h. The reaction mixture was diluted with anhydrous dichloromethane (10 mL) and the contents were filtered. The filtrate was concentrated under reduced pressure and dried under vacuum for 2 h, before taking to the next step.

An oven dried round bottom flask was charged with the solution of rac-chloroquine in anhydrous dichloromethane (0.15 g, 0.47 mmol in 2 mL). Potassium carbonate (0.347 g, 2.24 mmol) was added and the white suspension was cooled to 0° C. A solution of chloroformate in anhydrous dichloromethane (0.265 g, 0.47 mmol in 0.3 mL) was added and the contents were stirred at 0° C. for 2 h. The reaction mixture was diluted with dichloromethane (10 mL) and the contents were filtered. The filtrate was concentrated under reduced pressure and the crude mixture was taken to the next step without purification.

An oven dried round bottom flask was charged with a solution of crude mixture from previous step in anhydrous dichloromethane (0.3 g, 0.379 mmol in 2 mL). After cooling to 0° C., neat trimethylsilyl bromide (0.25 mL) was added and the contents were gradually warmed to room temperature and stirred for 24 h. The reaction mixture was concentrated under reduced pressure and the crude mixture was dissolved in anhydrous methanol (10 mL). After stirring at room temperature for 10 min, the reaction mixture was concentrated under reduced pressure. The above process was repeated twice and the crude mixture was washed with diethyl ether (3 times) to yield rac-(13-(7-chloroquinolin-4-yl)-18-ethyl-14-methyl-3,12-dioxo-11-oxa-2,13,18-triazaicosane-1,1-diyl)diphosphonic acid (0.285 g, 93%) as lemon yellow powder.

Thermo-MS (ESI) m/z (M+H) Cald for $C_{28}H_{45}ClN_4O_9P_2$: 680.08, found: 680.08

$^1$H-NMR (400 MHz, CDCl$_3$) δ8.63 (d, J=5 Hz, 1H), 8.51-8.39 (m, 1H), 7.84 (s, 1H), 7.63 (d, J=5 Hz, 1H), 6.98-6.91 (m, 1H), 4.61-4.54 (m, 1H), 4.23-4.11 (m, 2H), 3.32-3.11 (m, 7H), 2.31-2.22 (m, 2H), 1.99-1.74 (m, 6H), 1.63-1.53 (m, 2H), 1.43-1.33 (m, 4H), 1.31-1.18 (m, 12H).

$^{13}$C-NMR (100 MHz, CDCl$_3$) δ 177.63, 174.82, 155.21, 143.11, 138.71, 138.57, 127.11, 126.10, 119.21, 115.51, 99.07, 69.05, 52.17, 48.07, 46.53, 43.01, 35.95, 35.71, 34.31, 32.43, 28.84, 25.51, 23.71, 20.01, 16.13, 11.15.

$^{31}$P-NMR (400 MHz, CD$_3$OD) δ 15.57, 15.45.

Figure 14:
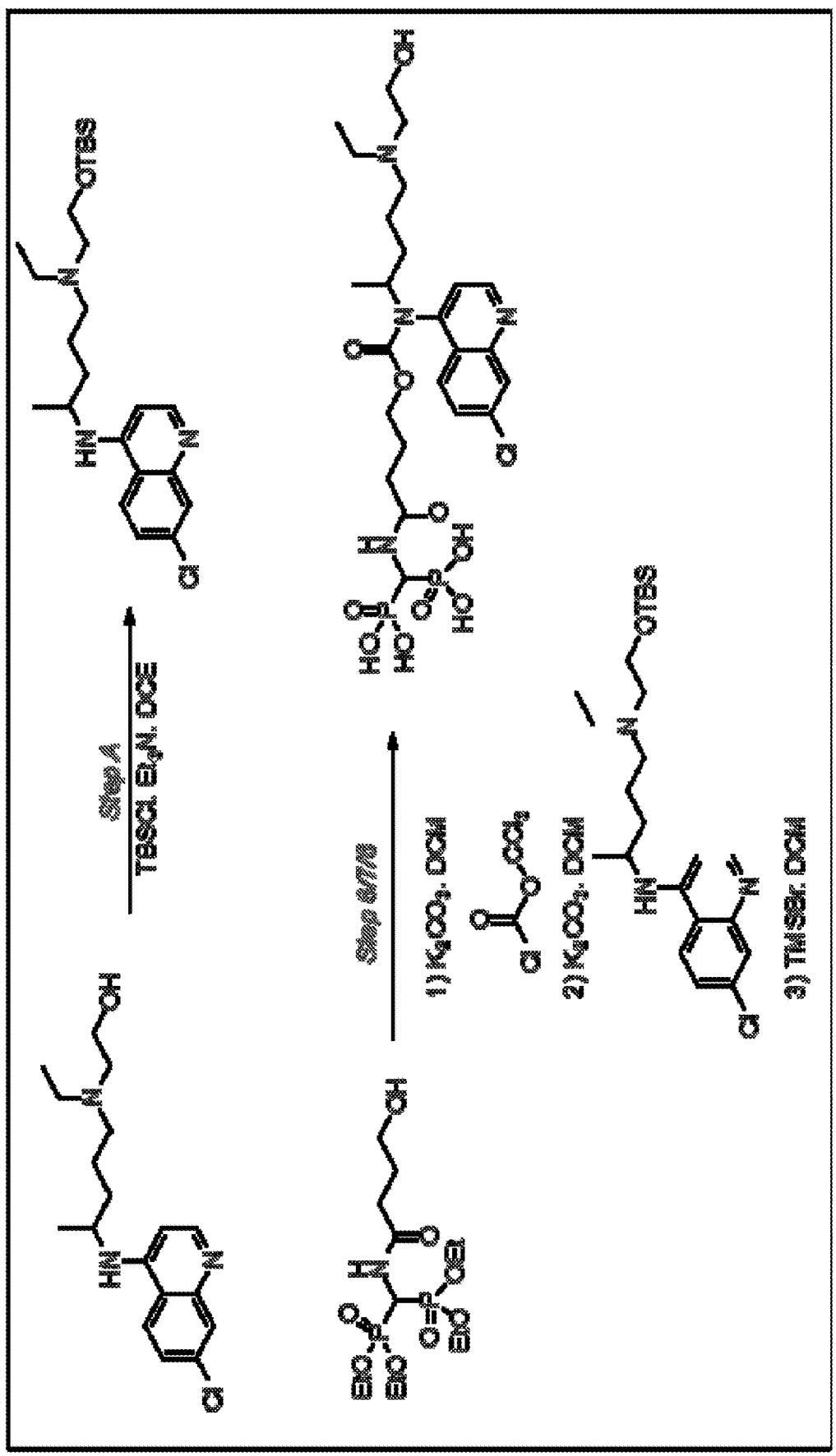
FIG. 14 depicts an exemplary synthesis of UR-12 (rac-(9-(7-chloroquinolin-4-yl)-14-ethyl-16-hydroxy-10-methyl-3,8-dioxo-7-oxa-2,9,14-triazahexadecane-1,1-diyl)diphosphonic acid).

Synthesis of UR-12; rac-(9-(7-chloroquinolin-4-yl)-14-ethyl-16-hydroxy-10-methyl-3,8-dioxo-7-oxa-2,9,14-triazahexadecane-1,1-diyl)diphosphonic acid An exemplary synthesis of UR-12 (rac-(9-(7-chloroquinolin-4-yl)-14-ethyl-16-hydroxy-10-methyl-3,8-dioxo-7-oxa-2,9,14-triazahexadecane-1,1-diyl)diphosphonic acid) is shown in FIG. 14.

Step A: Synthesis of $N^1$-(2-((tert-butyldimethylsilyl)oxy)ethyl)-$N^4$-(7-chloroquinolin-4-yl)-$N^1$-ethylpentane-1,4-diamine

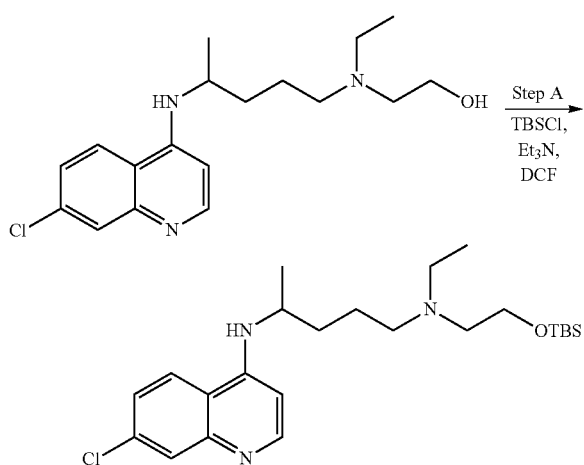

An oven dried round bottom flask was charged with a solution of rac-2-((4-((7-chloroquinolin-4-yl)amino)pentyl)(ethyl)amino)ethanol in anhydrous dichloroethane (0.3 g, 0.893 in 2 mL). Neat triethylamine (0.37 mL, 2.67 mmol) and tert-butylchlorodimethylsilane (0.161 g, 1.07 mmol) were added sequentially and the resultant white suspension was stirred at room temperature for 2 d. The reaction mixture was concentrated under reduced pressure and the crude mixture was purified by column chromatography on silica (0% to 9% methanol in dichloromethane) to yield rac-$N^1$-(2-((tert-butyldimethylsilyl)oxy)ethyl)-$N^4$-(7-chloroquinolin-4-yl)-$N^1$-ethylpentane-1,4-diamine (0.27 g, 68%) as colorless oil which turned into white solid upon standing.

$R_f$ 0.25 (5% of methanol in dichloromethane, $KMnO_4$ active)

Thermo-MS (ESI) m/z (M+H) Cald for $C_{24}H_{40}ClN_3OSi$: 451.13 and 452.13, found: 451.1 and 452.1

$^1$H-NMR (400 MHz, $CDCl_3$) δ 8.44 (d, J=4 Hz, 1H), 7.94-7.82 (m, 2H), 7.33 (dd, $J_1$=8 Hz, $J_2$=4 Hz, 1H), 6.36 (J=4 Hz, 1H), 3.84-3.69 (m, 3H), 2.81-2.61 (m, 6H), 1.89-1.75 (m, 1H), 1.74-1.59 (m, 3H), 1.30 (d, J=8 Hz, 3H), 1.08 (t, J=8 Hz, 3H), 0.83 (s, 9H), 0.01 (s, 6H).

$^{13}$C-NMR (100 MHz, $CDCl_3$) δ 150.2, 150.15, 147.59, 135.41, 126.99, 125.45, 122.37, 117.07, 98.79, 60.48, 54.76, 53.57, 48.6, 48.27, 33.85. 25.8, 23.29, 20.12, 18.14, 10.62, −5.48.

Step 6/7/8: Synthesis of rac-(9-(7-chloroquinolin-4-yl)-14-ethyl-16-hydroxy-10-methyl-3,8-dioxo-7-oxa-2,9,14-triazahexadecane-1,1-diyl)diphosphonic acid

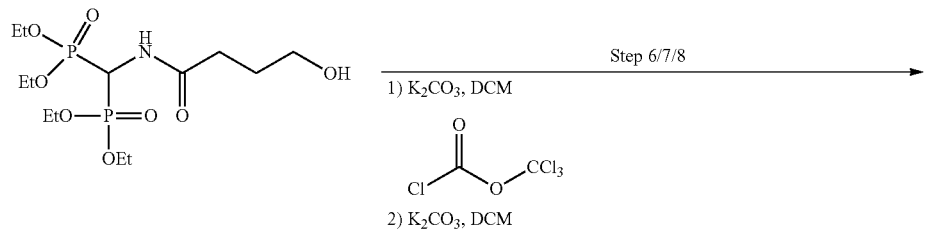

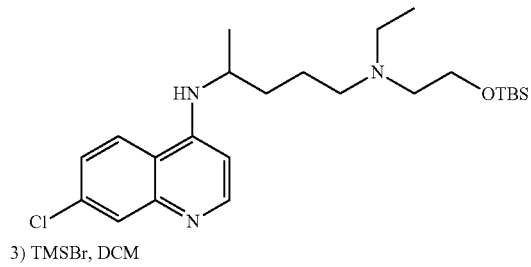

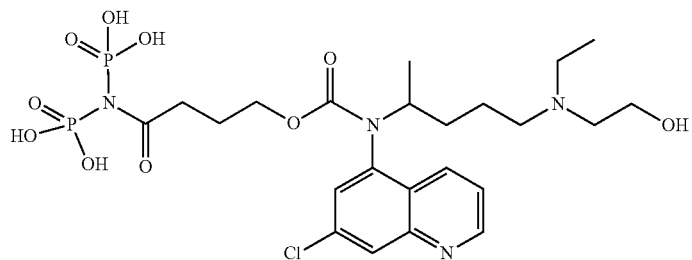

An oven dried round bottom flask was charged with a solution of tetraethyl ((4-hydroxybutanamido)methylene)bis(phosphonate) in anhydrous dichloromethane (0.096 g, 0.246 mmol in 1.4 mL) and pre-activated potassium carbonate (0.31 g, 2.17 mmol). After cooling to 0° C., neat diphosgene (0.06 mL, 0.492 mmol) was added drop wise and the contents were stirred at 0° C. for 2 h. The reaction mixture was diluted with anhydrous dichloromethane (10 mL) and the contents were filtered. The filtrate was concentrated under reduced pressure and dried under high vacuum for 2 h, before taking to the next step.

An oven dried round bottom flask was charged with the solution of rac-M-(2-((tert-butyldimethylsilyl)oxy)ethyl)-$N^4$-(7-chloroquinolin-4-yl)-$N^1$-ethylpentane-1,4-diamine in anhydrous dichloromethane (0.117 g, 0.259 mmol in 0.7 mL). Potassium carbonate (0.3 g, 2.24 mmol) was added and the white suspension was cooled to 0° C. A solution of chloroformate in anhydrous dichloromethane (0.12 g, 0.259 mmol in 0.7 mL) was added and the contents were stirred at 0° C. for 2 h. The reaction mixture was diluted with dichloromethane (10 mL) and the contents were filtered. The filtrate was concentrated under reduced pressure and the crude mixture was taken to the next step without purification.

An oven dried round bottom flask was charged with a solution of crude mixture from previous step in anhydrous dichloromethane (0.193 g, 0.246 mmol in 1.1 mL). After cooling to 0° C., neat trimethylsilyl bromide (0.27 mL) was added and the contents were gradually warmed to room temperature and stirred for 36 h. The reaction mixture was concentrated under reduced pressure and the crude mixture was dissolved in anhydrous methanol (10 mL). After stirring at room temperature for 10 min, the reaction mixture was concentrated under reduced pressure. The above process was repeated twice and the crude mixture was washed with diethyl ether (3 times) to yield rac-(9-(7-chloroquinolin-4-yl)-14-ethyl-16-hydroxy-10-methyl-3,8-dioxo-7-oxa-2,9,14-triazahexadecane-1,1-diyl)diphosphonic acid (0.132 g, 84%) as pale brown powder.

Thermo-MS (ESI) m/z (M+H) Cald for $C_{24}H_{37}ClN_4O_{10}P_2$: 639.97 and 640.97 found: 640 and 641

$^1$H-NMR (400 MHz, CDCl$_3$) δ 8.6-8.45 (m, 2H), 7.99-7.89 (bs, 1H), 7.71-7.56 (bs, 1H), 7.01-6.81 (bs, 1H), 4.59-4.41 (m, 1H), 4.28-4.19 (m, 2H), 3.79-3.61 (m, 3H), 3.62-3.49 (m, 1H), 3.39-3.25 (m, 2H), 3.21-2.95 (m, 4H), 2.39-2.31 (m, 2H), 2.28-2.01 (m, 2H), 1.89-1.51 (m, 4H), 1.37-1.09 (m, 6H).

$^{13}$C-NMR (100 MHz, CDCl$_3$) δ 177.67, 174.86, 155.25, 143.14, 138.74, 138.61, 127.26, 126.13, 119.25, 115.58, 99.14, 69.12, 55.36, 53.66, 51.97, 49.64, 48.08, 32.15, 28.08, 25.9, 21.2, 20.26, 19.75, 8.67.

$^{31}$P-NMR (400 MHz, CD$_3$OD) δ 14.37

Figure 15:
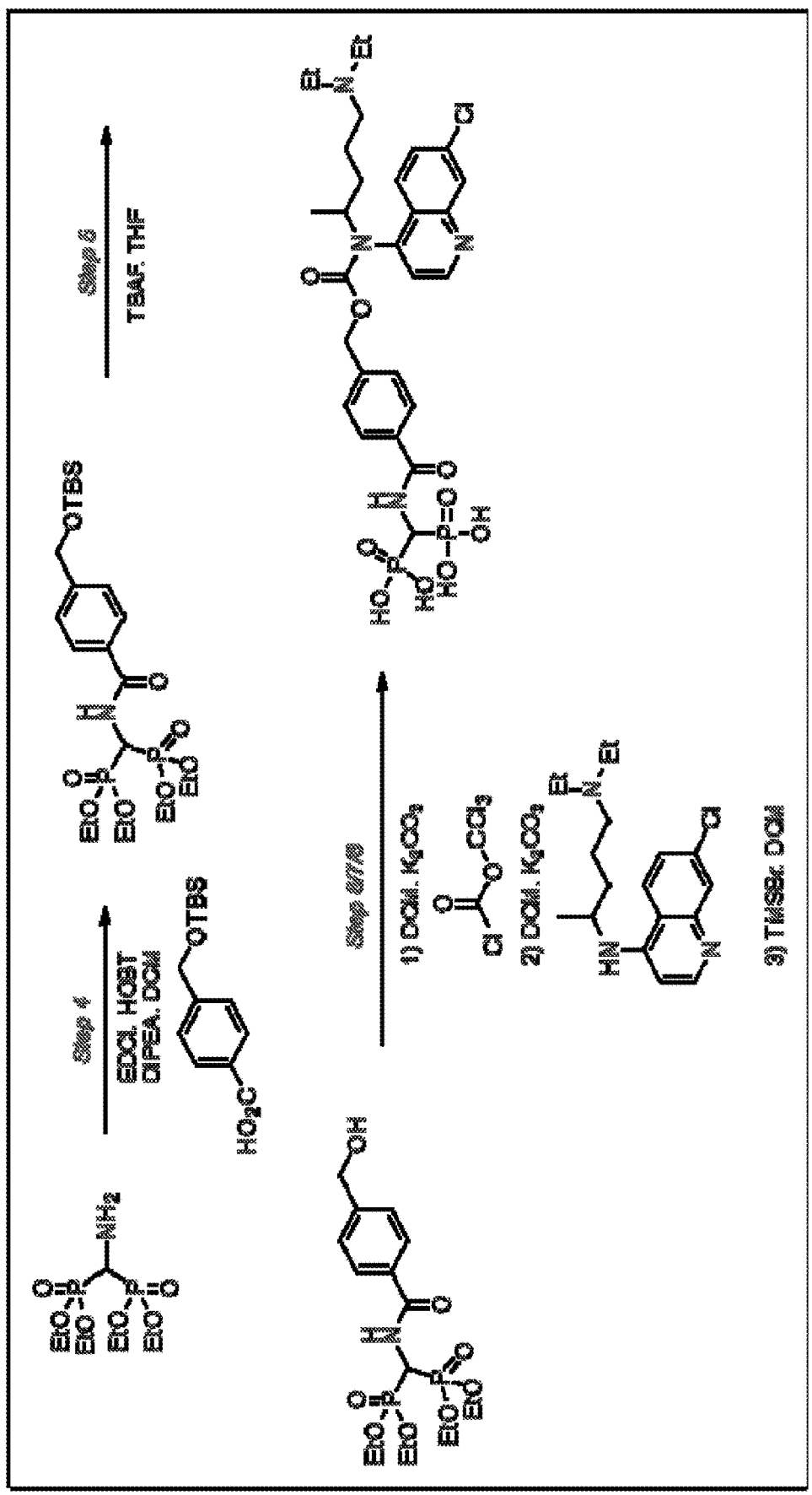
FIG. 15 depicts an exemplary synthesis of rac-((4-((((7-chloroquinolin-4-yl)(5-(diethylamino)pentan-2-yl)carbamoyl)oxy)methyl)benzamido)methylene)diphosphonic acid.

Synthesis of rac-((4-((((7-chloroquinolin-4-yl)(5-(diethylamino)pentan-2-yl)carbamoyl)oxy)methyl)benzamido)methylene)diphosphonic acid An exemplary synthesis of rac-((4-((((7-chloroquinolin-4-yl)(5-(diethylamino)pentan-2-yl)carbamoyl)oxy)methyl)benzamido)methylene)diphosphonic acid is shown in FIG. 15.

Step 4: Synthesis of tetraethyl ((4-(((tert-butyldimethylsilyl)oxy)methyl) benzamido)methylene)bis(phosphonate)

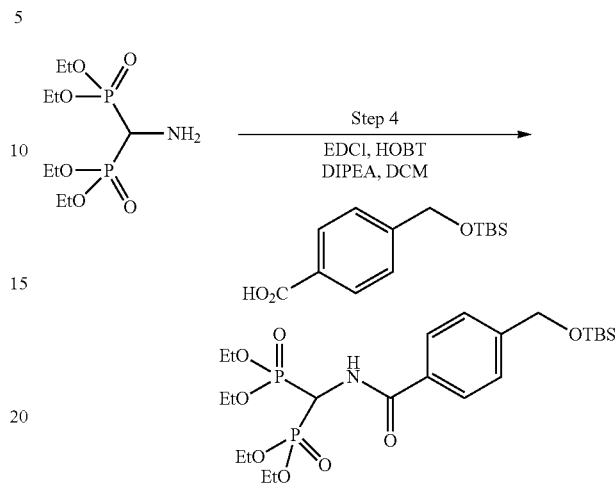

An oven dried round bottom flask was charged with a solution of 4-(((tert-butyldimethylsilyl)oxy)methyl)benzoic acid in dichloromethane (0.3 g, 1.12 mmol in 2 mL). Neat N,N-diisopropylethylamine (0.3 mL, 1.68 mmol), EDC (0.279 g, 1.45 mmol) and HOBT (0.22 g, 1.45 mmol) were added sequentially and the contents were stirred at room temperature for 20 min. Neat tetraethyl (aminomethylene)bis(phosphonate) (0.34 g, 1.12 mmol) was added and the contents were stirred at room temperature for 14 h. After quenching with water (1 mL), the phases were separated and the aqueous layer was extracted with ethyl acetate (2×5 mL). The combined organic layer was dried over anhydrous sodium sulphate, filtered and concentrated under reduced pressure. The crude mixture was purified by column chromatography on silica (0-3% of methanol in dichloromethane) to yield tetraethyl ((4-(((tert-butyldimethylsilyl)oxy)methyl)benzamido)methylene)bis(phosphonate) (0.379 g, 61%) as white flaky solid.

$R_f$ 0.3 (3% of methanol in dichloromethane, KMnO$_4$ active & UV active)

Thermo-MS (ESI) m/z (M+H) Cald for $C_{23}H_{43}NO_8P_2Si$: 552.6, found: 552.6

$^1$H-NMR (400 MHz, CDCl$_3$) δ 7.73 (d, J=8 Hz, 2H), 7.38 (d, J=8 Hz, 2H), 6.53 (d, J=12 Hz, 1H), 5.35-5.08 (m, 1H), 4.75 (s, 2H), 4.28-4.05 (m, 8H), 1.37-1.15 (m, 12H), 0.92 (s, 9H), 0.08 (s, 6H).

$^{13}$C-NMR (100 MHz, CDCl$_3$) δ 166.26, 145.85, 131.73, 127.12, 125.91, 64.28, 63.5 (d, J=40 Hz), 43.92 (t, J=588 Hz), 25.78, 18.24, 16.25 (d, J=28 Hz), −5.43, −5.71

$^{31}$P-NMR (400 MHz, CD$_3$OD) δ 17.05.

Step 5: Synthesis of tetraethyl ((4-(hydroxymethyl)benzamido)methylene)bis(phosphonate)

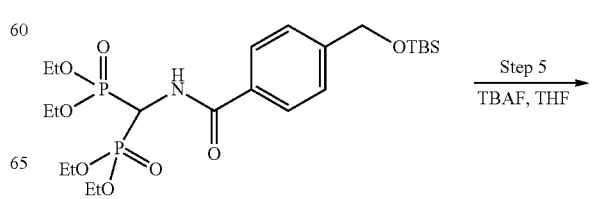

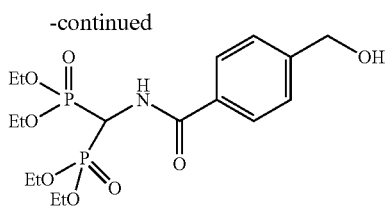

An oven dried round bottom flask was charged with a solution of ((4-(((tert-butyldimethylsilyl)oxy)methyl)benzamido)methylene)bis(phosphonate) in anhydrous tetrahydrofuran (0.29 g, 0.525 mmol in 1.5 mL). A solution of tetrabutylammonium fluoride in tetrahydrofuran (1.57 mL, 1.57 mmol, 1 M) was added drop wise and the contents were stirred at room temperature for an hour. The reaction mixture was concentrated under reduced pressure and the crude mixture was purified by column chromatography on silica (0%-4% of methanol in dichloromethane) to yield tetraethyl ((4-(hydroxymethyl)benzamido)methylene)bis(phosphonate) (0.19 g, 88%) as white solid.

$R_f$ 0.4 (3% of methanol in dichloromethane, $KMnO_4$ active & UV active)

Thermo-MS (ESI) m/z (M+H) Cald for $C_{17}H_{29}NO_8P_2$: 438.3, found: 438.3

$^1$H-NMR (400 MHz, $CDCl_3$) δ 7.74 (d, J=6.4 Hz, 2H), 7.40 (d, J=6.4 Hz, 2H), 6.70 (d, J=8 Hz, 1H), 5.35-5.15 (m, 1H), 4.74 (d, J=4.4 Hz, 2H), 4.32-4.05 (m, 8H), 2.16 (bs, 1H), 1.38-1.18 (m, 12H).

$^{13}$C-NMR (100 MHz, $CDCl_3$) δ 166.61, 145.53, 131.77, 127.24, 126.81, 63.83, 63.71 (d, J=48 Hz), 52.2, 43.89 (t, J=184 Hz), 16.27

$^{31}$P-NMR (400 MHz, $CD_3OD$) δ 17.27

Step 6/7/8: Synthesis of rac-((4-((((7-chloroquinolin-4-yl)(5-(diethylamino)pentan-2-yl)carbamoyl)oxy)methyl)benzamido)methylene)diphosphonic acid

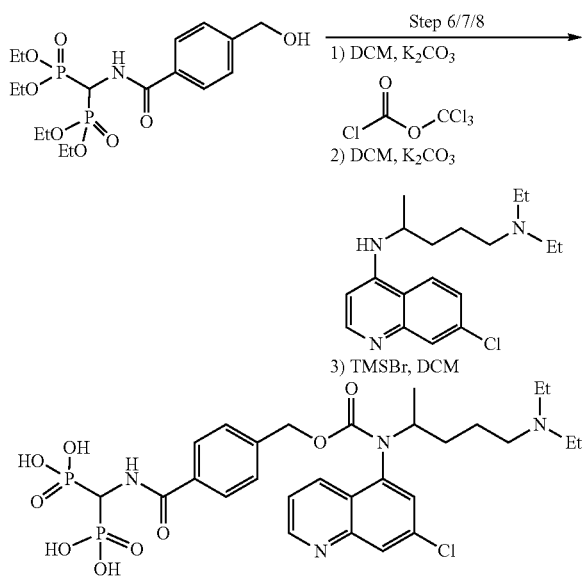

An oven dried round bottom flask was charged with a solution of tetraethyl ((4-(hydroxymethyl)benzamido)methylene)bis(phosphonate) in anhydrous dichloromethane (60 mg 0.137 mmol in 1 mL). Preactivated potassium carbonate (95 mg, 0.685 mmol) was added in one portion and the contents were cooled to 0° C. Neat trichloromethyl chloroformate (0.03 mL, 0.274 mmol) was added drop wise and the contents were stirred at 0° C. for 2 h. The reaction mixture was diluted with anhydrous dichloromethane and filtered. The filtrate was concentrated under reduced pressure to yield colorless oil which was dried under reduced pressure for 2 h.

An oven dried round bottom flask was charged with a solution of rac-$N^4$-(7-chloroquinolin-4-yl)-$N^1$,$N^1$-diethylpentane-1,4-diamine in anhydrous dichloromethane (57 mg, 0.18 mmol in 1 mL). Preactivated potassium carbonate (0.124 g, 0.9 mmol) was added in one portion and the contents were cooled to 0° C. A solution of chloromethyl formate in anhydrous dichloromethane (90 mg, 0.18 mmol in 0.5 mL) was added drop wise and the contents were stirred at 0° C. for 1 h. The reaction mixture was diluted with anhydrous dichloromethane and filtered. The filtrate was concentrated under reduced pressure to yield colorless oil which was dried under reduced pressure for 2 h.

An oven dried round bottom flask was charged with a solution of crude mixture (from previous step) in anhydrous dichloromethane (1 mL). Neat trimethylsilylbromide (1 mL) was added and the contents were stirred at room temperature for 24 h. After concentrating under reduced pressure, the reaction mixture was dissolved in methanol and stirred for 5 min. The organic layer was concentrated under reduced pressure and this procedure was repeated three times to yield colored solid. The solids were washed with cold diethyl ether and cold dichloromethane to yield rac-((4-((((7-chloroquinolin-4-yl)(5-(diethylamino)pentan-2-yl)carbamoyl)oxy)methyl)benzamido)meth-ylene)diphosphonic acid.

Figure 16:
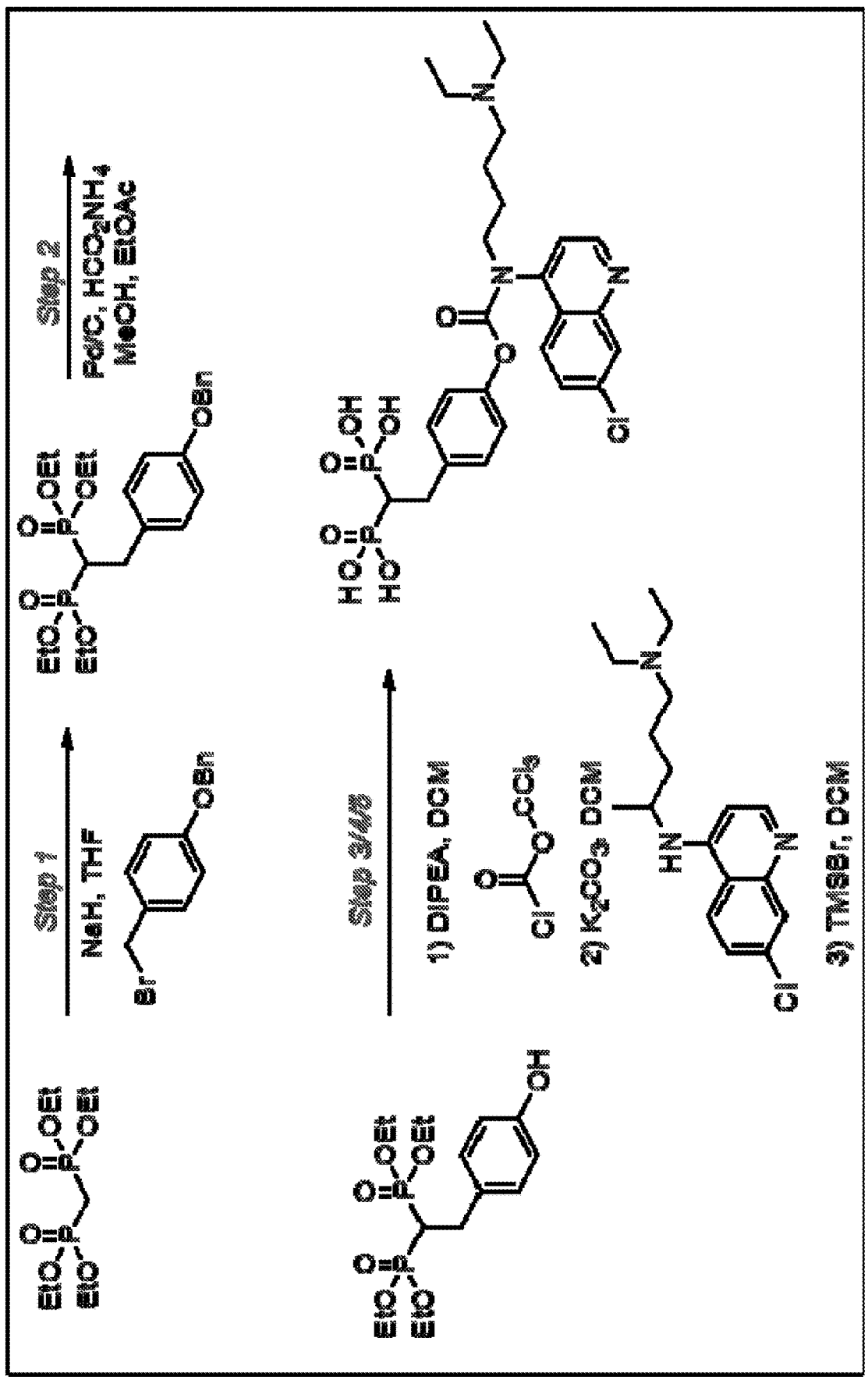
FIG. 16 depicts an exemplary synthesis of rac-(2-(4-(((7-chloroquinolin-4-yl)(4-(diethylamino) butyl)carbamoyl) oxy)phenyl)-ethane-1,1-diyl)diphosphonic acid.

Synthesis of rac-(2-(4-(((7-chloroquinolin-4-yl)(4-(diethylamino) butyl)carbamoyl)oxy)phenyl)-ethane-1,1-diyl)diphosphonic acid An exemplary synthesis of rac-(2-(4-(((7-chloroquinolin-4-yl)(4-(diethylamino) butyl)carbamoyl)oxy)phenyl)-ethane-1,1-diyl)diphosphonic acid is shown in FIG. 16.

Step 1: Synthesis of tetraethyl (2-(4-(benzyloxy)phenyl)ethane-1,1-diyl)bis(phosphonate)

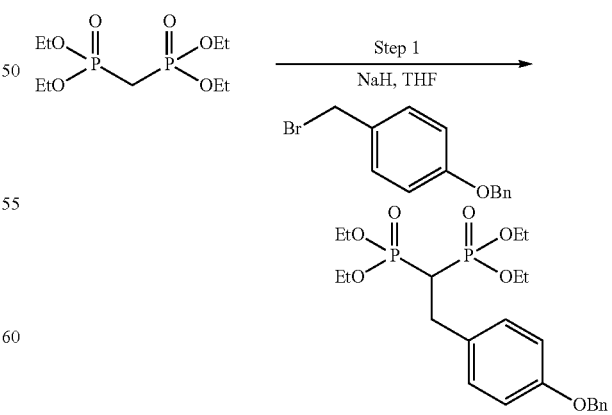

An oven dried round bottom flask was charged with a suspension of sodium hydride in anhydrous tetrahydrofuran (0.35 g, 14.37 mmol in 15 mL). Neat tetraethyl methylenebis (phosphonate) (4.1 g, 14.37 mmol) was added drop wise and the contents were stirred at room temperature for 30 min. A solution of 1-(benzyloxy)-4-(bromomethyl)benzene in anhydrous tetrahydrofuran (2 g, 7.18 mmol in 3 mL) was added and the contents were stirred at room temperature for 10 h. After quenching with an aqueous solution of ammonium chloride (10 mL), the reaction mixture was extracted with ethyl acetate (3×25 mL) and the combined organic layer was washed with brine, dried over anhydrous sodium sulphate, filtered and concentrated under reduced pressure. The crude mixture was purified by column chromatography on alumina (30%-60% of ethyl acetate in n-hexanes) to yield tetraethyl (2-(4-(benzyloxy)phenyl)ethane-1,1-diyl)bis(phosphonate) (2.2 g, 67%) as colorless oil.

$R_f$ 0.5 (100 ethyl acetate, alumina, UV active)

Thermo-MS (ESI) m/z (M+H) Cald for $C_{23}H_{34}O_7P_2$: 485.46, found: 485.5

$^1$H-NMR (400 MHz, CDCl$_3$) δ 7.41-7.21 (m, 5H), 7.13 (d, J=6.8 Hz, 2H), 6.83 (d, J=6.8 Hz, 2H), 4.99 (s, 2H), 4.19-3.95 (m, 8H), 3.2-3.05 (m, 2H), 2.61-2.46 (m, 1H), 1.27-1.13 (m, 12H)

$^{13}$C-NMR (100 MHz, CDCl$_3$) δ 157.35, 137.03, 132.02, 129.89, 128.48, 127.83, 127.32, 114.58, 69.96, 62.44, 39.22 (t, J=528 Hz), 30.33, 16.25

$^{31}$P-NMR (400 MHz, CD$_3$OD) δ 23.71

Step 2: Synthesis of tetraethyl (2-(4-hydroxyphenyl)ethane-1,1-diyl)bis(phosphonate)

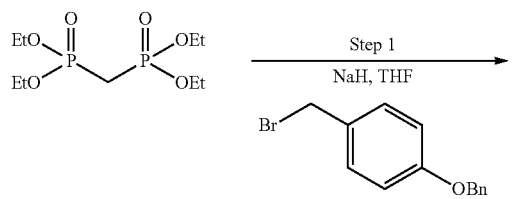

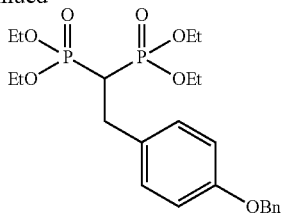

An oven dried round bottom flask was charged with a solution of tetraethyl (2-(4-(benzyloxy)phenyl)ethane-1,1-diyl)bis(phosphonate) in ethyl acetate (0.8 g, 1.64 mmol in 6 mL). A solution of ammonium formate in ethanol (0.3 g, 4.8 mmol in 6 mL) and 10% of palladium on charcoal (0.2 g) were added sequentially and the contents were heated at 55° C. for an hr. The reaction mixture was carefully filtered over celite and the filtrate was concentrated under reduced pressure. The crude mixture was purified on column chromatography on silica (5% of methanol in dichloromethane to yield tetraethyl (2-(4-hydroxyphenyl)ethane-1,1-diyl)bis (phosphonate) (0.69 g, 85%) as colorless oil.

$R_f$ 0.45 (5% of methanol in dichloromethane, KMnO$_4$ active & UV active).

Thermo-MS (ESI) m/z (M+H) Cald for $C_{23}H_{34}O_7P_2$: 485.46, found: 485.5

$^1$H-NMR (500 MHz, CDCl$_3$) δ 7.06 (d, J=6.8 Hz, 2H), 6.68 (d, J=6.8 Hz, 2H), 4.17-3.95 (m, 8H), 3.21-3.05 (m, 2H), 2.65-2.49 (m, 1H), 1.29-1.11 (m, 12H)

$^{13}$C-NMR (100 MHz, CDCl$_3$) δ 155.92, 129.69, 115.20, 62.71, 62.58, 39.12 (t, J=528 Hz), 30.21, 16.22

$^{31}$P-NMR (400 MHz, CD$_3$OD) δ23.74

Step 3/4/5: Synthesis of rac-(2-(4-(((7-chloroquinolin-4-yl)(4-(diethylamino)butyl)carbamoyl)oxy)phenyl)-ethane-1,1-diyl)diphosphonic acid

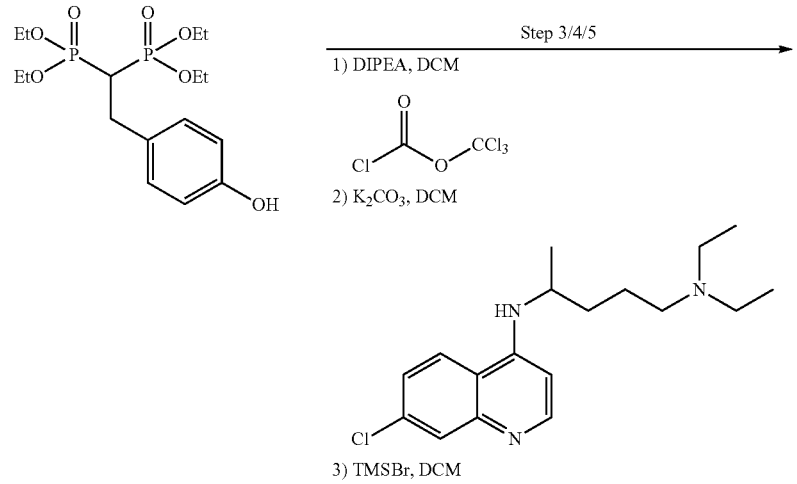

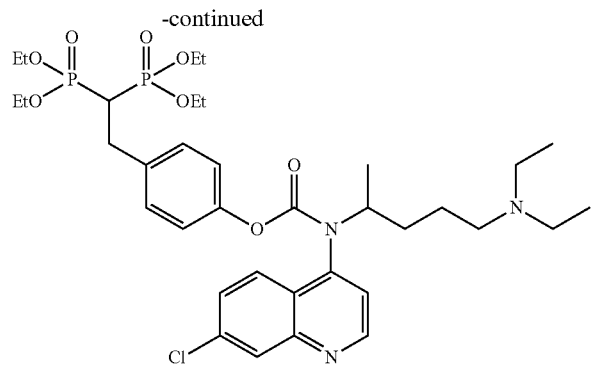

An oven dried round bottom flask was charged with a solution of tetraethyl (2-(4-hydroxyphenyl)ethane-1,1-diyl)bis(phosphonate) in anhydrous dichloromethane (0.15 g, 0.38 mmol in 1 mL). Neat N-ethyl-N-isopropylpropan-2-amine (0.13 mL, 0.76 mmol) was added and the contents were cooled to 0° C. Neat diphosgene (0.09 mL, 0.76 mmol) was added drop wise and the contents were stirred at 0° C. for 2 h. The reaction mixture was concentrated under reduced pressure and dried under high vacuum for 2 h.

An oven dried round bottom flask was charged with a solution of rac-$N^4$-(7-chloroquinolin-4-yl)-$N^1$,$N^1$-diethylpentane-1,4-diamine in anhydrous dichloromethane (0.097 g, 0.304 mmol in 1 mL). Preactivated potassium carbonate (0.262 g, 1.9 mmol) was added and the contents were cooled to 0° C. A solution of chloroformate in anhydrous dichloromethane (0.17 g, 0.38 mmol in 0.3 mL) was added drop wise and the contents were stirred at 0° C. for 3 h. The reaction mixture was diluted with anhydrous dichloromethane (10 mL) and filtered. The filtrate was concentrated under reduced pressure and redissolved in anhydrous dichloromethane (1 mL). Neat trimethylsilyl bromide (1 mL) was added and the contents were stirred at room temperature for 14 h. The reaction mixture was concentrated under reduced pressure and the crude mixture was dissolved in 10 mL methanol and stirred at room temperature for 5 min. The organic layer was concentrated under reduced pressure and this procedure was repeated three times to yield colored solid. The solids were washed with cold diethyl ether and cold dichloromethane to yield rac-(2-(4-(((7-chloroquinolin-4-yl)(4-(diethylamino)butyl)carbamoyl)oxy)phenyl)-ethane-1,1-diyl)diphos-phonic acid.

Figure 17:
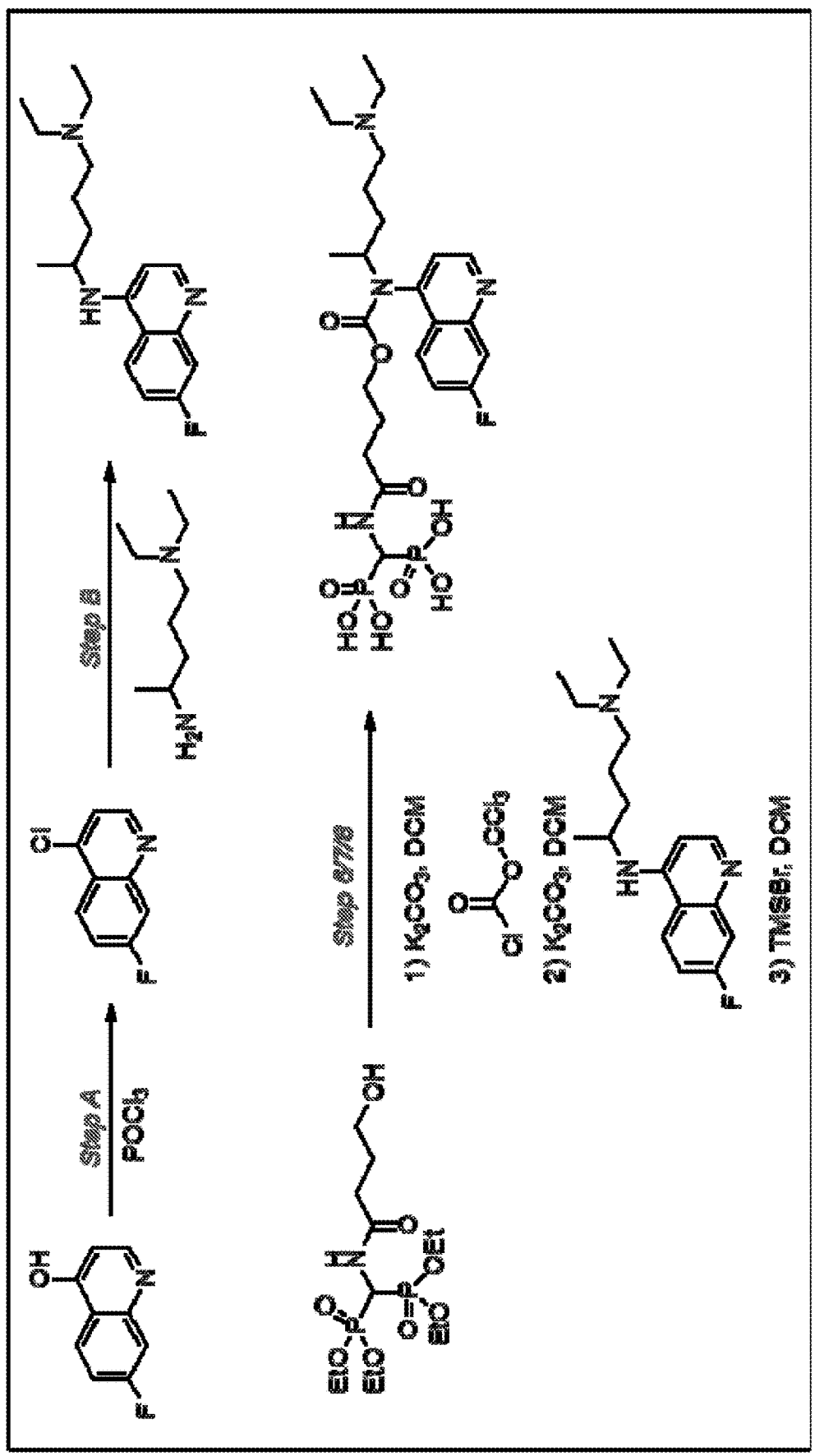
FIG. 17 depicts an exemplary synthesis of rac-(14-ethyl-9-(7-fluoroquinolin-4-yl)-10-methyl-3,8-dioxo-7-oxa-2,9,14-triazahexadecane-1,1-diyl)diphosphonic acid.

Synthesis of rac-(14-ethyl-9-(7-fluoroquinolin-4-yl)-10-methyl-3,8-dioxo-7-oxa-2,9,14-triazahexadecane-1,1-diyl)diphosphonic acid An exemplary synthesis of rac-(14-ethyl-9-(7-fluoroquinolin-4-yl)-10-methyl-3,8-dioxo-7-oxa-2,9,14-triazahexadecane-1,1-diyl)diphosphonic acid is shown in FIG. 17.

Step A: Synthesis of 4-chloro-7-fluoroquinoline

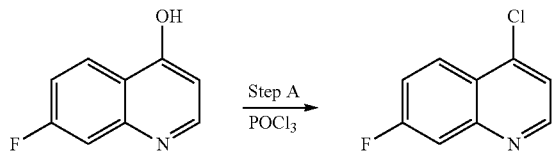

An oven dried round bottom flask was charged with 7-fluoroquinolin-4-ol (1.1 g, 6.7 mmol). Neat phosphorous oxychloride (15 mL) was added and the contents were heated at 70° C. for 3 h. After concentrating under reduced pressure, the reaction mixture was carefully poured in ice cold water (30 mL) and neutralized with an aqueous solution of sodium bicarbonate. The aqueous layer was extracted with dichloromethane (5×20 mL) and the combined organic layer was washed with brine, dried over anhydrous sodium sulphate, filtered and concentrated under reduced pressure. The crude mixture was purified by column chromatography on silica (10%-40% of ethyl acetate in n-hexanes) to yield 4-chloro-7-fluoroquinoline (1.2 g, 98%) as white solid.

$R_f$=0.7 (40% of ethyl acetate in n-hexanes, UV active).

Thermo-MS (ESI) m/z (M+H) Cald for $C_9H_5ClFN$: 182.59, found: 182.6

$^1$H-NMR (500 MHz, CDCl$_3$) δ 8.71 (d, J=3.6 Hz, 1H), 8.32-8.21 (m, 1H), 7.69-7.64 (m, 1H), 7.59 (d, J=3.6 Hz, 1H), 7.52-7.41 (m, 1H).

$^{13}$C-NMR (100 MHz, CDCl$_3$) δ 164.7, 162.2, 151.03, 150.24, 150.11, 142.66, 126.58, 126.49, 123.54, 120.61, 118.19, 177.94, 113.56, 113.35

Step B: Synthesis of $N^1$,$N^1$-diethyl-$N^4$-(7-fluoroquinolin-4-yl)pentane-1,4-diamine

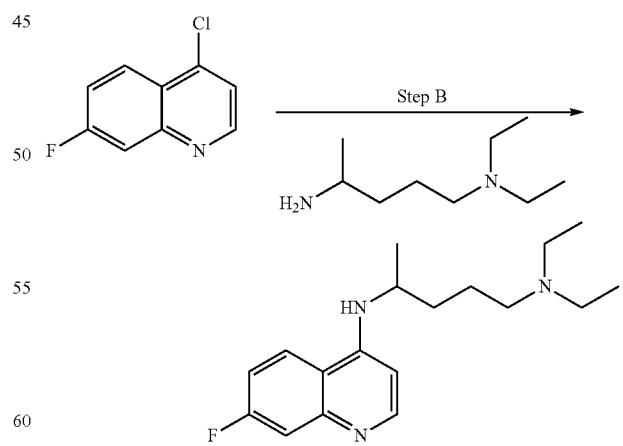

An oven dried 10 mL vial was charged with 4-chloro-7-fluoroquinoline (0.5 g, 2.5 mmol). Neat 2-amino-5-diethylaminopentane (1.2 mL, 6.2 mmol) was added and the contents were heated at 100° C. for 2 h and at 150° C. for 5 h. The reaction mixture was purified on column chromatography on alumina (10%-40% of ethyl acetate in n-hexanes) to yield $N^1,N^1$-diethyl-$N^4$-(7-fluoroquinolin-4-yl)pentane-1,4-diamine (0.4 g, 48%) as white solid.

$R_f$ 0.5 (20% of ethyl acetate in n-hexanes, alumina, UV active)

Thermo-MS (ESI) m/z (M+H) Cald for $C_{18}H_{26}FN_3$: 304.42, found: 304.4

$^1$H-NMR (500 MHz, CDCl$_3$) δ 88.47 (d, J=4 Hz, 1H), 7.67 (dd, =3.2 Hz, J$_2$=5.2 Hz, 1H), 7.54 (dd, J$_1$=4 Hz, J$_2$=8 Hz, 1H), 7.19-7.05 (m, 1H), 6.37 (d, J=8 Hz, 1H), 5.15 (d, J=4 Hz, 1H), 3.75-3.61 (m, 1H), 2.48 (q, J=8 Hz, 4H), 2.41 (t, J=8 Hz, 2H), 1.71-1.47 (m, 4H), 1.28 (d, J=8 Hz, 3H), 0.97 (t, J=8 Hz, 6H)

$^{13}$C-NMR (100 MHz, CDCl$_3$) δ 163.91, 161.44, 151.86, 150.02, 149.90, 149.35, 122.33, 122.23, 115.83, 113.93, 113.93, 113.68, 113.07, 112.87, 98.56, 52.4, 48.17, 46.64, 34.35, 23.74, 20.01, 11.28

Step 6/7/8: Synthesis of rac-(14-ethyl-9-(7-fluoroquinolin-4-yl)-10-methyl-3,8-dioxo-7-oxa-2,9,14-triazahexadecane-1,1-diyl)diphosphonic acid

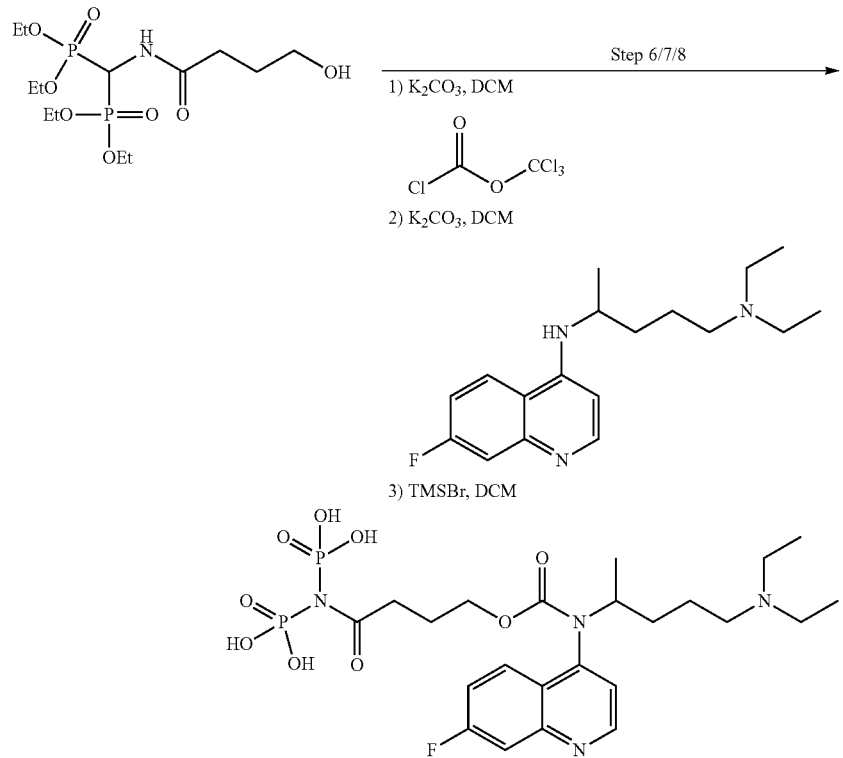

An oven dried round bottom flask was charged with a solution of tetraethyl ((4-hydroxybutanamido)methylene)bis(phosphonate) in anhydrous dichloromethane (0.096 g, 0.246 mmol in 1.4 mL) and pre-activated potassium carbonate (0.31 g, 2.17 mmol). After cooling to 0° C., neat diphosgene (0.06 mL, 0.492 mmol) was added drop wise and the contents were stirred at 0° C. for 2 h. The reaction mixture was diluted with anhydrous dichloromethane (10 mL) and the contents were filtered. The filtrate was concentrated under reduced pressure and dried under high vacuum for 2 h, before taking to the next step.

An oven dried round bottom flask was charged with the solution of rac-$N^1,N^1$-diethyl-$N^4$-(7-fluoroquinolin-4-yl)pentane-1,4-diamine in anhydrous dichloromethane (0.08 g, 0.259 mmol in 0.5 mL). Potassium carbonate (0.3 g, 2.24 mmol) was added and the white suspension was cooled to 0° C. A solution of chloroformate in anhydrous dichloromethane (0.12 g, 0.259 mmol in 0.7 mL) was added and the contents were stirred at 0° C. for 2 h. The reaction mixture was diluted with dichloromethane (10 mL) and the contents were filtered. The filtrate was concentrated under reduced pressure and the crude mixture was taken to the next step without purification.

An oven dried round bottom flask was charged with a solution of crude mixture from previous step in anhydrous dichloromethane (0.176 g, 0.246 mmol in 1.1 mL). After cooling to 0° C., neat trimethylsilyl bromide (1 mL) was added and the contents were gradually warmed to room temperature and stirred for 36 h. The reaction mixture was concentrated under reduced pressure and the crude mixture was dissolved in anhydrous methanol (10 mL). After stirring at room temperature for 10 min, the reaction mixture was concentrated under reduced pressure. The above process was repeated twice and the crude mixture was washed with diethyl ether (3 times) to yield rac-(14-ethyl-9-(7-fluoroquinolin-4-yl)-10-methyl-3,8-dioxo-7-oxa-2,9,14-triazahexadecane-1,1-diyl)diphosphonic acid.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A compound selected from the group consisting of:
i) a compound of formula (III)

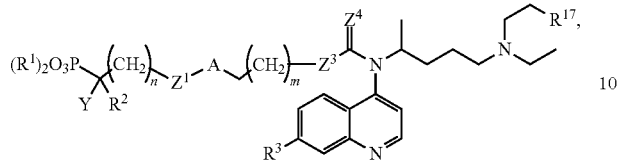

wherein in formula (III):
each occurrence of $R^1$ is independently selected from the group consisting of hydrogen and alkyl;
$R^2$ is selected from the group consisting of hydrogen, alkyl, $-OR^8$, $-N(R^8)(R^9)$, and halogen;
$R^3$ is selected from the group consisting of halogen, $NO_2$, $-CF_3$, $-OR^{16}$, and $-CH_3$;
Y is selected from the group consisting of $-PO(OR^{10})(OR^{11})$, $-PO(R^{10})(OR^{11})$, $-CO_2R^{10}$, and $-SO_3R^{10}$;
$Z^1$ is selected from the group consisting of $CH_2$ and $NR^{12}$;
A is selected from the group consisting of $CH_2$, $C(=O)$, $C(=NR^{13})$, and $C(=S)$;
$Z^3$ is selected from the group consisting of $CH_2$, $NR^7$, S, and O;
$Z^4$ is selected from the group consisting of O, $NR^{15}$, and S;
$R^8$ and $R^9$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;
$R^{10}$ and $R^{11}$ are each independently selected from the group consisting of hydrogen and alkyl;
$R^7$, $R^{12}$, $R^{13}$, $R^{14}$, $R^{15}$, and $R^{16}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;

$R^{17}$ is selected from the group consisting of hydrogen, $-OR^{18}$, $-CH_3$, and $-CF_3$;
$R^{18}$ is selected from the group consisting of hydrogen and alkyl, wherein alkyl is optionally substituted with one to four substituents selected from the group consisting of hydroxyl, alkoxy, alkenyl, cycloalkyl, aryl, heteroaryl, halo, cyano and amino;
n is an integer from 0 to 10; and
m is an integer from 0 to 10;
ii) a compound of formula (IV):

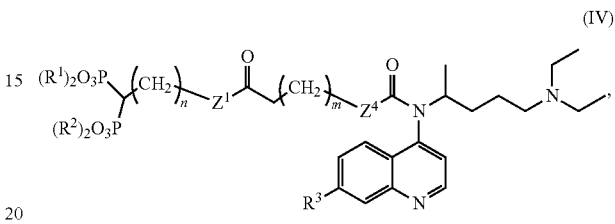

wherein in formula (IV):
each occurrence of $R^1$ and $R^2$ is independently selected from the group consisting of hydrogen and alkyl;
$R^3$ is selected from the group consisting of halogen, $-CF_3$, $-OR^{16}$, and $-CH_3$;
$Z^1$ is selected from the group consisting of $CH_2$ and $NR^{12}$;
$Z^4$ is selected from the group consisting of O, $NR^{15}$, and S;
$R^{12}$, $R^{15}$, and $R^{16}$ are each independently selected from the group consisting of hydrogen and alkyl, wherein the alkyl group is optionally substituted with one to four substituents selected from the group consisting of hydroxyl, alkoxy, alkenyl, cycloalkyl, aryl, heteroaryl, halo, cyano and amino;
n is an integer from 0 to 10; and
m is an integer from 0 to 10;
or
a pharmaceutically acceptable salt thereof; or an isomer thereof; or a mixture of isomers thereof.
2. The compound of claim 1, wherein Y is $-PO_3(R^1)_2$.
3. The compound of claim 1, wherein $Z^4$ is O.
4. The compound of claim 1, wherein $R^3$ is Cl.
5. The compound of claim 1, wherein the compound is selected from the group consisting of:

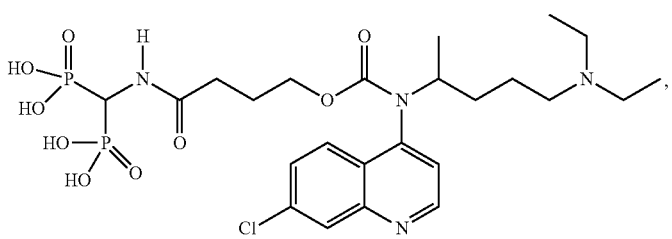

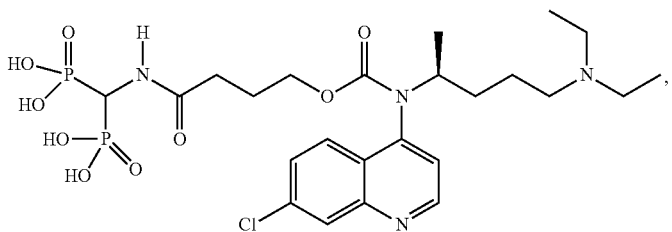

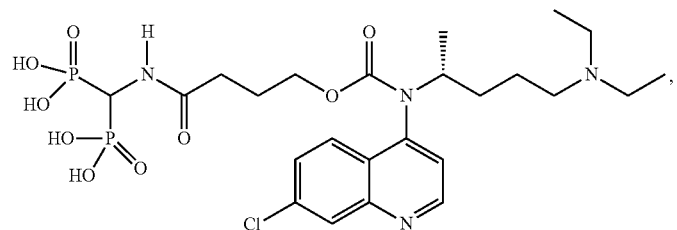
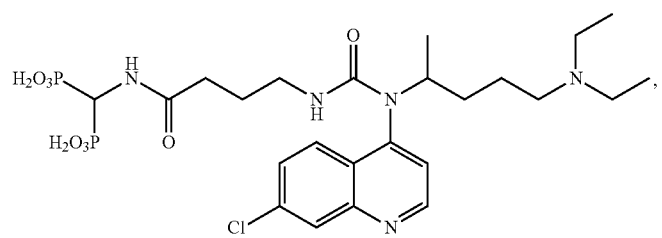
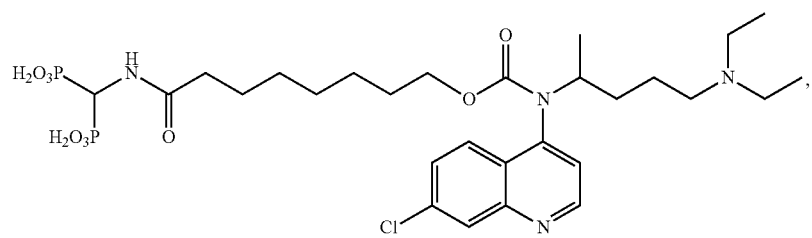
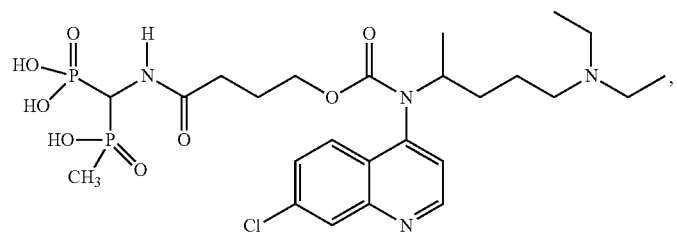
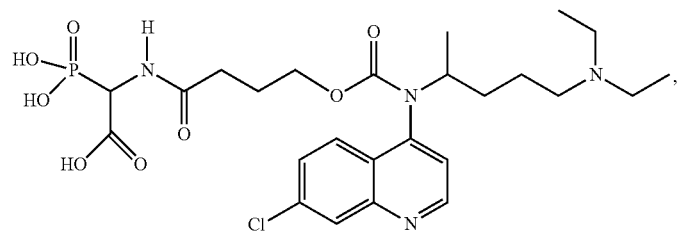
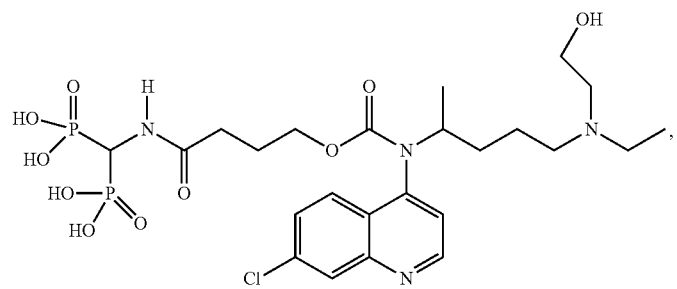
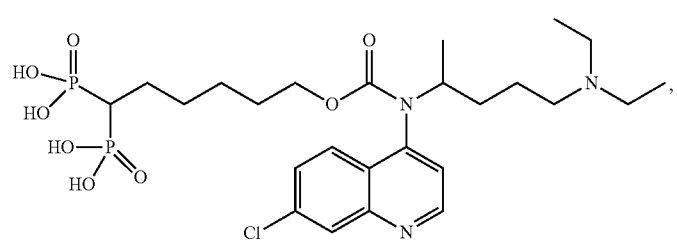

-continued
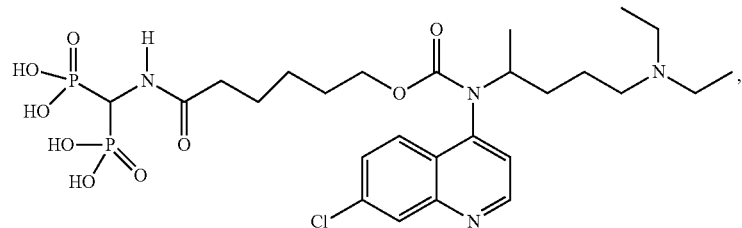
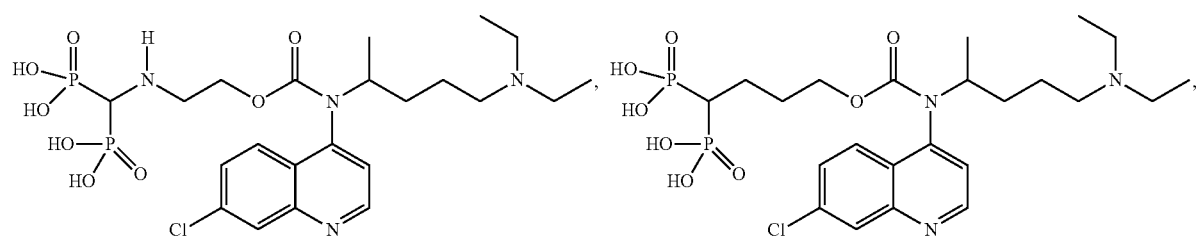
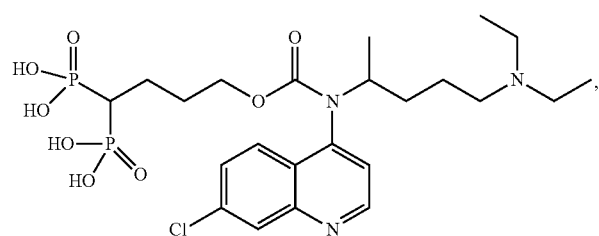
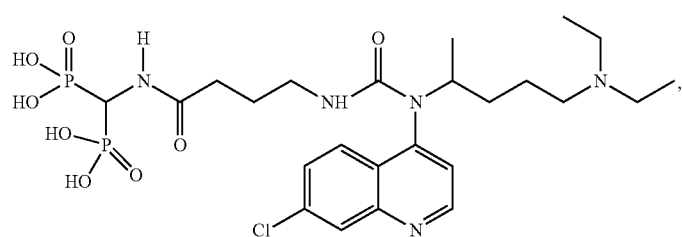
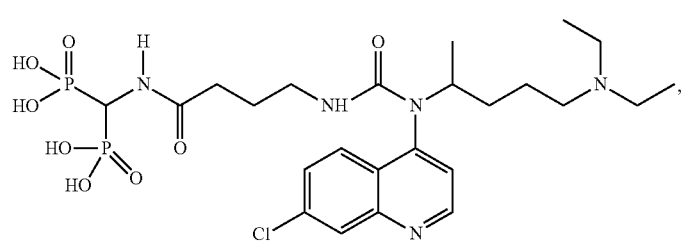
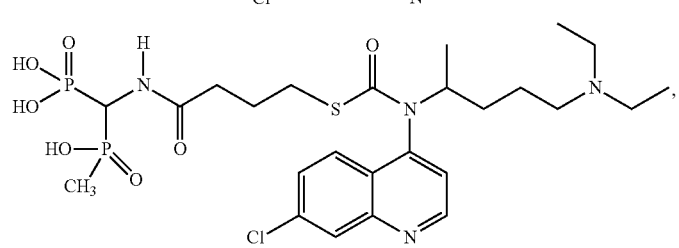
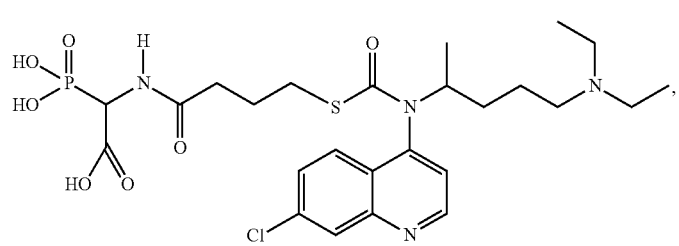

-continued
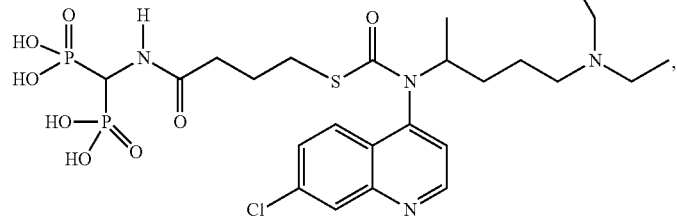
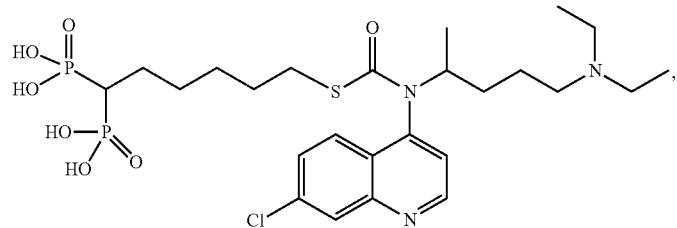
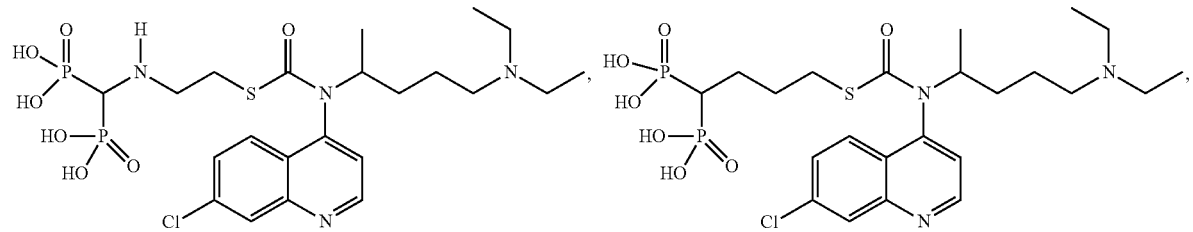
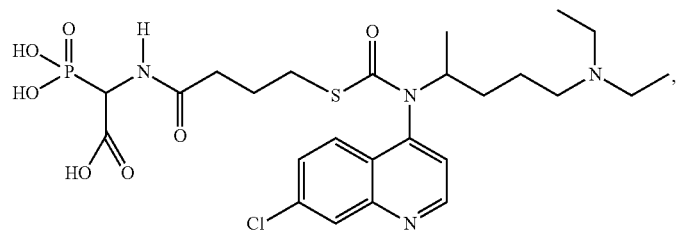
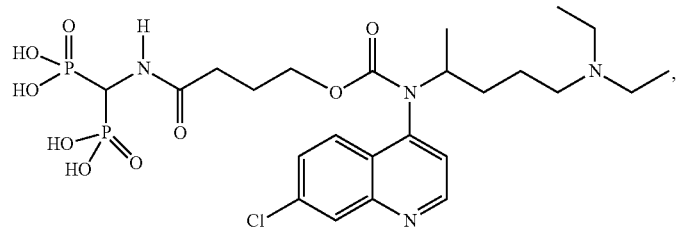
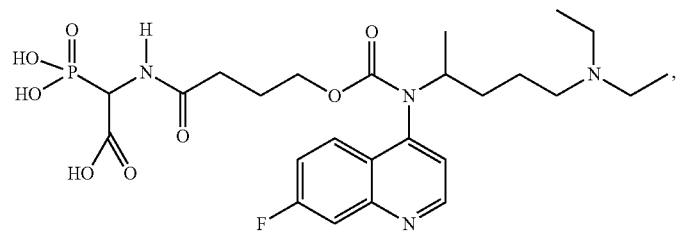
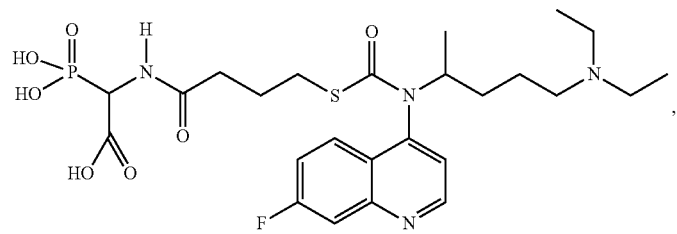

-continued
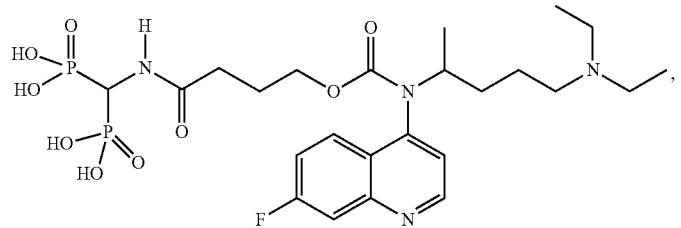
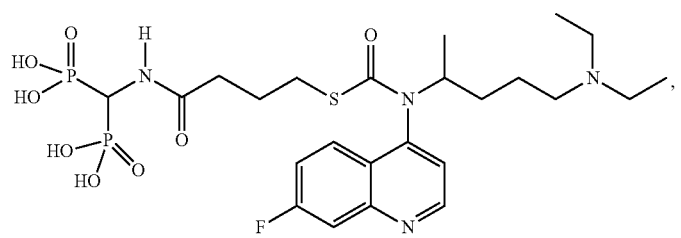
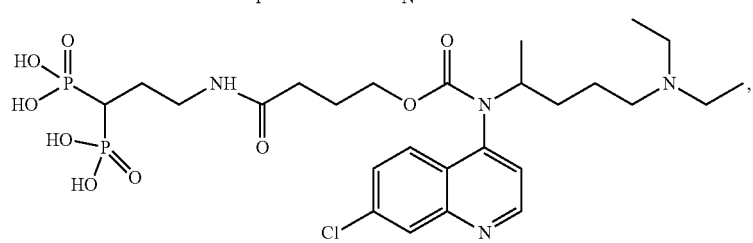
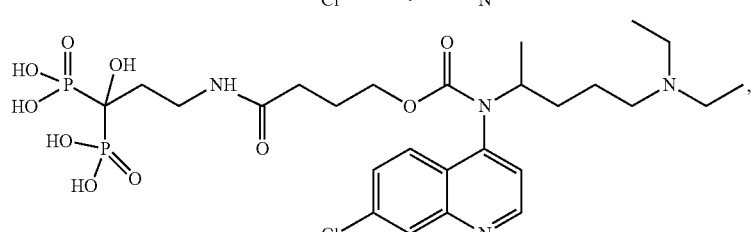
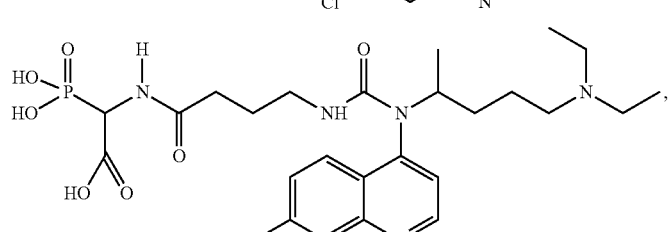
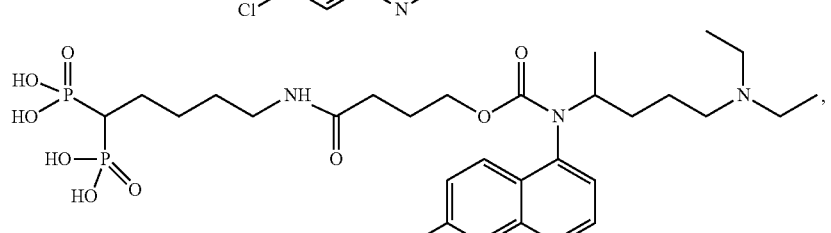
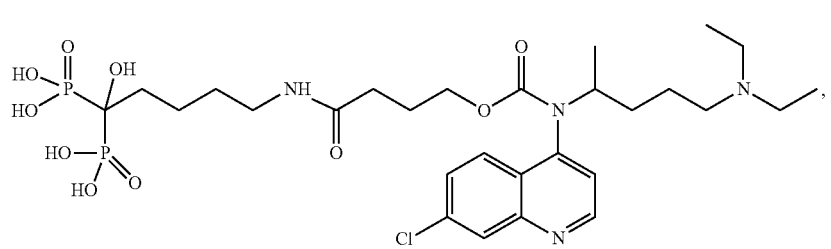

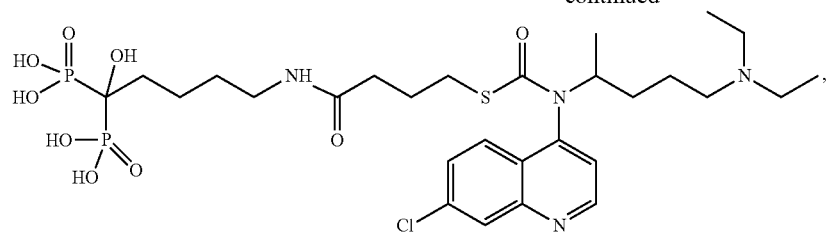
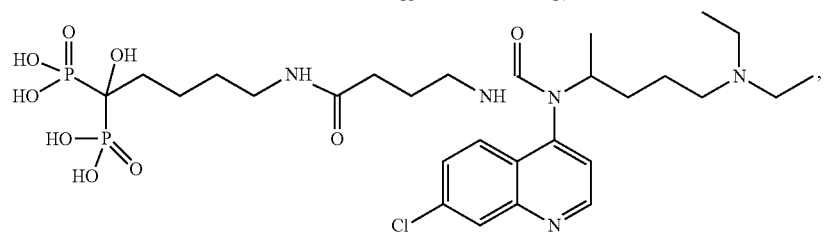
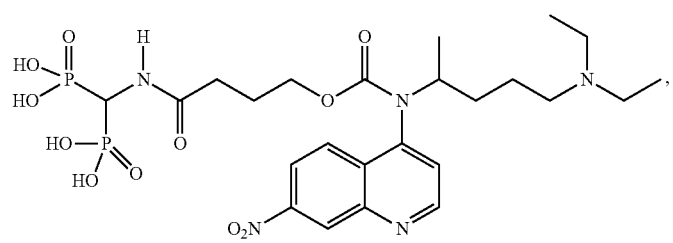
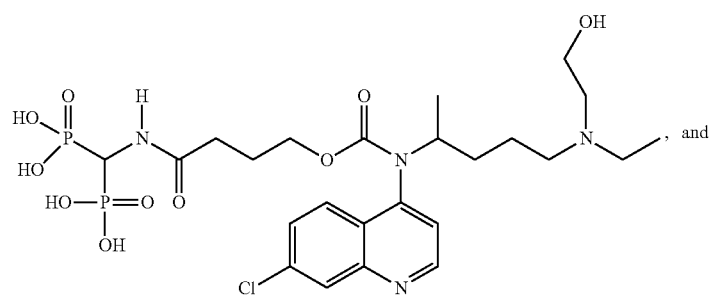
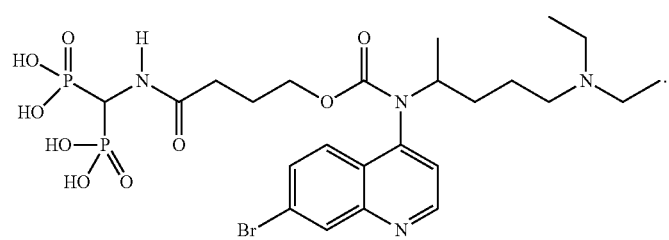

a pharmaceutically acceptable salt thereof, an isomer thereof, or a mixture of isomers thereof.

6. The compound of claim 1, wherein the compound is

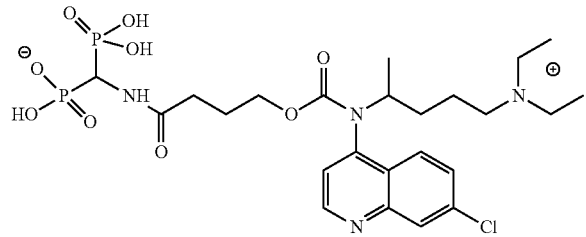 [SMILES: CCN(CC)CCCC(C)N(C(=O)OCCCC(=O)NC(P(=O)([O-])O)P(=O)(O)O)c1ccnc2cc(Cl)ccc12]

a pharmaceutically acceptable salt thereof, an isomer thereof, or a mixture of isomers thereof.

7. A method of promoting bone formation at a site in need of bone formation in a subject or reducing bone resorption in a subject in need of less bone resorption, or both, the method comprising administering a therapeutically effective amount of a composition comprising at least one compound of claim 1.

8. The method of claim 7, wherein the at least one compound is selected from the group consisting of:

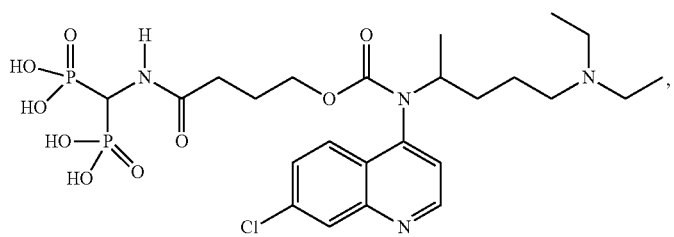

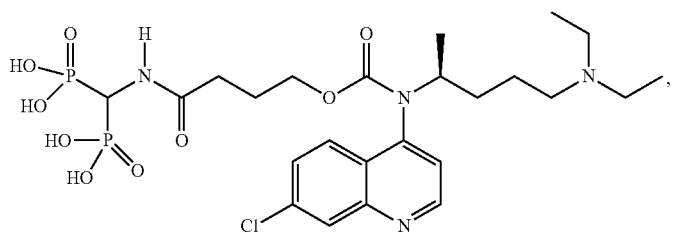

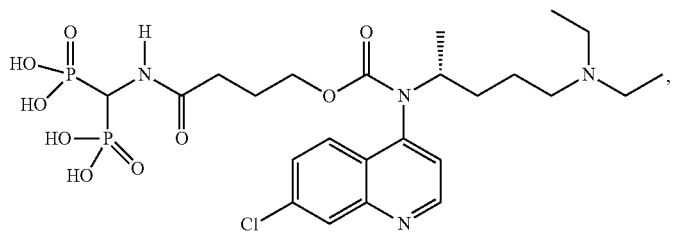

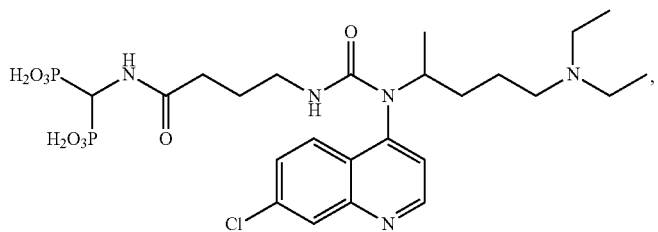

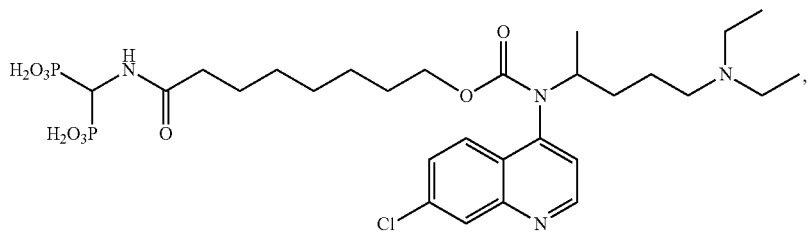

-continued
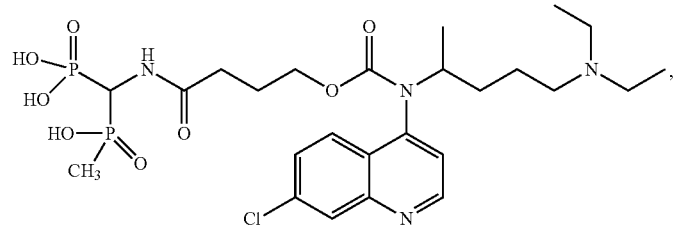
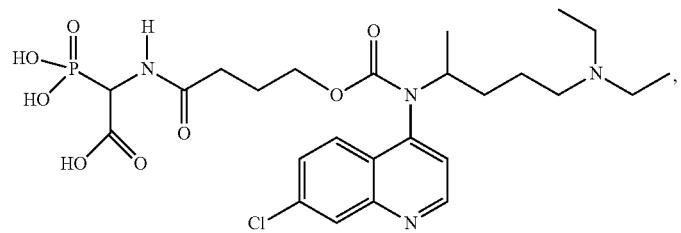
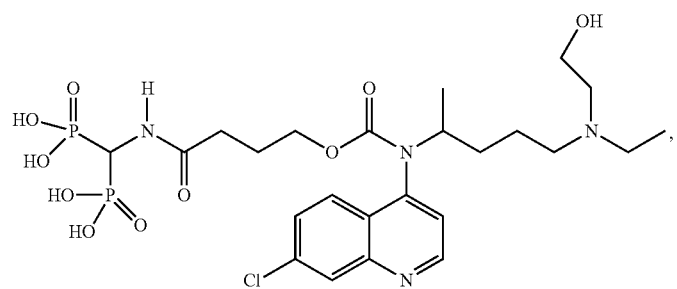
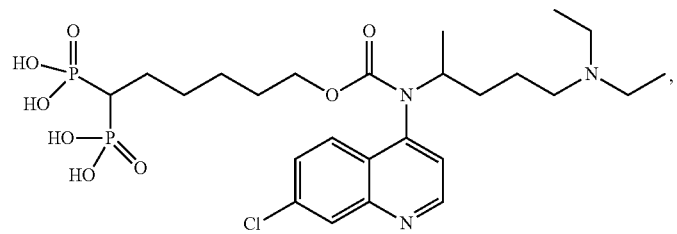
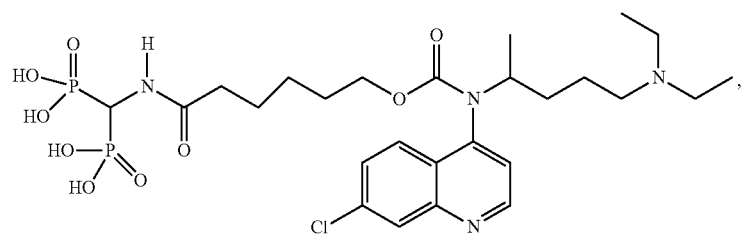
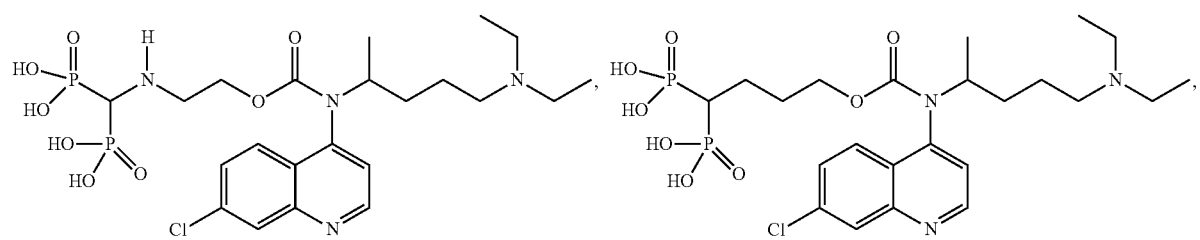
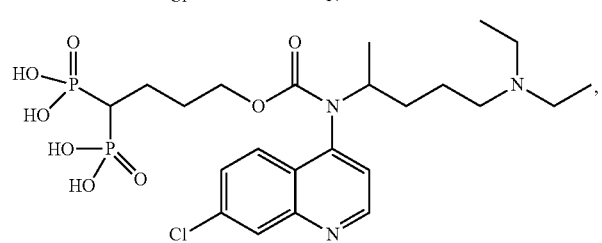

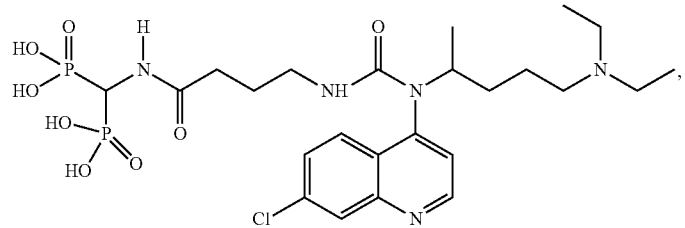
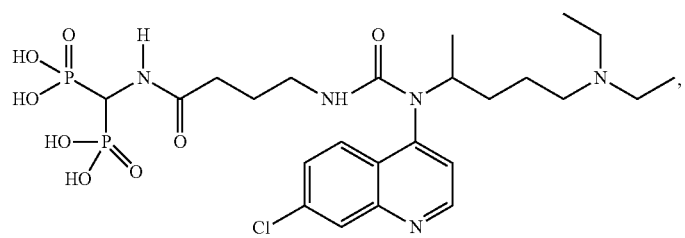
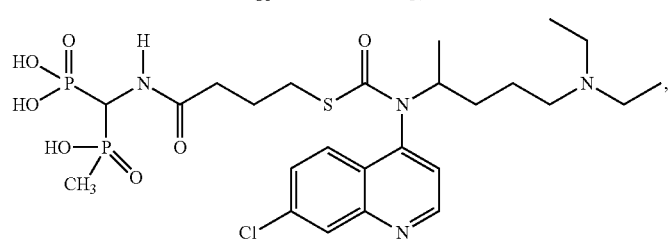
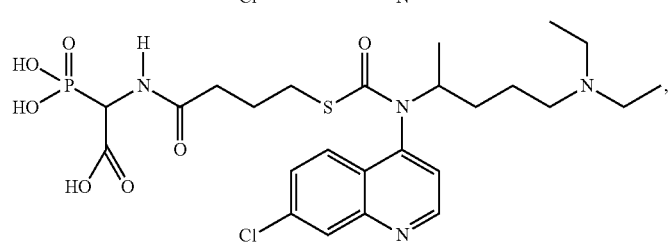
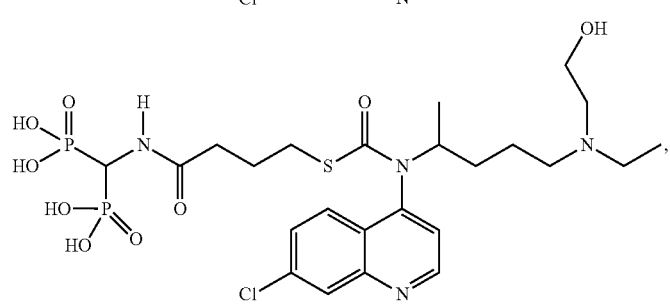
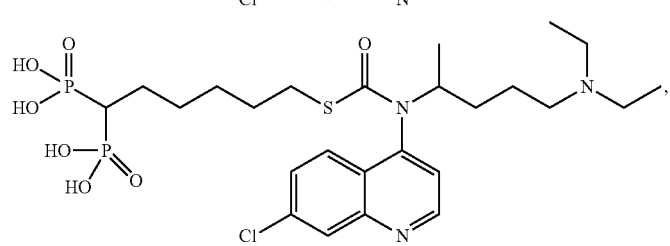
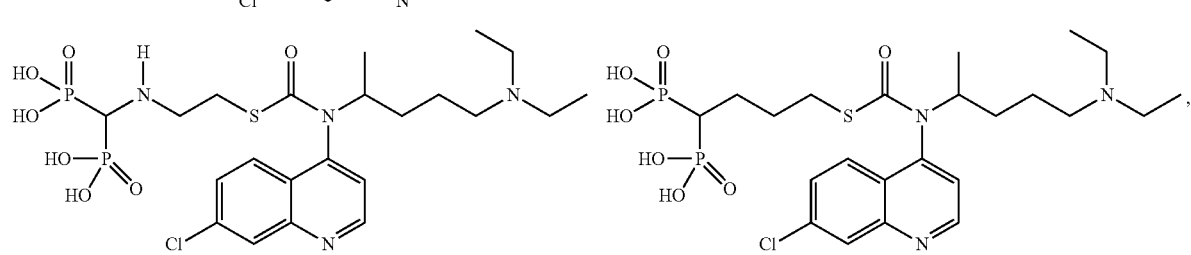

-continued
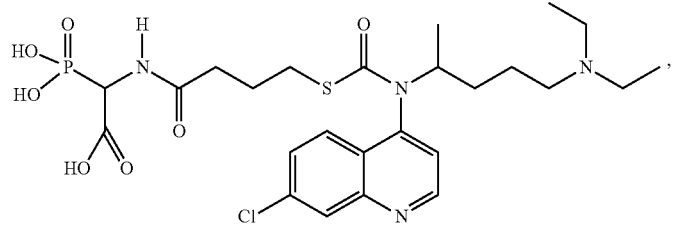
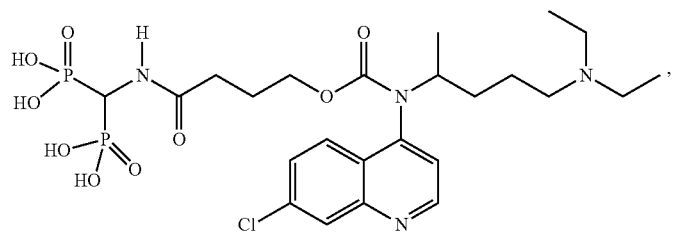
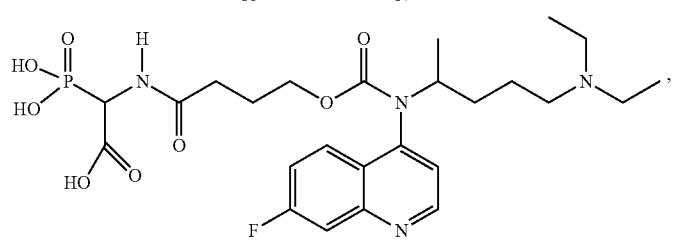
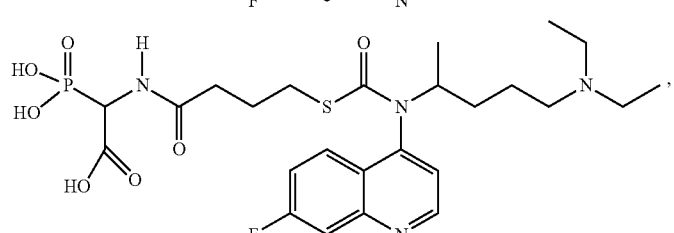
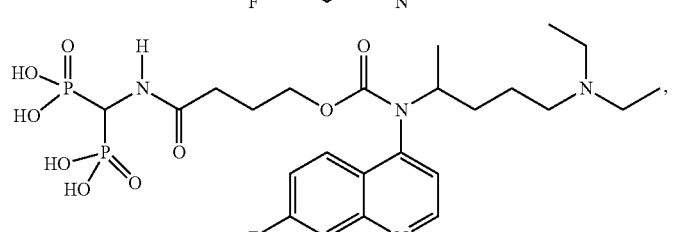
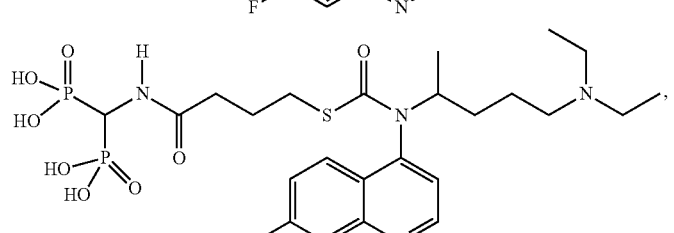
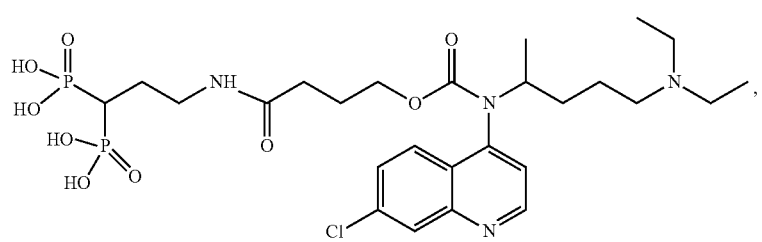

-continued
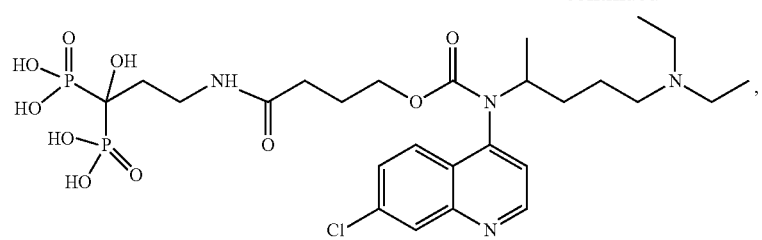 [SMILES: CCN(CC)CCCC(C)N(C(=O)OCCCC(=O)NCCC(O)(P(=O)(O)O)P(=O)(O)O)c1ccnc2cc(Cl)ccc12]
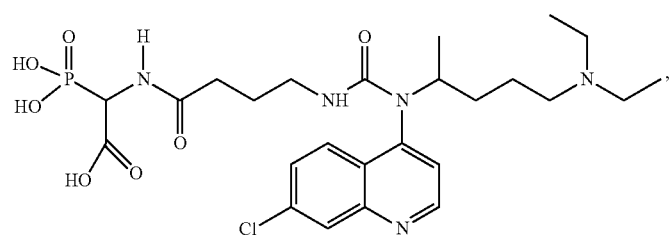
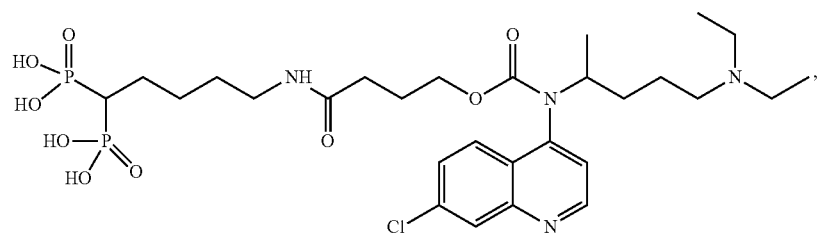
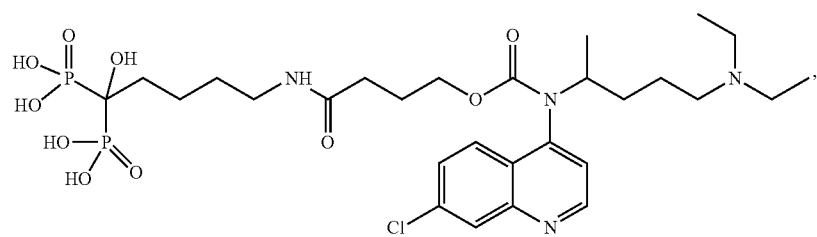
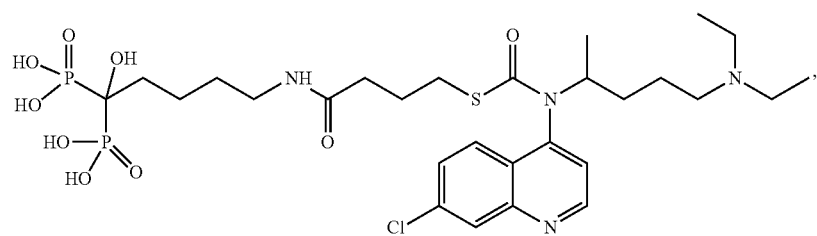
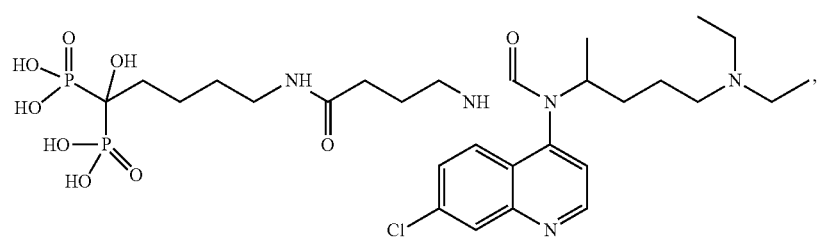
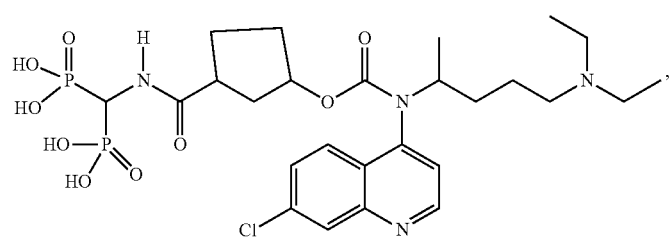

-continued

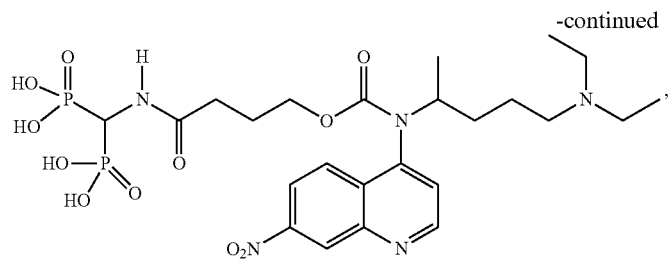

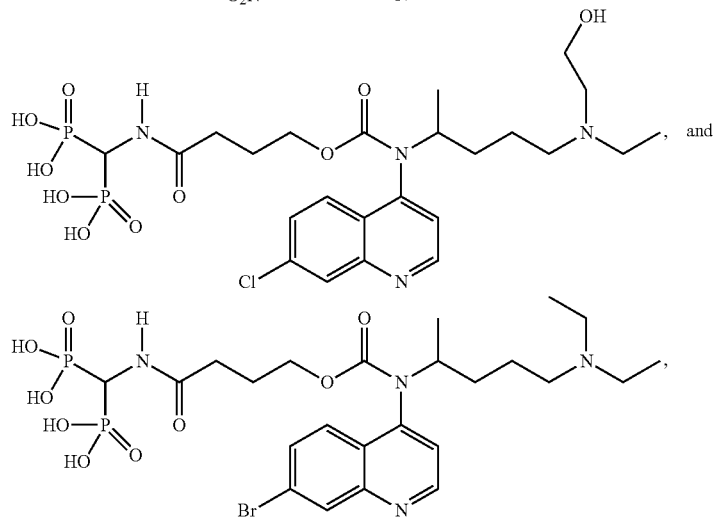

a pharmaceutically acceptable salt thereof, an isomer thereof, or a mixture of isomers thereof.

9. The method of claim 7, wherein the at least one compound

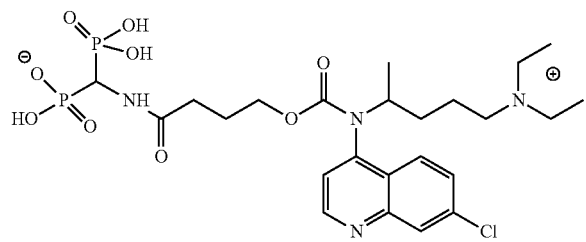 [SMILES: CCN(CC)CCCC(C)N(C(=O)OCCCC(=O)NC(P(=O)([O-])O)P(=O)(O)O)c1ccnc2cc(Cl)ccc12]

a pharmaceutically acceptable salt thereof, an isomer thereof, or a mixture of isomers thereof.

10. A method of inhibiting inflammation at a site in need thereof, the method comprising administering a therapeutically effective amount of a composition comprising at least one compound of claim 1.

11. The method of claim 10, wherein the at least one compound is

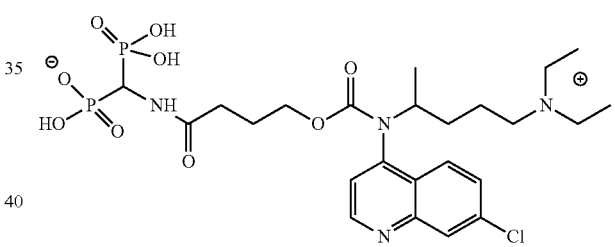

a pharmaceutically acceptable salt thereof, an isomer thereof, or a mixture of isomers thereof.

12. The method of claim 7, wherein the subject has a disease or disorder selected from the group consisting of multiple myeloma, osteoporosis, osteonecrosis, osteomyelitis, osteoarthritis, rheumatoid, psoriatic and other forms of inflammatory arthritis, Paget's disease, bone cancer, cancers metastasized to bone, multiple myeloma, prosthesis loosening, and bone fracture and repair.

13. The method of claim 7, wherein the subject has arthritis.

14. The method of claim 7, wherein the composition further comprises at least one pharmaceutically acceptable carrier.

15. The method of claim 7, wherein the therapeutic agent is controllably released from the compound at the site in need thereof.

* * * * *